(12) United States Patent
Fermann et al.

(10) Patent No.: US 9,153,928 B2
(45) Date of Patent: Oct. 6, 2015

(54) OPTICAL SIGNAL PROCESSING WITH MODELOCKED LASERS

(75) Inventors: Martin Fermann, Dexter, MI (US); Ingmar Hartl, Ann Arbor, MI (US); Axel Ruehl, Amsterdam (NL)

(73) Assignee: IMRA AMERICA, INC., Ann Arbor, MI (US)

( * ) Notice: Subject to any disclaimer, the term of this patent is extended or adjusted under 35 U.S.C. 154(b) by 1000 days.

(21) Appl. No.: 12/895,127

(22) Filed: Sep. 30, 2010

(65) Prior Publication Data

US 2011/0080580 A1 Apr. 7, 2011

Related U.S. Application Data

(60) Provisional application No. 61/364,545, filed on Jul. 15, 2010, provisional application No. 61/301,722, filed on Feb. 5, 2010, provisional application No. 61/286,179, filed on Dec. 14, 2009, provisional application No. 61/248,207, filed on Oct. 2, 2009.

(51) Int. Cl.
*H01S 3/067* (2006.01)
*G01J 3/45* (2006.01)
(Continued)

(52) U.S. Cl.
CPC . *H01S 3/067* (2013.01); *G01J 3/45* (2013.01); *G01N 21/31* (2013.01); *G01N 21/3581* (2013.01); *G01N 21/4795* (2013.01); *G01N 21/636* (2013.01); *G01N 21/65* (2013.01); *H01S 3/1115* (2013.01); *G01N 2021/3595* (2013.01);
(Continued)

(58) Field of Classification Search
CPC ................................. G01J 3/45; G01J 3/453

USPC ........................ 356/450, 451, 484; 372/29.02
See application file for complete search history.

(56) References Cited

U.S. PATENT DOCUMENTS 4,191,473 A  3/1980 Haensch
4,451,923 A  5/1984 Haensch
(Continued)

FOREIGN PATENT DOCUMENTS

JP  46-19503 B   6/1971
JP  11-221684 A  8/1999
(Continued)

OTHER PUBLICATIONS

Bartels A., et al., Broadband phase-coherent optical frequency synthesis with actively linked Ti:sapphire and Cr:forsterite femtosecond lasers, Opt. Lett. 29, 403-405. (2004).
(Continued)

*Primary Examiner* — Kara E Geisel
(74) *Attorney, Agent, or Firm* — Sughrue Mion, PLLC; Richard C. Turner

(57) ABSTRACT

The invention relates to scanning pulsed laser systems for optical imaging. Coherent dual scanning laser systems (CDSL) are disclosed and some applications thereof. Various alternatives for implementation are illustrated. In at least one embodiment a coherent dual scanning laser system (CDSL) includes two passively modelocked fiber oscillators. In some embodiments an effective CDSL is constructed with only one laser. At least one embodiment includes a coherent scanning laser system (CSL) for generating pulse pairs with a time varying time delay. A CDSL, effective CDSL, or CSL may be arranged in an imaging system for one or more of optical imaging, microscopy, micro-spectroscopy and/or THz imaging.

34 Claims, 27 Drawing Sheets

(51) Int. Cl.

| | | |
|---|---|---|
| G01N 21/31 | (2006.01) | |
| G01N 21/3581 | (2014.01) | |
| G01N 21/47 | (2006.01) | |
| G01N 21/63 | (2006.01) | |
| G01N 21/65 | (2006.01) | |
| H01S 3/11 | (2006.01) | |
| G01N 21/35 | (2014.01) | |
| H01S 3/105 | (2006.01) | |
| H01S 3/106 | (2006.01) | |
| H01S 3/107 | (2006.01) | |

(52) U.S. Cl.
CPC ............... *H01S 3/105* (2013.01); *H01S 3/107* (2013.01); *H01S 3/1068* (2013.01)

(56) References Cited

U.S. PATENT DOCUMENTS

| | | | |
|---|---|---|---|
| 4,700,150 | A | 10/1987 | Hall |
| 5,079,444 | A | 1/1992 | Kallenbach |
| 5,359,612 | A | 10/1994 | Dennis |
| 5,379,309 | A | 1/1995 | Logan |
| 5,479,422 | A | 12/1995 | Fermann |
| 5,748,309 | A | 5/1998 | VanDeWeide |
| 5,778,016 | A | 7/1998 | Sucha |
| 6,038,055 | A | 3/2000 | Hnsch |
| 6,072,811 | A | 6/2000 | Fermann |
| 6,192,058 | B1 | 2/2001 | Abeles |
| 6,373,867 | B1 | 4/2002 | Lin |
| 6,396,856 | B1 | 5/2002 | Sucha |
| 6,570,704 | B2 | 5/2003 | Palese |
| 6,590,910 | B2 | 7/2003 | Lin |
| 6,654,394 | B1 | 11/2003 | Sellin |
| 6,724,788 | B1 | 4/2004 | Holzwarth |
| 6,751,385 | B2 | 6/2004 | Futami |
| 6,785,303 | B1 | 8/2004 | Holzwarth |
| 6,813,429 | B2 | 11/2004 | Price |
| 6,813,447 | B2 | 11/2004 | Ellis |
| 6,814,376 | B2 | 11/2004 | Yu |
| 6,819,690 | B2 | 11/2004 | Kartner |
| 6,885,683 | B1 | 4/2005 | Fermann |
| 6,897,959 | B2 | 5/2005 | Haensch |
| 6,956,887 | B2 | 10/2005 | Jiang |
| 7,026,594 | B2 | 4/2006 | Holzwarth |
| 7,190,705 | B2 | 3/2007 | Fermann |
| 7,202,993 | B2 | 4/2007 | Tauser |
| 7,203,402 | B2 | 4/2007 | Hansch |
| 7,218,443 | B2 | 5/2007 | Tauser |
| 7,224,518 | B2 | 5/2007 | Tauser |
| 7,414,780 | B2 | 8/2008 | Fermann |
| 7,418,017 | B2 | 8/2008 | Holzwarth |
| 7,450,813 | B2 | 11/2008 | Dong |
| 7,496,260 | B2 | 2/2009 | Dong |
| 7,605,371 | B2 | 10/2009 | Yasui |
| 7,649,915 | B2 | 1/2010 | Fermann |
| 7,659,977 | B2 | 2/2010 | Koo |
| 7,728,317 | B2 | 6/2010 | Dilhaire |
| 7,782,910 | B2 | 8/2010 | Fermann |
| 7,804,863 | B2 | 9/2010 | Adel |
| 7,809,222 | B2 | 10/2010 | Hartl |
| 2004/0057682 | A1 | 3/2004 | Nicholson |
| 2004/0190119 | A1 | 9/2004 | Tauser |
| 2004/0213302 | A1 | 10/2004 | Fermann |
| 2005/0047739 | A1 | 3/2005 | Parker |
| 2005/0063425 | A1 | 3/2005 | Krastev |
| 2005/0073689 | A1 | 4/2005 | Pang |
| 2005/0169324 | A1 | 8/2005 | Ilday |
| 2006/0192969 | A1* | 8/2006 | Marks et al. ............ 356/451 |
| 2006/0268949 | A1 | 11/2006 | Gohle |
| 2007/0086713 | A1 | 4/2007 | Ingmar et al. |
| 2008/0069159 | A1 | 3/2008 | Adel |
| 2009/0213880 | A1 | 8/2009 | Ouchi |
| 2009/0296197 | A1 | 12/2009 | Holzwarth |
| 2010/0225897 | A1 | 9/2010 | Fermann |
| 2011/0019267 | A1 | 1/2011 | Li |
| 2011/0069309 | A1 | 3/2011 | Newbury |
| 2011/0141540 | A1 | 6/2011 | Hochrein |

FOREIGN PATENT DOCUMENTS

| | | |
|---|---|---|
| JP | 2009-130347 A | 6/2009 |
| WO | 00/55948 A1 | 9/2000 |
| WO | 0221644 A2 | 3/2002 |
| WO | 2004077142 A1 | 9/2004 |
| WO | 2007079342 A2 | 7/2007 |
| WO | 2009000079 A1 | 12/2008 |
| WO | 2009146671 A1 | 12/2009 |
| WO | 2010010437 A1 | 1/2010 |
| WO | 2010010438 A2 | 1/2010 |
| WO | 2010010444 A1 | 1/2010 |
| WO | 2010011875 A2 | 1/2010 |

OTHER PUBLICATIONS

Cundiff S. et al., Femtosecond combs linewidth due to pulse dynamics in mode-locked laser, ThD4, pp. 719-720 Lasers and Electro-Optics Society, 2007. LEOS 2007. The 20th Annual Meeting of the IEEE.

Diddam S. et al., An Optical Clock Based on a Single Trapped 199Hg+ Ion, Science 2001 293: 825-82.

Diddam S. et al., Direct RF of optical frequency measurements with a Femtosecond laser comb, IEEE Transactions on Intrumentation and Measurement, vol. 50, Is.2, p. 552-555 (Apr. 1, 2001).

E. Ebendorff-Heidepriem et al., Highly nonlinear bismuth-oxide-based glass holey fiber, presented at OFC 2004, Los Angeles, California, paper ThA4.

F. Fatemi, Frequency comb linewidth of an actively mode-locked fiber laser, Optical Society of America, Optics Letters, vol. 29, Issue 9, pp. 944-946 (2004).

T.W. Hansch et al., Laser frequency stabilization by polarization spectroscopy of a reflecting reference cavity, Optics Communications, vol. 35, Issue 3, Dec. 1980, pp. 441-444.

Hong et al., "Broad-spectrum frequency comb generation and carrier-envelope offset frequency measurement by second-harmonic generation of a mode-locked fiber laser", Optics Letters vol. 28, No. 17 p. 1516-18 Sep. 1, 2003.

R.J.Jones et al., Precision stabilization of femtosecond lasers to high-finesse optical cavities, Physical Review A 69, 051803(R) (2004).

D. Jones , Carrier-Evelope phase control of femtosecond mode locked lasers and direct optical frequency synthesis, D. Jones, Science Magazine (Nov. 7, 2003).

K. Kikuchi et al., Highly-nonlinear bismuth oxide-based glass fibers for all-optical signal processing, OFC 2002, post deadline paper.

L-S. Ma et al., A New Method to Determine the Absolute Mode Number of a Mode-Locked Femtosecond-Laser Comb Used for Absolute Optical Frequency Measurements IEEE Journal of Selected topics in quantum electronics, vol. 9 p. 1066 (2003).

J.J.McFerran et al., Low-noise synthesis of microwave signals from an optical source, Electron. Lett. 41, 36-37 (2005).

Minoshima et al., Study on cyclic errors in a distance measurement using a frequency comb generated by a mode-locked laser, Conference on Lasers and Electro-Optics 2004, paper CTuH6.

Minoshima, Femtosecond-comb distance meter; ultrahigh-resolution distance measurement using a mode-locked laser, THB (10), CLEO/Pacific Rim 2003—The 5th Pacific Rim Conference on Lasers and Electro-Optics THB (10), p. 394 Dec. 15-19, 2003.

T. Okuno et al., Silica-Based Functional Fibers with Enhanced Nonlinearity and Their Applications, IEEE J. Sel. Top. Quantum Electron. 5, 1385 (1999).

Rauschenberger et al., Control of the frequency comb from a mode-locked Erbium-doped fiber laser, Optics Express vol. 10 #24, p. 1404, Dec. 2, 2002.

T. R. Schibli et al: "Attosecond active synchronization of passively mode-locked lasers by balanced cross correlation," Optics Letters vol. 28, No. 11, p. 947 Jun. 2003.

C.X. Shi, A novel Er-doped fiber laser with adjustable pulse output experiment, Microwave and Optical Technology Letters vol. 12, No. 1, May 1966 pp. 26-29.

(56) References Cited

OTHER PUBLICATIONS

G. Stewart et al., A modelocking fiber laser system for Multi-Point Intra-cavity Gas Spectroscopy, Optical Fiber Sensors OFS 2002, p. 1-6 paper WA3.

Tamura, et al., Unidirectional ring resonators for self-starting passively mode-locked lasers, Optics Letters, vol. 18, No. 3, Feb. 1, 1993, pp. 220-222.

Tamura, et al., 77-fs pulse generation from a stretched-pulse mode-locked all fiber ring laser, Optics Letters, vol. 18, No. 13, Jul. 1, 1993, pp. 1080-1082.

Tauser et al, Amplified femtosecond pulses from an Er:fiber system: Nonlinear pulse shortening and self-referencing detection of the carrier-envelope phase evolution, Optics Express 11, 594-600 (2003).

H. R. Telle et al., Carrier-envelope offset phase control : a novel concept for absolute frequency measurement and ultrashort pulse generation, Appl. Phys. Lett., B69, 327 332 (1999).

D. Von Der Linde, Characterization of the noise in continuously operating mode-locked lasers, Appl. Phys. B. vol. B 39 p. 201-217 (1986).

Washburn, et al., A Phase Locked Frequency comb from an all-fibre supercontinuum source, The 29th European Conference on Optical Communications, Sep. 22-24, 2003, Rimini, Italy (2003).

Apolonski A., et al., Controlling the Phase Evolution of Few-Cycle Light Pulses, Physical Review Letters, Jul. 24, 2000, vol. 85, No. 4, pp. 740-743.

Cundiff S., Colloquium: Femtosecond optical frequency combs, Review of Modern Physics, vol. 75, p. 325-342 (Jan. 1, 2003).

Bhushan A. S. et al., 150 Gsample/s wavelength division sampler with time-stretched output, Electron. Lett., vol. 34, No. 5, pp. 474475, 1998.

P. Giaccari et. al., Active Fourier-transform spectroscopy combining the direct RF beating of two fiber-based mode-locked lasers with a novel referencing method Optics Express vol. 16 No. 6, p. 4347 Mar. 2008.

P. Hamm et al., The two-dimensional IR nonlinear spectroscopy of a cyclic penta-peptide in relation to its three-dimensional structure, Prov. Nat. Acad. Sci. 96, p. 2036, 1999.

P. C. D. Hobbs Building Electro-Optical Systems, John Wiley&Sons (2000) Fig. 10.4 p. 332.

T. Hoehrein et. al., Optical Sampling by LaserCavity Tuning, Optics Express vol. 18, No. 2, Jan. 18, 2010 p. 1613.

R. M. Hochstrasser et al., Two-dimensional spectroscopy at infrared and optical frequencies, in Proceedings of the National Academy of Sciences, vol. 104, pp. 14190 (2007).

K. Holman et al., Precise frequency transfer through a fiber network by use of 1.5-m mode-locked sources, Opt. Lett., vol. 29, pp. 1554 1556 (2004).

K. Holman et al., Remote transfer of a high-stability and ultralow-jitter timing signal Optics Letters, vol. 30, Iss. 10, pp. 12251227 (2005).

R. J. Jones et. al., Stabilization of Femtosecond lasers for Optical Frequency Metrology and Direct Optical to Radio Frequency Systhesis, Physical Review Letters vol. 86, No. 15, Apr. 2001 p. 3288-91.

F. Keilmann et .al., Time domain mid-infrared frequency-comb spectrometer, Optics Letters vol. 29, No. 13, 2004 , p. 1542.

J. Kim et al., Long-term femtosecond timing link stabilization using a single-crystal balanced cross-correlator, Optics Letters, 32, pp. 1044-1046 (2007).

J. Mandon et.al., Fourier transform Spectroscopy with a laser frequency comb, Nature Photonics vol. 3, p. 99 Feb. 2009.

N. Newbury et. al.; Low-noise fiber-laser frequency combs JOSA B vol. 24, No. 8, Aug. 2007 p. 1756-1770.

S. A. Roy et al., Hybrid sampling approach for imaging Fourier-transform spectrometry, Applied Optics, vol. 46, pp. 8482 8487 (2007).

Schlup et al., Sensitive and selective detection of low-frequency vibrational modes through a phase-shifting Fourier-Transform spectroscopy, IEEE J. Quantum Electronics, vol. 45, No. 7, pp. 777, 2009.

T. Sizer Increase in laser repetition rate by spectral selection, IEEE J. Quantum Electronics, vol. 25, pp. 97 103 (1989.

J. Stenger et al., Ultraprecise Measurement of Optical Frequency Ratios, Phys. Rev. Lett., vol. 88, pp. 073601-1-073601-4, (2002).

T. Yasui et. al., Terahertz frequency comb by multifrequency-heterodyning photoconductive detection for high-accuracy, high-resolution terahertz spectroscopy Applied Physics Letters vol. 88, 241104 (2006).

A. Bartels et. al., Ultrafast time-domain spectroscopy based on high-speed asynchronous optical sampling, Rev. Sci. Instruments vol. 78 No. 3, Mar. 2007, p. 35107.

I. Coddington et .al., Coherent Multiheterodyne Spectroscopy Using Stabilized Optical Frequency Combs Physical Review Letters vol. 100, 013902, 2008.

K. Holman "Detailed studies and control of intensity-related dynamics of femtosecond frequency combs from mode-locked Ti: Sapphire Lasers", IEEE Journal of Selected Topics in Quantum Electronics, vol. 9, Is. 4, p. 1018-1024 (Jul. 1, 2003).

S. Bartaline et al., Frequency metrology with quantum cascade lasers, Proceedings of SPIE, vol. 7222, pp. 72220C1-1 72220C1-10 (2009).

P. Delhaye et al., Optical frequency comb generation from a monolithic microresonator, Nature, vol. 450, pp. 1214 1217 (2007).

S. Diddams et al., A phase and frequency controlled femtosecond laser for metrology and single-cycle nonlinear optics ASSL 2000 p. 631-633.

S. Diddams et al., Molecular fingerprinting with the resolved modes of a femtosecond laser frequency comb, Nature, vol. 445, pp. 627 (2007).

C.H. Li et al., A laser frequency comb that enables radial velocity measurements with a precision of 1 cm/s, Nature, vol. 452, pp. 610 (2008).

J. Millo et al., Ultra-low-noise microwave extraction from fiber-based optical frequency comb, Opt. Lett., vol. 34, pp. 3707 (2009).

Poppe et al., "Few-cycle optical waveform synthesis", Appl. Phys. B Lasers Opt. 72,373-376 2001.

T. Udem et al., Optical frequency metrology, Nature, vol. 416, pp. 233 (2002).

Xu et al., Route to phase control of ultrashort light pulses, Optics Letters, vol. 21, Issue 24, pp. 2008-2010 (1996).

Translation of Japanese Office Action, (Notice of Reasons or Rejection), dated Jun. 10, 2014, filed Dec. 10, 2014, Application No. 2012-532291.

Japanese Office Action (Notice of Reasons for Rejection); dated Jun. 10, 2014 (English Translation received Aug. 5, 2014); Application No. 2012-532291.

J. M. Dudley et al., 'Supercontinuum generation in photonic crystal fiber,' Reviews of Modern Physics, vol. 78, Oct.-Dec. 2006.

* cited by examiner

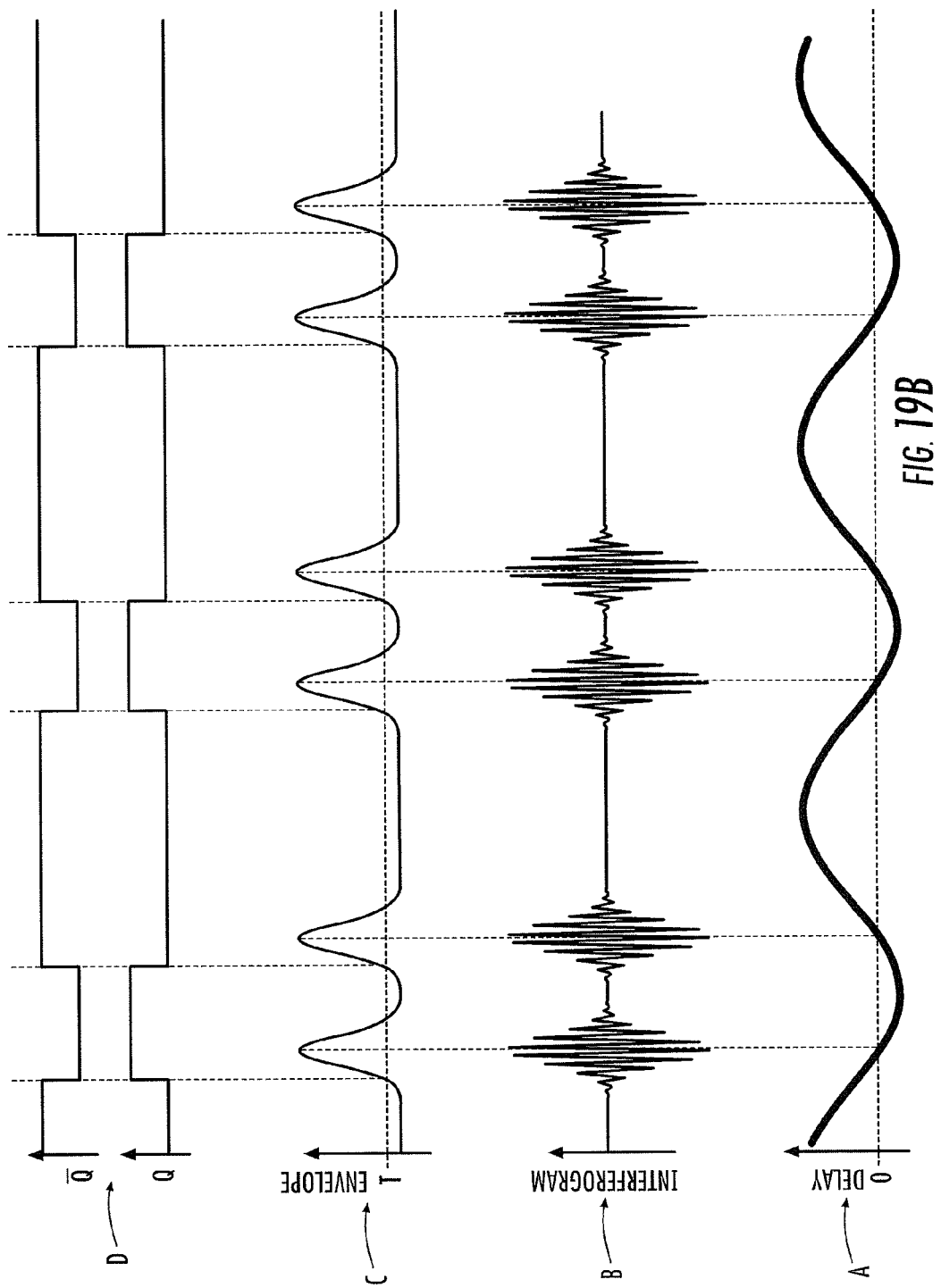

OPTICAL SIGNAL PROCESSING WITH MODELOCKED LASERS

CROSS REFERENCE TO RELATED APPLICATIONS

This application claims priority to U.S. Provisional Patent Application No. 61/364,545, filed Jul. 15, 2010, entitled "Optical signal processing with modelocked lasers". The contents of Ser. No. 61/364,545 are hereby incorporated by reference in their entirety. This application claims priority to U.S. Provisional Patent Application No. 61/301,722, filed Feb. 5, 2010, entitled "Optical signal processing with modelocked lasers". The contents of Ser. No. 61/301,722 are hereby incorporated by reference in their entirety. This application claims priority to U.S. Provisional Patent Application No. 61/286,179, filed Dec. 14, 2009, entitled "Optical scanning and imaging systems based on dual pulsed laser systems". The contents of Ser. No. 61/286,179 are hereby incorporated by reference in their entirety. This application claims priority to U.S. Provisional Patent Application No. 61/248,207, filed Oct. 2, 2009, entitled "Optical signal processing with modelocked lasers". The contents of Ser. No. 61/248,207 are hereby incorporated by reference in their entirety.

This application is related to U.S. patent application Ser. No. 12/399,435, filed Mar. 6, 2009, entitled "Optical scanning and imaging systems based on dual pulsed laser systems", and hereinafter referred to as '435. The contents of Ser. No. 12/399,435 are hereby incorporated by reference in their entirety.

This application is related to U.S. patent application Ser. No. 11/546,998, filed Oct. 13, 2006, entitled "Laser based frequency standards and their application", and hereinafter referred to as '998. The contents of Ser. No. 11/546,998 are hereby incorporated by reference in their entirety. '998 was published as U.S. Patent Application Pub. No. 2007/0086713 on Apr. 19, 2007.

This application is related to U.S. patent application Ser. No. 11/372,859, filed Mar. 10, 2006, entitled "Pulsed laser source", and hereinafter referred to as '859. The contents of Ser. No. 11/372,859 are hereby incorporated by reference in their entirety. '859 was published as U.S. Patent Application Pub. No. 2006/0198398 on Sep. 7, 2006.

BACKGROUND OF THE INVENTION

1. Field of the Invention

The invention relates to the application of optical signal processing to mode locked lasers for precision sensing, sampling and spectroscopy.

2. Description of Related Art

Mode locked lasers and frequency comb lasers have provided for advancements in spectroscopy and precision sensing. A mode locked laser was recently combined with a conventional Fourier transform spectrometer (FTS) to obtain an improved signal/noise ratio for spectral absorption measurements (J. Mandon et al., 'Fourier transform spectroscopy with a laser frequency comb', in Nature Photonics, vol. 3, pp. 99-102, 2009) and N. Picque' et al., International Patent Application, Publication WO 2010/010437. The use of a frequency comb laser for spectroscopy was suggested by Haensch et al. in U.S. Pat. No. 7,203,402.

As discussed in '435, 'in the state of the art, frequency comb lasers can be understood as constituting a sub-class of mode locked lasers. Both mode locked lasers and frequency comb lasers produce a train of output pulses at a certain repetition rate $f_{rep}$ with a corresponding output frequency spectrum, which can be characterized as a line spectrum with individual frequency lines $$f = f_{ceo} + m f_{rep},$$

where m is an integer and $f_{ceo}$ is the carrier envelope offset frequency. The integer m is also referred to as the comb line order. However, in contrast to mode locked lasers, frequency comb lasers require precise control of the repetition rate and carrier envelope offset frequency.

Indeed, a difficulty limiting the widespread use of frequency comb lasers is precision optical phase-locking of the individual comb lines to at least two external reference frequencies in order to obtain a stable frequency comb. However, at least for optical metrology, frequency measurements can be performed without stabilization of individual comb lines by the use of a modelocked laser as a transfer oscillator (J. Stenger et al., Phys. Rev. Lett., vol. 7, pp. 073601-1-073601-4, (2002)). Using modelocked lasers as transfer oscillators, frequency ratios or frequency differences between two reference frequencies located in widely separated regions of the optical spectrum (limited only by the spectral extent of the spectral coverage of the modelocked lasers) can be precisely measured. This technique, as applied to the measurement of difference frequencies when using a cw laser (instead of a mode locked laser) as a transfer laser is well known in metrology (C. O. Weiss et al., in 'Frequency measurement and control, advanced techniques and future trends', vol. 79, pp. 215-247 (2000). The cw transfer oscillator is sometimes also referred to as reference oscillator.

As also shown in '435, cw reference lasers can be used to effectively stabilize the differences between the carrier envelope offset frequencies of two modelocked lasers. This information can then be used for spectral calibration of a FTS for spectral absorption measurements constructed from the two modelocked lasers with a resolution limit corresponding approximately to the repetition rate of the modelocked lasers. As described in '435, such dual modelocked lasers are referred to as coherent dual scanning lasers or CDSLs. Moreover, CDSLs based on high repetition rates allow for high scan rates which are beneficial for rapid signal acquisition. CDSLs based on fiber supercontinuum sources further allow very broad spectral coverage for an FTS and other applications.

More generally, two narrow linewidth cw reference lasers can be used to track the difference between the carrier envelope offset frequencies and repetition rates of two mode locked lasers, as disclosed by P. Giacarri et al., 'Referencing of the beating spectra of frequency combs' (International Patent Application, Publication WO 2009/000079) without the need for carrier envelope offset frequency control. However, when applied to Fourier transform absorption spectroscopy, the resolution of this scheme is also limited to the repetition rate of the mode locked lasers, assuming for example that a reference laser is located in between two comb lines and the absolute frequency of the reference laser or the absolute order m of the comb lines is not known. As a result, relatively low repetition rate lasers are implemented which leads to slow data acquisition rates.

In another scheme the beat signal between two comb lines from two separate comb lasers can be directly measured via the implementation of a cw transfer oscillator. Repetition rate fluctuations between the two comb lasers can then be recorded and these recorded repetition rate fluctuations can then be used to simultaneously correct an interferogram between the two comb lasers via implementing a new sampling grid with equidistant optical path length differences (G.

Guelachvili et al., World patent application, WO 2010/010444). However, this scheme ideally also uses measurements of the carrier-envelope offset frequencies of the two comb lasers or alternatively implements a second cw laser with a different frequency to which two other comb lines are locked.

Hertz-level resolution in a FTS has been achieved using two frequency comb lasers which are phase locked to two cw lasers which were in turn locked to two high finesse reference cavities as discussed in I. Coddington et al., 'Coherent multiheterodyne spectroscopy using stabilized comb sources', Phys. Rev. Lett., vol. 100, pp. 013902 (2008); henceforth 'Coddington'. However, such a scheme requires at least 4 phase locked loops for locking of the frequency comb lasers to the two cw optical clock lasers, plus additional phase locked loops for stabilization of the cw lasers to the reference cavities. Moreover, the achieved Hz level resolution is generally not required in real-world optical spectroscopy, where Doppler broadened absorption lines of line width $\Delta v \approx 5 \times 10^{-7} v_x$ at a frequency of $v_x$ are typically encountered. For example, in the visible spectral region $\Delta v \approx 300$ MHz.

A further need exists for a simple FTS scheme based on CDSLs which allows high scan rates as well as high spectral resolution. Moreover, there is still a need for a laser based FTS scheme that can measure emission as well as absorption spectra.

SUMMARY OF THE INVENTION

Rapidly scanning CDSLs are disclosed based on mode locked lasers for various applications, for example, high resolution, high sensitivity FTS and micro-spectroscopy, optical imaging, sampling and light detection and ranging (LIDAR).

Various high resolution CDSL embodiments include first and second mode locked oscillators operated at slightly different repetition rates, each mode locked oscillator having a carrier envelope offset frequency. Outputs of the first and second mode locked oscillators, in combination with outputs from two reference lasers, are used to generate signals for stabilizing differences between both the carrier envelope offset frequencies and differences between the repetition rates of the two mode locked oscillators. In some embodiments the carrier envelope offset frequency of at least one oscillator may also be derived from the signals, resulting in a resolution corresponding to at least the bandwidth of the reference lasers and further allowing for Hertz level frequency resolution.

Various high resolution CDSLs are useable in systems for phase, absorption, emission and/or spectral measurement. Various embodiments provide high resolution FTS by utilizing a combination of optical phase-locking with optical referencing. In at least one embodiment the difference frequencies of two next neighbor comb lines from two mode locked lasers are phase-locked with at least two phase-locked loops using two cw reference lasers. Alternatively, frequency locking schemes can also be implemented. Tracking of the beat frequencies of the two cw reference lasers with the individual comb lines further allows absolute frequency calibration of the FTS. Various embodiments provide high resolution FTS by recording multiple adjacent interferograms, which increases the resolution of a FTS proportional to the signal acquisition time.

The resolution of such CDSLs can further be optimized by using the phase error output of the phase-locked loops to compute corrections for high resolution FTS. In general the phase error output of phase locked loops or frequency locks can be used to produce correction signals to various frequency parameters defining the operation of the mode locked lasers.

Various embodiments provide high sensitivity, low noise FTS with broad spectral coverage by implementing frequency conversion schemes to expand spectral coverage, and dual balanced detection schemes for noise suppression. In at least one embodiment such a dual balanced detection scheme can utilize the interference of two mode locked lasers, which are combined at a beam-splitter. Alternatively, the two mode-locked lasers can be amplified and spectrally broadened along two orthogonal polarization axes in an optical fiber system and subsequently combined via a beam-splitter.

Various embodiments provide high sensitivity FTS by the adaptation of enhancement cavities incorporated into the beam path of one mode locked laser. Locking to the enhancement cavities can be performed by frequency shifting of the laser spectra with appropriate optical frequency shifters or by tuning the cavity.

FTS can be implemented for the measurement of phase, absorption and emission spectra of optical samples located inside the beam path of the two mode locked lasers.

Emission spectral measurements can be used for the measurement of spontaneous and stimulated Raman emission spectra from optical samples, enhancement of Raman emission can further be implemented for improved signal/noise ratios and optical imaging and optical scanning can be implemented for the measurement of spatially resolved Raman spectra.

CDLS can also be used for signal characterization via linear optical sampling.

CDLS can further be used to measure the phase response of a test sample to a strong pump pulse in a pump probe configuration.

CDLS can further be used for two and multi-dimensional emission and absorption spectroscopy of a test sample. CDSLs can further be implemented in optical coherence tomography by measurement of the time dependent reflection from a sample, where preferably the measurement is performed at the fundamental interferometric beat frequency of the two mode locked lasers.

Depth resolved imaging can also be performed in the THz domain by using the two mode locked lasers in a pump probe arrangement.

In at least one embodiment the difference in carrier envelope offset frequencies and repetition rates of a CDSL is controlled by locking two next neighbor comb lines from two mode locked lasers to at least one cw reference laser.

In at least one embodiment the resolution of a FTS based on CDSL is increased proportional to the signal acquisition time by minimizing fluctuations of the effective scan rate during the signal acquisition time.

In at least one embodiment dual balanced detection improves the signal/noise ratio of a FTS.

In at least one embodiment the sensitivity of a FTS based on CDSL is increased with the use of an external cavity.

In at least one embodiment phase and absorption spectra are measured using an FTS based on a CDSL.

Embodiments may be adapted for OCT (optical coherence tomography), THz imaging, or similar applications. In various embodiments a CDSL is integrated with existing FTS equipment, which may include one or more of positioning equipment for samples to be probed, detection equipment, and signal processing equipment which may include digital and/or analog signal processors, computers, and/or various signal processing software algorithms.

In some embodiments, in order to reduce the cost, an effective CDSL may be constructed with only one laser.

At least one embodiment includes a coherent scanning laser system (CSL) for generating pulse pairs with a time varying time delay. The system includes an optical source that generates optical pulses at a time-varying repetition rate, and a repetition rate modulator to modulate the repetition rate at a modulation rate. The source generates an output that includes the pulse pairs. The system also includes an optical reference for generating a reference signal for measurement of at least the time delay between the two pulses of the pulse pair as a function of time.

BRIEF DESCRIPTION OF THE DRAWINGS

FIG. 19B is a series of plots illustrating various signals for centering the zero-delay point during repetition rate dithering in relation to the actual cavity length modulation.

DETAILED DESCRIPTION OF THE INVENTION

Some examples of CDSL systems and applications are disclosed below. Implementations providing for one or more of high resolution, high acquisition rate, high sensitivity, low-noise, and a high-level of integration are described. Non-linear spectral generation and various implementations for phase-control lead to stable output signals in the near-IR range, thereby providing benefits for IR absorption and emission spectroscopy, THz imaging and ranging applications.

Figure 1:
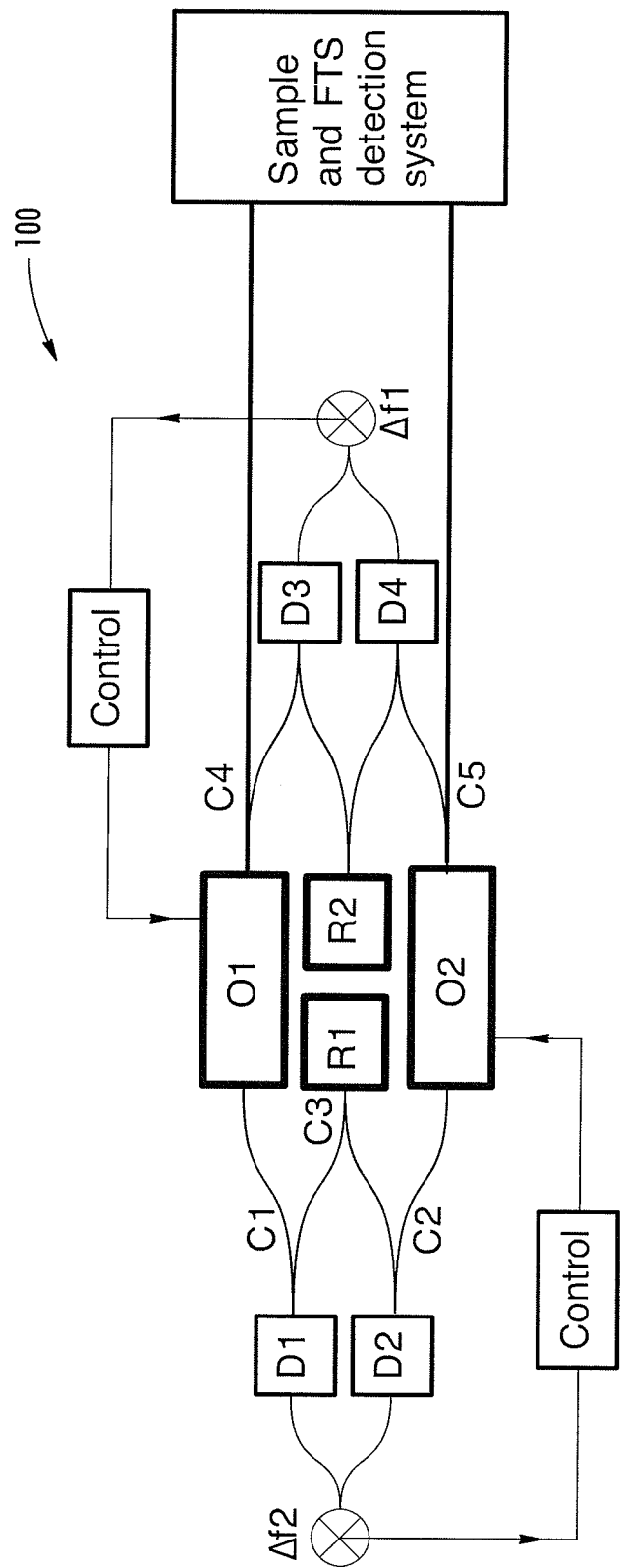
FIG. 1 is a diagram schematically illustrating high resolution FTS based on a CDSL.

FIG. 1 schematically illustrates a coherent dual scanning laser system 100 (CDSL) according to an embodiment for Fourier transform absorption spectroscopy. In this example, output of CDSL 100 is directed to a sample to be measured. A Fourier transform spectrometer (FTS) probes a physical property of the sample using spectral information in the emission envelope of the CDSL.

As shown in FIG. 1, CDSL 100 comprises two mode locked lasers (oscillator O1 and oscillator O2) and two cw reference lasers (R1 and R2). Each oscillator produces outputs that are combined with outputs from each of the reference lasers, which may be CW lasers. FIG. 1B schematically illustrates a portion of the spectra 110, 120 corresponding to outputs from O1 and O2, respectively. O1 and O2 have slightly different repetition rates $f_{r1}$, $f_{r2}$, and the frequency lines of O1 and O2 are separated by the respective repetition rates. Certain frequency lines of O1, O2 are spaced apart from immediately adjacent frequencies $f_x$, $f_y$ of the cw reference lasers as shown. By way of example, beat frequencies $f_{b1}$, $f_{b2}$, $f_{b3}$, and $f_{b4}$, and difference frequencies $\Delta f_2$ and $\Delta f_1$ thereof, are derived from O1 and O2 and adjacent frequency lines of R1 and R2. The signals are detected with photodetectors so as to monitor and/or stabilize the CDSL. A control system, which may include a phase locked loop and analog and/or digital signal processors, may be used to monitor and/or stabilize the CDSL.

As illustrated in the example of FIG. 1, the outputs of oscillators O1,O2 and cw reference laser R1 are combined via two fiber optic couplers C1 and C2, respectively. An additional fiber optic coupler C3 splits the output of reference laser R1 and directs the R1 output to couplers C1 and C2. The beat frequency between a frequency line of oscillator O1 and cw laser R1, $f_{b1}$, is detected with detector D1. The beat frequency between a frequency line of oscillator O2 and cw laser R1, $f_{b2}$, is detected with detector D2. The outputs of detectors D1 and D2 are further mixed and low pass frequency filtered to produce a beat frequency signal, $\Delta f_2 = f_{b1} - f_{b2}$, corresponding to the difference between beat frequencies $f_{b1}$ and $f_{b2}$. $\Delta f_2$ can further be stabilized by appropriately varying the cavity length of O2 via phase locking of $\Delta f_2$ to an external RF reference (not shown). Here analog or digital phase locked loops can be implemented. When using digital phase locked loops, the beat frequencies $f_{b1}$ to $f_{b4}$ are also digitized. Alternatively $f_{b1}$ and $f_{b2}$ can both be locked individually to external RF references using for example cavity length or oscillator pump power control of one or the other oscillator, which also stabilizes $\Delta f_2$. Locking of a cw reference laser to two mode locked lasers for the construction of a CDSL was for example discussed in '435.

Figure 1A:
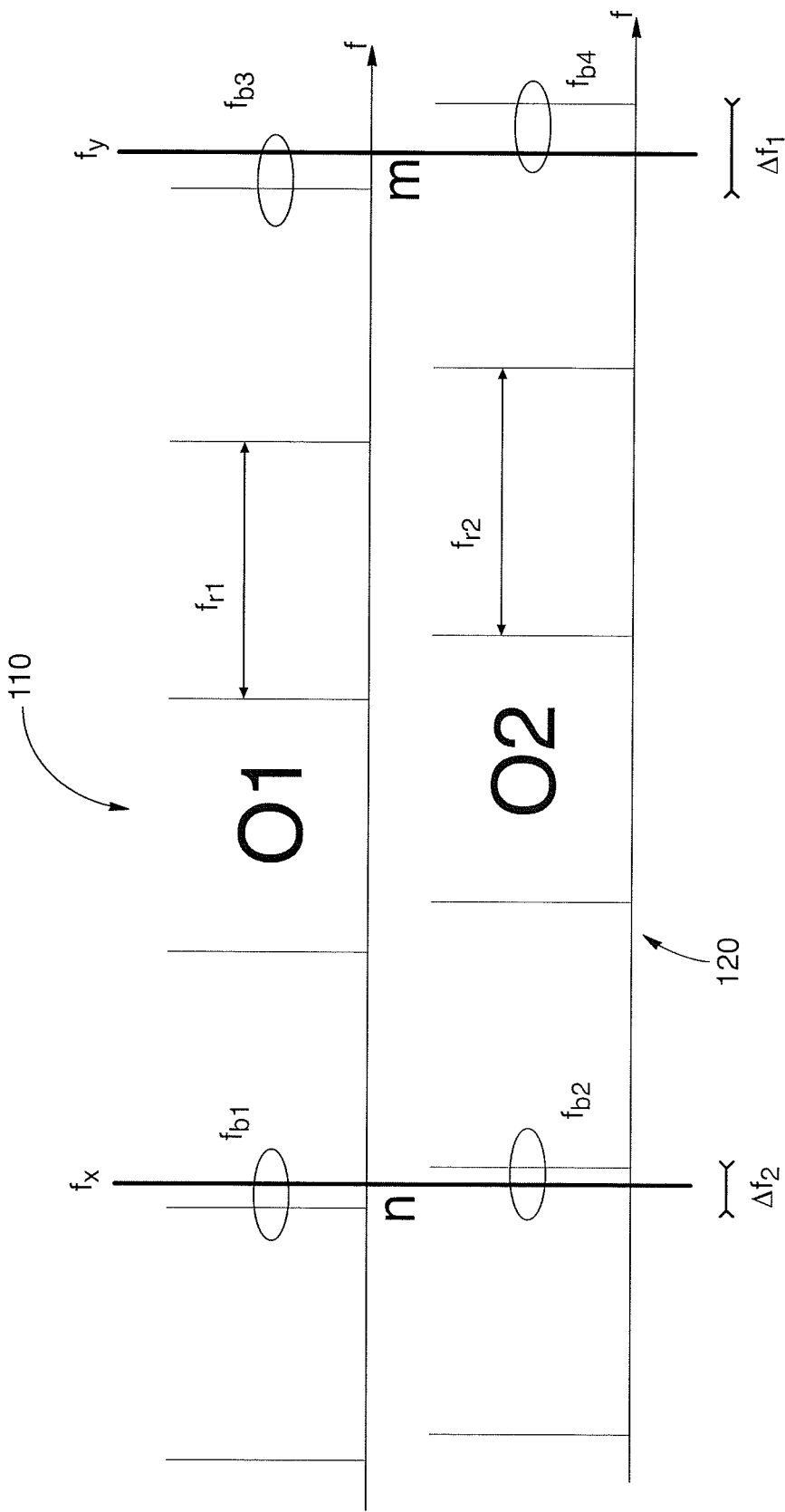
FIG. 1A schematically illustrates a portion of the spectra of two mode locked lasers and two reference oscillators, and beat frequencies derived therefrom for monitoring and/or stabilizing a CDSL.
Figure 1B:
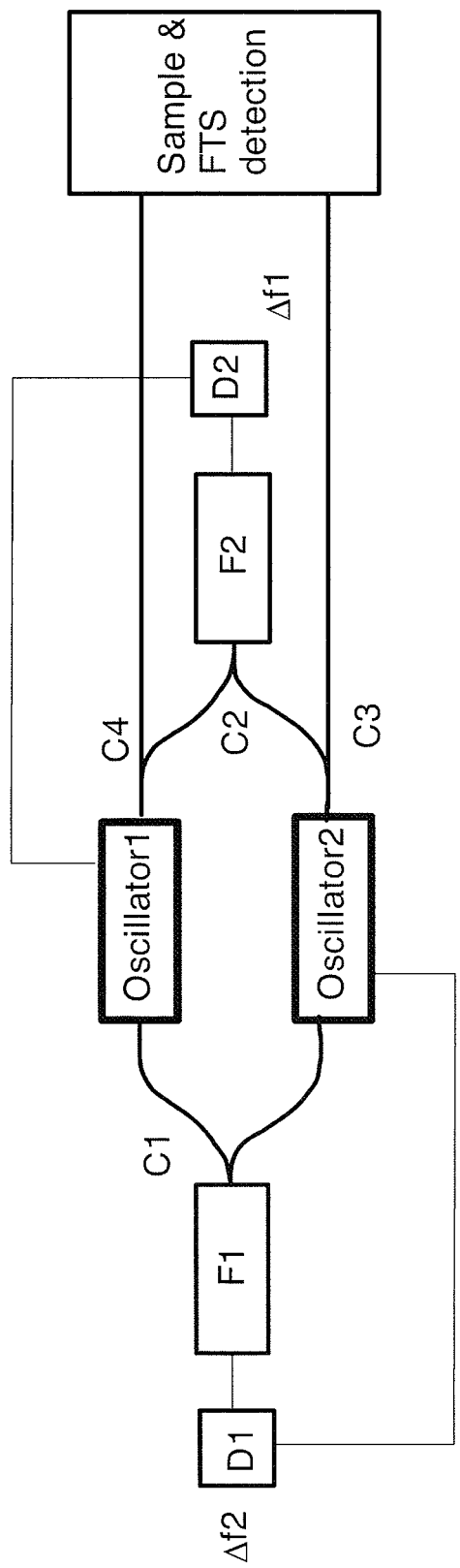
FIG. 1B schematically illustrates an arrangement for a high resolution FTS based on a CDSL.

In FIG. 1A, beat signals can be observed when the comb lines are on either side of $f_x$ and $f_y$ respectively. This ambiguity can be eliminated by the use of optical single side-band (SSB) mixers, which suppress the beat signals on one side of $f_x$ and $f_y$. For example an optical SSB mixer can suppress $f_{b1}$ and $f_{b3}$ in FIG. 1A, while passing $f_{b2}$ and $f_{b4}$. In order to observe the beat signals $f_{b1}$ and $f_{b3}$, the comb lines have thus to be shifted to be on the right side of $f_x$ and $f_y$ respectively. SSB mixers simplify the required locking electronics and the interpretation of the observed beat signals.

Figure 10:
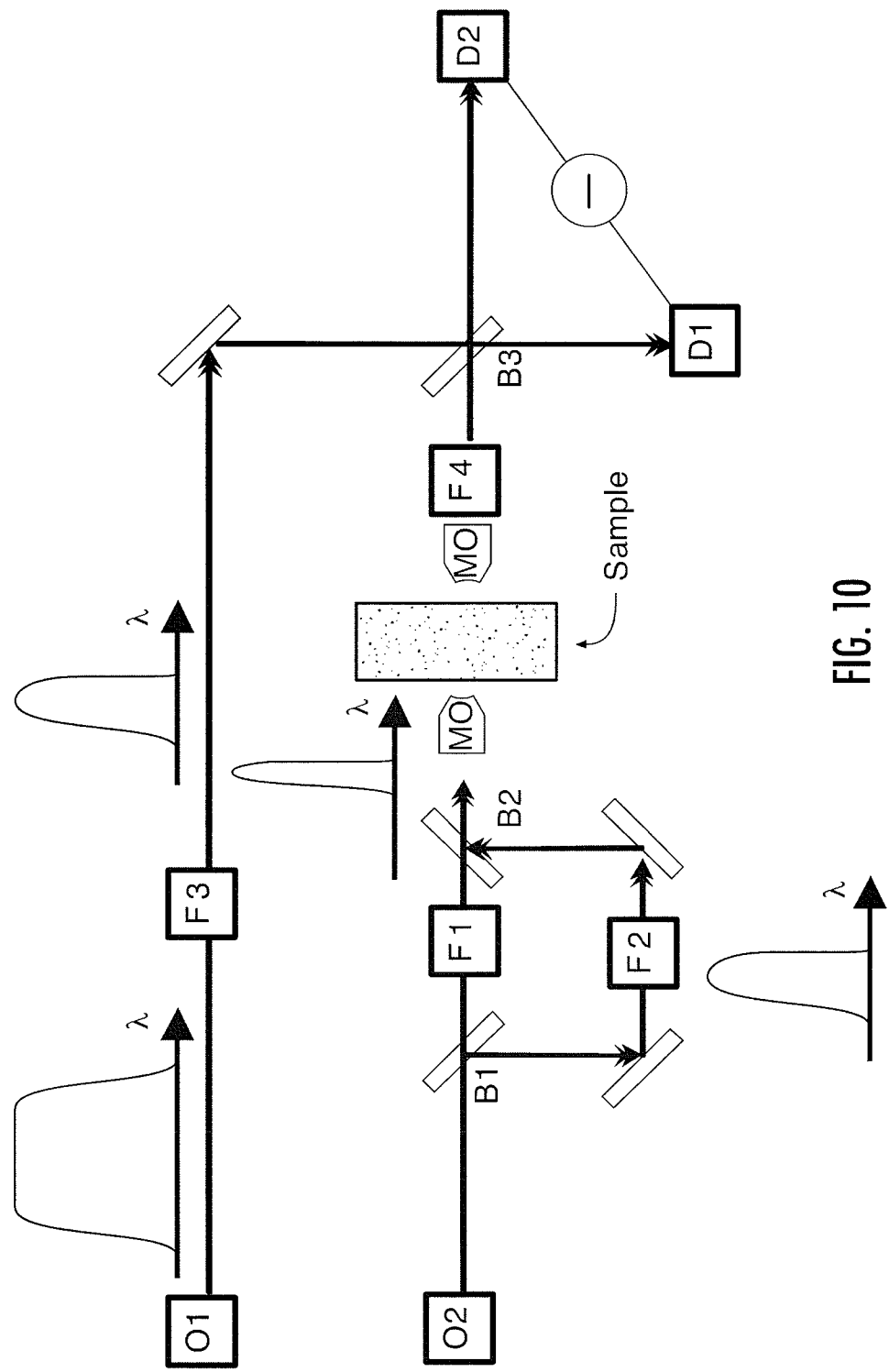
FIG. 10 is a schematic diagram of an arrangement for coherent anti-Stokes Raman spectroscopy.

Optical SSB mixers are well known in the state of the art and are, for example, shown in FIG. 10.4 of 'Building Electro-Optical Systems' by P. C. D. Hobbs, John Wiley&Sons (2000) and are not further described here. The incorporation of SSB mixers in FIG. 1 requires the substitution of each of the four detectors D1-D4 in FIG. 1 with a set of two pairs of balanced detectors (resulting in a total of 8 balanced detector pairs) for in-phase detection and quadrature detection of the respective beat signals.

Various schemes for cavity length control of mode locked lasers were discussed in '435. A similar arrangement using reference oscillator R2, oscillators O1 and O2, and detectors D3 and D4 generates beat frequencies $f_{b3}$, $f_{b4}$ and $\Delta f_1$, where locking of $f_{b3}$ and $f_{b4}$ to an external RF reference can also be employed for the stabilization of $\Delta f_1$. Fiber optic beam paths and couplers provide for a high level of integration. In some embodiments free-space beam paths and beamsplitters may be implemented, alone or in combination with fiber technology. Preferably mode locked fiber lasers are implemented as oscillators O1 and O2, although solid-state laser oscillators and diode lasers may be used in various embodiments, alone or in combination with fiber oscillators.

Figure 2:
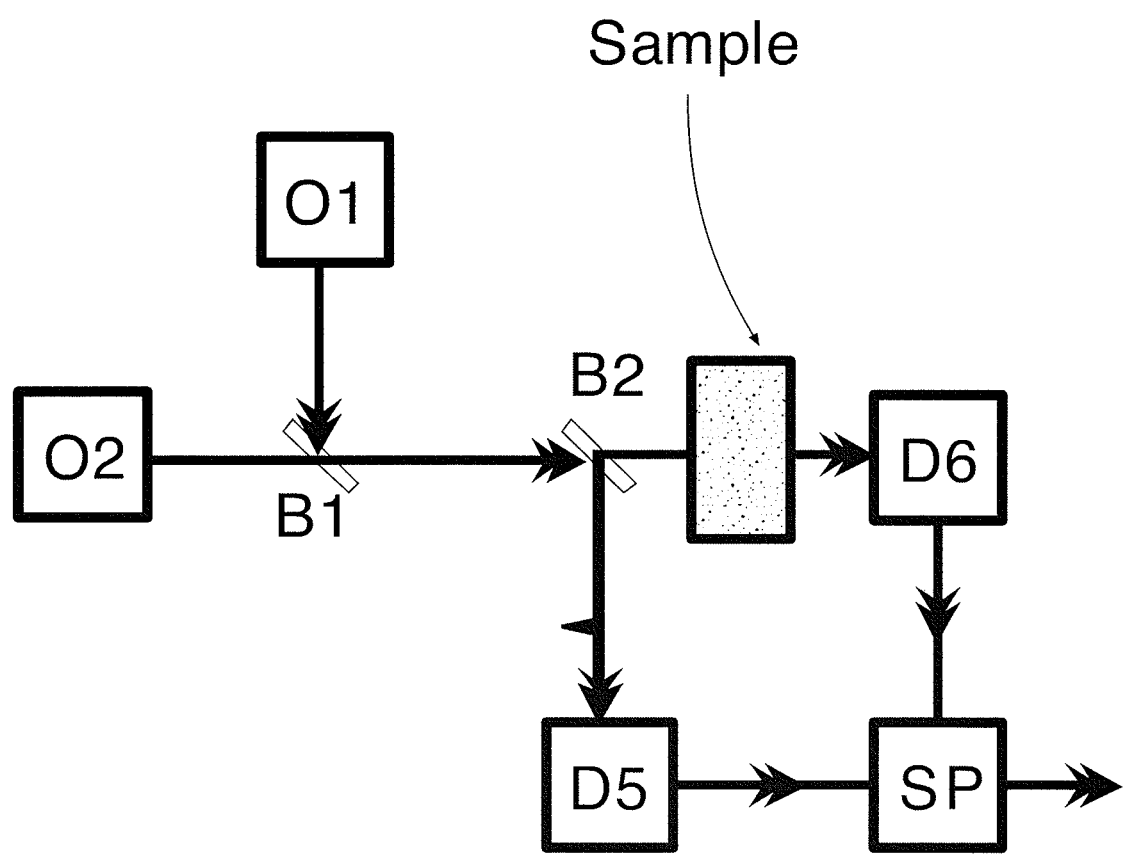
FIG. 2 is a schematic representation of sample and detector locations for sample absorption measurement with a CDSL.

A sample and FTS detection unit as illustrated in FIG. 1 is shown in more detail in the example of FIG. 2. In the arrangement of FIG. 2, the outputs of the two oscillators O1, O2 are combined via beamsplitter B1 (or an equivalent fiber optic coupler) in order to construct a FTS for absorption spectroscopy. A second beam splitter B2 allows for the detection of a reference spectrum via detector D5. The absorption spectrum of a sample inserted in front of detector D6 is measured using the output of detector D6. Signal processing equipment, SP, may be utilized in the FTS to condition signals from the detectors and process the information obtained from the detectors. Schemes for obtaining the absorption spectrum via a FTS based on a CDSL were also discussed in '435.

The relation between the frequency output of oscillators O1 and O2 and beat signals $f_{b1}$ to $f_{b4}$ as well as the optical reference frequencies $f_x$, $f_y$ of reference lasers R1 and R2 respectively can then be written as:

$$nf_{rep} + f_{ceo1} = f_x + f_{b1} \tag{1}$$

$$n(f_{rep} + \delta) + f_{ceo2} = f_x + f_{b2}, \tag{2}$$

$$mf_{rep} + f_{ceo1} = f_y + f_{b3} \tag{3}$$

$$m(f_{rep} + \delta) + f_{ceo2} = f_y + f_{b4}, \tag{4}$$

where $f_{rep}$, $f_{rep} + \delta$ and $f_{ceo1}$, $f_{ceo2}$ are the repetition rates and carrier envelope offset frequencies of the two mode locked lasers respectively, n and m are integers, and with an assumption the optical references $f_x$, $f_y$ are beating with frequency lines from the two mode locked lasers of the same order n and m respectively. It can then be easily shown that the difference in repetition rates $\delta$ and the difference in carrier envelope offset frequencies $\Delta f_{ceo}$ between the two mode locked lasers is given by $$\delta = \frac{\Delta f_2 - \Delta f_1}{n - m} \tag{5}$$

$$\Delta f_{ceo} = \frac{n \Delta f_1 - m \Delta f_2}{n - m} \tag{6}$$

Thus stabilization of $\Delta f_1$ and $\Delta f_2$ in turn stabilizes $\delta$ and $\Delta f_{ceo}$. As explained in '435, from a knowledge of $\delta$ and $\Delta f_{ceo}$ (and the laser repetition rate) the calibration of the frequency scale of a FTS based on CDSL can be performed. However, the obtainable resolution is then comparable to the repetition rate of the mode locked lasers. The comb line orders, n and m, can be obtained for example via absolute frequency measurements using a separate comb laser. As shown in '435, in order to obtain improved resolution, either $f_{ceo1}$ or $f_{ceo2}$ are measured. In at least one embodiment this can be performed with an f-2f interferometer. Alternatively, $f_{ceo1}$ can be obtained from $$f_{ceo1} = \frac{n(f_y + f_{b3}) - m(f_x + f_{b1})}{n - m}. \tag{7}$$

A similar expression can also be written down for $f_{ceo2}$. Hence $f_{ceo1}$ can be obtained from recording $f_{b3}$ and $f_{b1}$ in addition to stabilizing $\Delta f_1$ and $\Delta f_2$. For an actual wavelength calibration $f_{ceo1}$ can be recorded during the acquisition time $\tau$ of an interferogram and the interferogram can then be multiplied with a phase correction term $$O_{opt} = \exp\left[-i\left(\frac{\delta}{f_{rep}}\right) \int_0^\tau f_{ceo1}(t)\,dt\right]. \tag{8}$$

A Fourier transform of the corrected interferogram then yields the RF spectrum, which can be related to the optical spectrum via a conversion factor $$f_{opt} = [f_{rf} - \Delta f_{ceo}] f_{rep} / \delta \tag{9}$$

as also explained in '435. Alternatively, the usable signal acquisition time in FTS can be regarded as being limited by the coherence time of the cw references. In various embodiments it is beneficial to lock $f_{rep}$ to an external frequency reference, which can for example be done via modulating the pump current to one of the mode locked lasers. Alternatively, $f_{rep}$ can be recorded and an additional phase correction term can be added to eq. (8). Because the cw lasers can be locked to optical clocks and coherence times of the order of seconds can be achieved, Hertz level frequency resolution can be achieved. Thus, frequency resolution very much smaller than the repetition rate of the mode locked lasers is obtainable.

Generally, $\Delta f_1$ and $\Delta f_2$ can be stabilized by locking optical beat signals generated by overlap between individual comb lines and a cw reference laser to external RF references. Alternatively, $\Delta f_1$ and $\Delta f_2$ can be stabilized by using cw reference lasers as transfer oscillators and locking the difference frequency of two comb lines from two different modelocked lasers to external RF references. Any combination of these two methods is also possible.

$\Delta f_1$ and $\Delta f_2$ can further be directly measured and stabilized by isolating two individual comb lines from the two comb lasers via optical filtering and measuring the resulting beat signal. Optical filters can, for example, be conveniently constructed from fiber Bragg gratings or Fabry-Perot etalons or a combination of both. An example of a scheme for locking $\Delta f_1$ and $\Delta f_2$ with optical filters is shown in FIG. 1B. Here F1 and F2 represent two optical filter arrangements. For example, F1 can comprise a fiber Bragg grating operated in reflection in conjunction with an optical circulator and a high resolution Fabry-Perot etalon. The free spectral range of the etalon is then selected to be narrower than the bandwidth of the fiber Bragg grating. Such an arrangement is not separately shown. The remaining components were described with respect to FIG. 1. Optical amplifiers can further be inserted before the optical filters in order to increase the signal to noise ratio for the $\Delta f_1$ and $\Delta f_2$ measurements. For the best resolution the overall bandwidth of the optical filters is comparable to or smaller than the repetition rate of the two comb lasers; however, larger filter bandwidths can also be implemented if lower spectral resolution is sufficient.

The details of phase-locking techniques are well known in the art and not described here. Phase locking methods generally use a phase/frequency detector which can be implemented via analog electronics as a frequency mixer or via digital electronics, digital frequency counters or via digital signal processing. The phase/frequency-detector produces an output proportional to the phase/frequency difference between the beat-signal to be stabilized and an external RF reference. The feedback-loop of the phase-locked loop is implemented such that the phase-difference between the beat-signal and the RF reference is minimized. A residual phase-difference still remains due to limited locking bandwidth and imperfections of the feedback-loop. This residual small phase difference is still present on $\Delta f_{ceo}$ and $\delta$ and therefore according to eq. (9) will be imprinted on the reconstructed optical frequency $f_{opt}$. In some embodiments the phase noise of the output of the phase detectors at closed phase locked loops e.g. the in-loop error signal is recorded and used to compute correction terms to the interferogram or to the reconstructed optical spectrum. Alternatively, frequency locking schemes can be implemented and the error signal from the frequency locks can be recorded and used for the computation of correction terms.

In other words we obtain appropriate corrections to $\Delta f_{ceo}$ and $\delta$ by recording the difference in the phase of an RF signal S1 and the difference frequency S2 of two comb lines while the phase or frequency of S1 and S2 are locked. Alternatively, S2 can also be derived directly from the difference between the repetition rates of the two frequency combs. More generally, a signal S2 can also be derived from the individual repetition rates of the two mode locked lasers, the individual carrier envelope offset frequencies of the two lasers or their difference as well as any beat signal between a cw reference laser and an individual comb line of the mode locked lasers and the error signal from the phase locked loop or a frequency lock can be used to obtain corrections to the value of S2.

Figure 3:
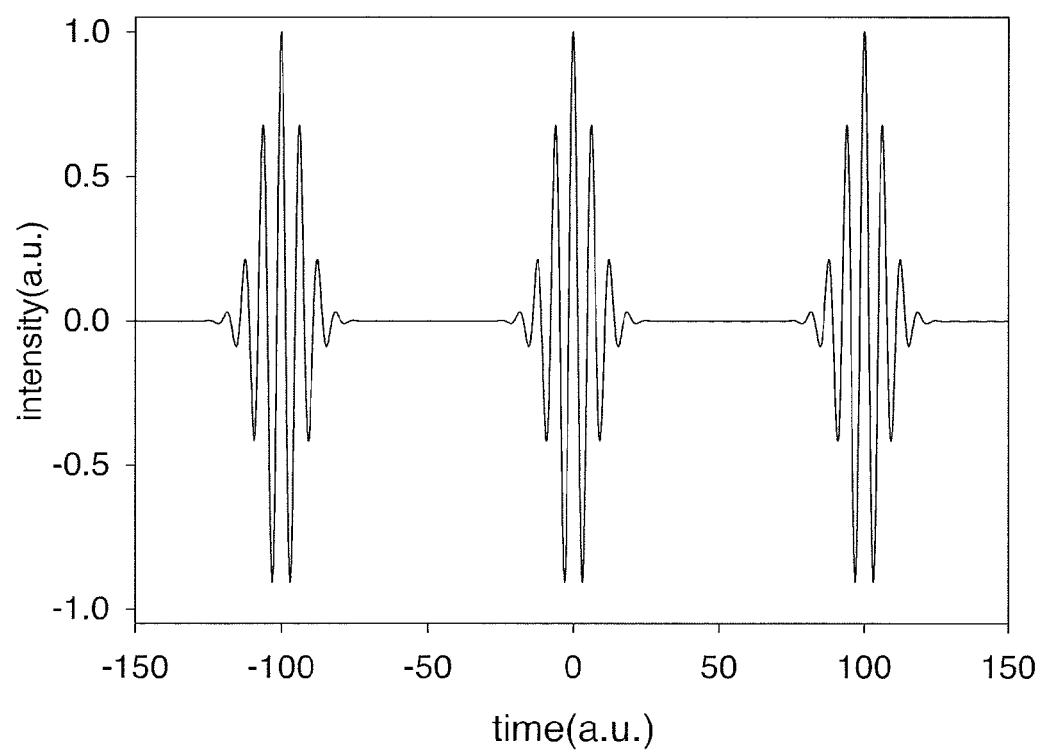
FIG. 3 is a plot illustrating three adjacent interferograms obtainable with a CDSL.

Moreover, in CDSLs the frequency resolution can further be improved by successive recording of more than one interferogram as illustrated in FIG. 3, where N=3 successive interferograms are shown. To first order the obtainable resolution is then inversely proportional to the number of recorded interferograms and limited by the coherence time of the cw reference lasers. Indeed, it is often preferable to increase the resolution of a FTS based on a CDSL by increasing the number of recorded interferograms rather than by incorporating a lower repetition rate laser, because mode locked lasers, and particularly mode locked fiber lasers, are typically more stable and less sensitive to environmental fluctuations when operated at higher repetition rates.

However, even with the inclusion of a phase correction term or an increased signal acquisition time, only an improvement in frequency resolution relative to the cw reference lasers is accomplished. It is sometimes beneficial to reference a FTS to the universally available Global Positioning frequency standard (GPS). In at least one embodiment this can be accomplished with an arrangement similar to FIG. 1 with an additional f-2f interferometer, for example as disclosed in '859, inserted via a beamsplitter at the output of either oscillator O1 or O2. Additional frequency broadening stages are included to generate an octave spanning spectrum as disclosed in '435. The f-2f interferometer can then be used to lock the carrier envelope offset frequency of one of the two oscillators, for example $f_{ceo1}$, with an additional phase locked loop, which can be implemented via modulation of the pump current of the relevant mode locked laser. Modulation of the pump current can further be used to lock the repetition rate $f_{rep}+\delta$ of the second laser to GPS. Once $f_{ceo1}$ and $f_{rep}+\delta$ are locked, $f_{rep}$ and $\Delta f_{ceo}$ can be related to the GPS reference frequency, allowing for absolute frequency calibration (with respect to GPS). Alternatively, we can also lock only the $f_{ceo1}$ beat signal and record the repetition rate of $f_{rep}+\delta$ in order to obtain calibration to GPS. Equally, both $f_{ceo1}$ and $f_{rep}+\delta$ can be recorded to obtain GPS calibration via optical referencing.

The frequency broadening stages included after oscillators O1 and O2 can further comprise optical parametric oscillators (OPOs) to enable spectroscopic measurements in the mid-IR. Such OPOs can for example be constructed from periodically poled $LiNbO_3$ or optically patterned GaAs crystals, although any other nonlinear crystals can also be used. Both the repetition rate and the carrier envelope offset frequency of the OPOs can be locked to oscillators O1 and O2; with a slight difference in repetition rate a FTS operating in the mid-IR spectral region can thus be constructed. OPOs with carrier envelope offset frequency locked to a pump laser are known and are not further described here.

Figure 4:
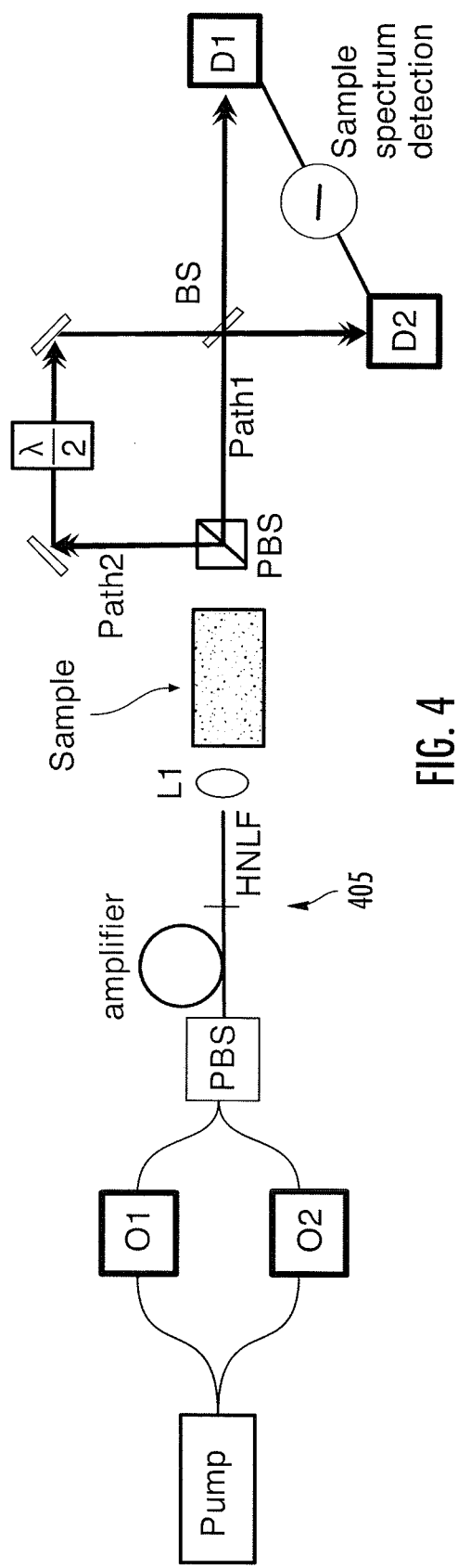
FIG. 4 is a schematic diagram illustrating dual balanced detection in a FTS based on a CDSL.

In various embodiments the signal/noise ratio of a FTS based on a CDSL can further be improved by implementing a dual balanced detection technique, as shown in FIG. 4. The output pulses of oscillators O1 and O2 are combined with a polarization beam splitter and aligned to propagate along two orthogonal polarization axes of a fiber amplifier and an optional spectral broadening unit 405, which may include a highly nonlinear fiber (HLNF), a non-linear fiber amplifier, or various combinations thereof. In the example of FIG. 4, the pulses then pass an optical sample and the two orthogonal polarizations are split into two propagation paths path 1 and path 2 via a second polarization beam splitter disposed downstream from the sample. A half-wave plate ($\lambda/2$) inserted in path 2 realigns the polarization directions. The pulses are then combined via optical beam splitter BS, and the signal due to interference between the two oscillators is detected using detectors D1 and D2. Because the interference signal detected on detectors D1 and D2 is out of phase, by subtraction of the signal measured on D1 and D2 any cw background in the detected signal can be eliminated, leading to an increase in signal/noise ratio for the detected interference signal. In some embodiments, to obtain a very high signal/noise ratio for the interference signal, it is beneficial to use the same pump laser for both oscillators (this can be done for example using a beam-splitter for splitting the pump appropriately, as shown) and to balance the dispersion along both propagation paths.

In the example of FIG. 4 a dual balanced detection scheme using one amplifier and nonlinear spectral broadening element is shown. In various embodiments dual balanced detection schemes can also be readily employed using two oscillators and two amplifiers as well as two nonlinear spectral broadening elements. In some embodiments it is beneficial to use the same pump laser for both oscillators and the same pump laser for both amplifiers. Such schemes are not separately shown. Also, a dual balanced detection scheme can be used in conjunction with the arrangement of FIGS. 1 and 2, i.e. via subtracting the current from detectors D5 and D6 to improve the obtainable S/N ratios in the detection scheme. In this case, it is beneficial to move the sample to between beamsplitters B1 and B2 in FIG. 2. In addition to Mach-Zehnder configurations, any other suitable dual beam interferometer can also be implemented. Dual balanced detection is applicable to reduce amplitude noise in any of such dual beam interferometers, even when the amplitude noise from both beams is not correlated. It is required, however, to balance the signal level on both detectors. The better the signal balance, the more amplitude noise reduction is achievable. For broadband signals, one can further use adjustable attenuators which can be used to compensate for any wavelength-dependent signal differences. In various embodiments signal processing equipment (not shown) may also be utilized to process the detector output signals, and the information may be utilized in a metrology or imaging system. Numerous combinations are possible.

Figure 5:
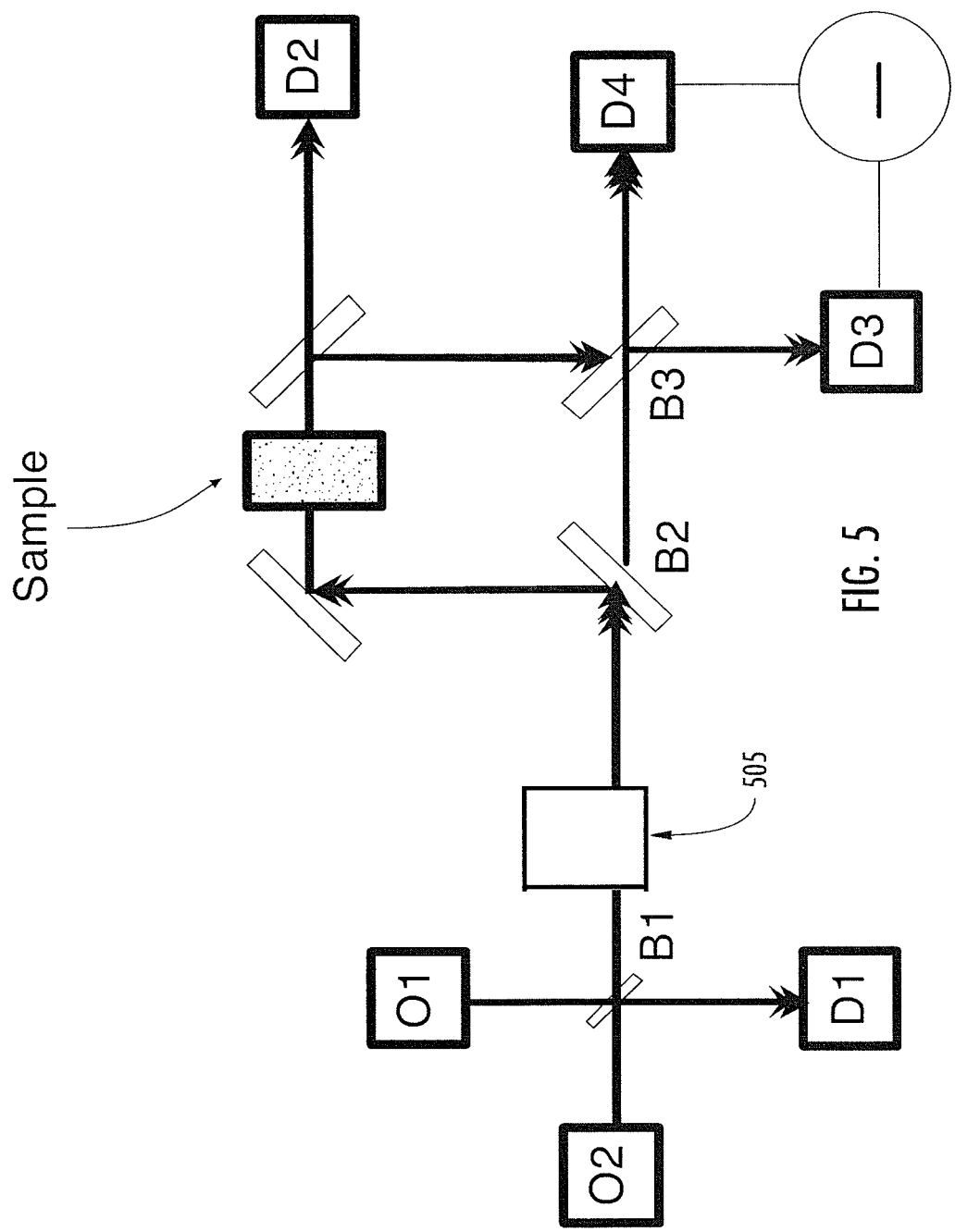
FIG. 5 is a schematic diagram of an arrangement for measuring the absorption and phase response of a sample in a FTS based on a CDSL.

Schemes for measuring the phase response of samples in absorption FTS constructed with frequency comb lasers are well known (S. Schiller et al., 'Spectrometry with frequency combs', Opt. Lett., vol. 27, pp. 766-768 (2002). Similarly the phase response of samples can also be measured when using absorption FTS based on CDSL. An exemplary embodiment of an FTS detector and sample arrangement for phase measurements based on a Mach-Zehnder interferometer is shown in FIG. 5. Here O1 and O2 are the mode locked oscillators, and the outputs are combined via beam splitter B1. In some embodiments O1 and O2 can further be connected to cw lasers for control of their carrier envelope offset frequencies and repetition rates as described with reference to FIG. 1. The reference spectrum of oscillators O1 and O2 is measured with detector D1. Additional amplification and spectral broadening stages 505 can further be implemented between beam splitters B1 and B2 as discussed in '435 (not shown). For example, a combination 405 of a linear fiber amplifier and a HLNF as shown in FIG. 4 herein, and/or a non-linear fiber amplifier may be utilized for amplification and broadening.

Referring again to the example FIG. 5, a Mach-Zehnder interferometer is configured by splitting the combined outputs of O1 and O2, with the sample in one path of the interferometer. A path length difference can further be incorporated in the two arms of the Mach-Zehnder interferometer in order to avoid signal distortions from cross phase modulation in any nonlinear spectral broadening stages as also discussed in '435. The sample transmission is further measured at detector D2 and the phase response is measured with detectors D3 and D4. When properly adjusting the phase delay along the top and bottom arm of the Mach-Zehnder interferometer and subtracting the photodetector currents of D3 and D4, a signal response proportional to $t(\omega) \times \cos(\phi(\omega))$ is obtained, where $t^2(\omega)$ is the sample transmission and $\phi(\omega)$ is the sample phase response as a function of frequency.

Figure 6:
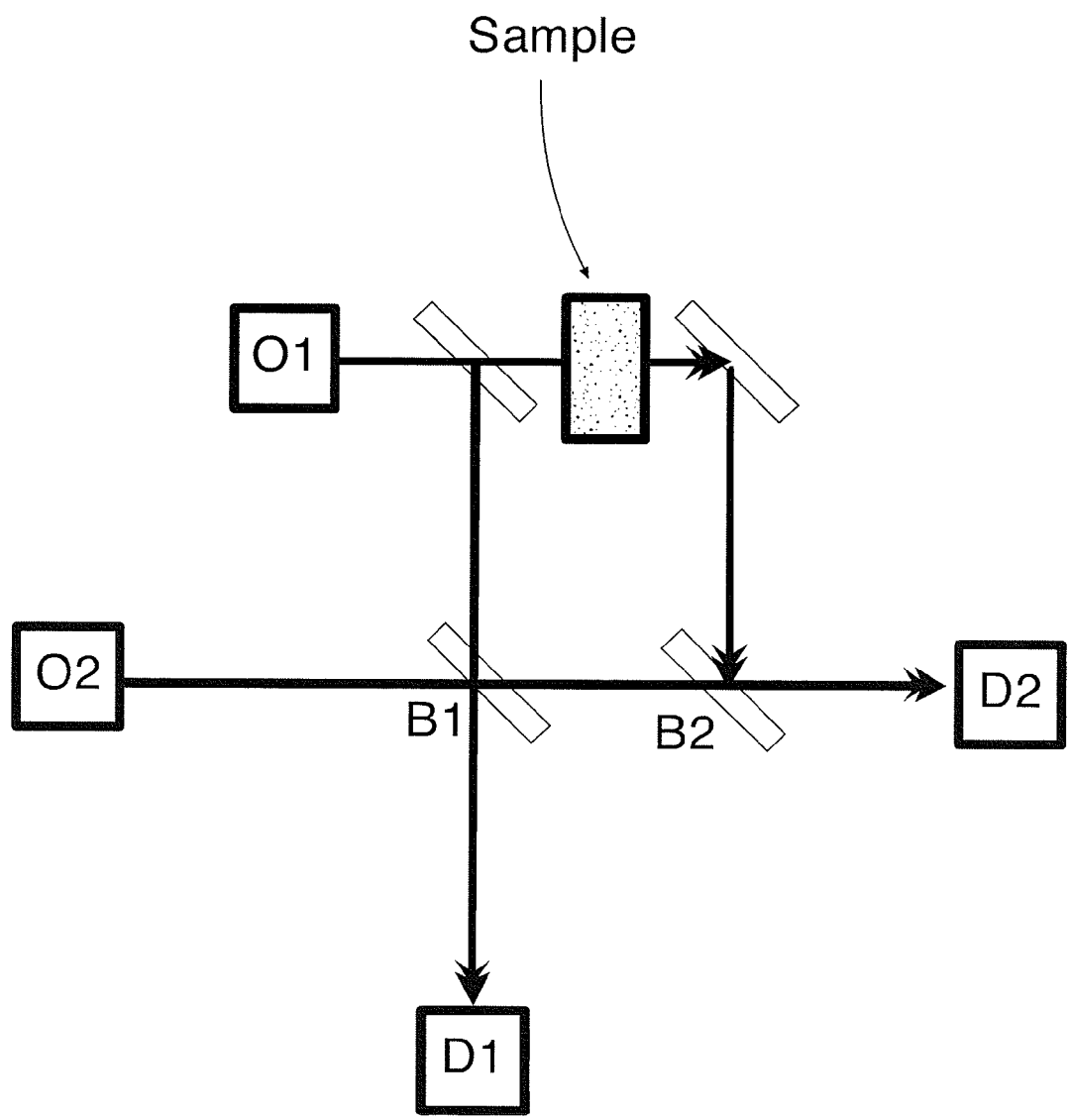
FIG. 6 is a schematic diagram of an alternative arrangement for measuring the absorption and phase response of a sample in a FTS based on a CDSL.

Alternatively, the phase and absorption response of the sample can be obtained using a sample and detector arrangement as shown in FIG. 6. Such a scheme was discussed by Coddington and is not further described here.

Figure 7:
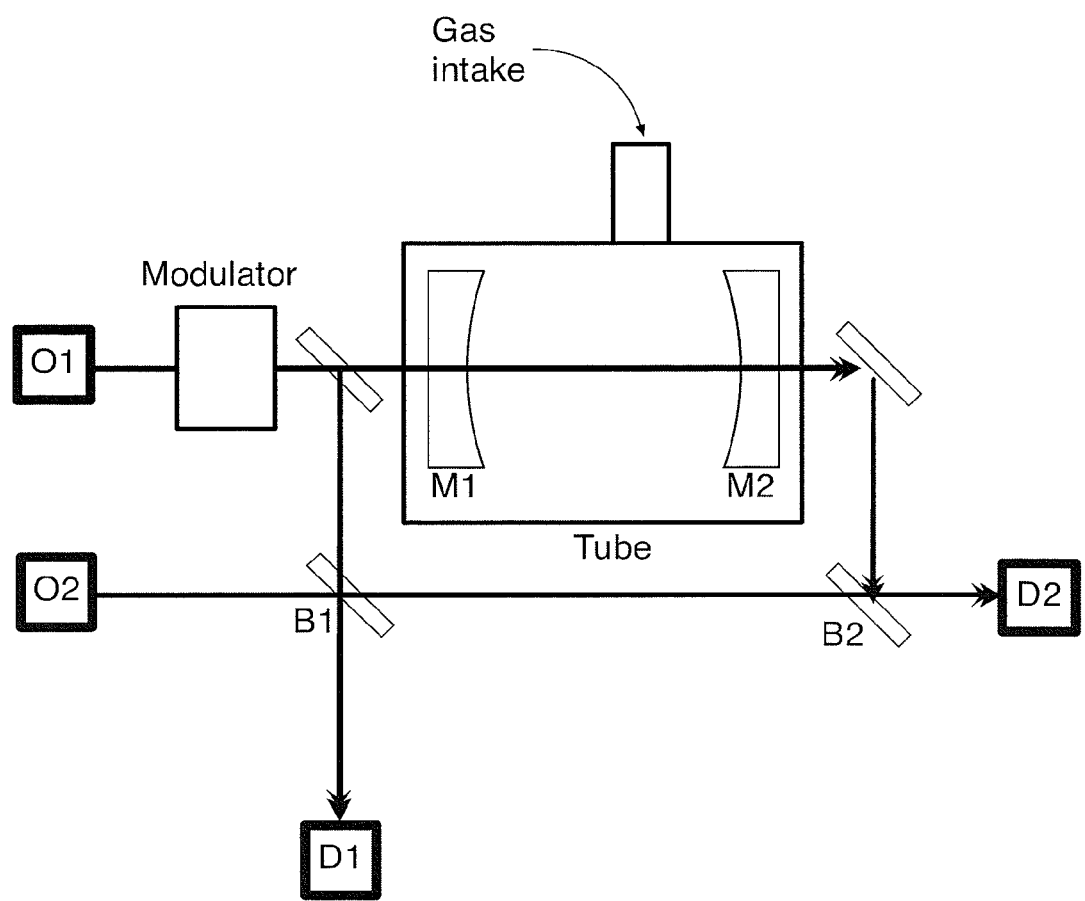
FIG. 7 is a schematic diagram of an enhancement cavity for improved sensitivity of absorption and phase measurements using a FTS based on a CDSL.

Also, the sensitivity of an absorption FTS may be increased by using an enhancement cavity with a cavity round-trip time matched to the repetition rate of one oscillator (e.g. oscillator O1), as shown in FIG. 7. The enhancement cavity is inserted into one arm of the interferometer and it is preferably mounted into a long tube and terminated with mirrors M1 and M2. The tube further contains a gas intake valve and can also contain a gas output valve. In various embodiments the sensitivity may be further increased with matching of the cavity round trip time of oscillator O1 to the round trip time of the enhancement cavity, as discussed in '998. In addition, phase matching between the cavity and oscillator O1 is implemented. Phase matching can be obtained by adjustment of the carrier envelope offset frequency of oscillator O1, as discussed in '998 or by frequency shifting of the oscillator pulses with an inserted optical modulator, as shown in FIG. 7.

When using OPOs in conjunction with oscillators O1 and O2, an increase in sensitivity for spectral measurements can be obtained without a separate enhancement cavity. In this case, a gas cell can be directly inserted into one of the OPOs. For spectral absorption measurements, very high sensitivity for trace gas detection can thus be obtained. Such an arrangement is not separately shown.

Figure 8:
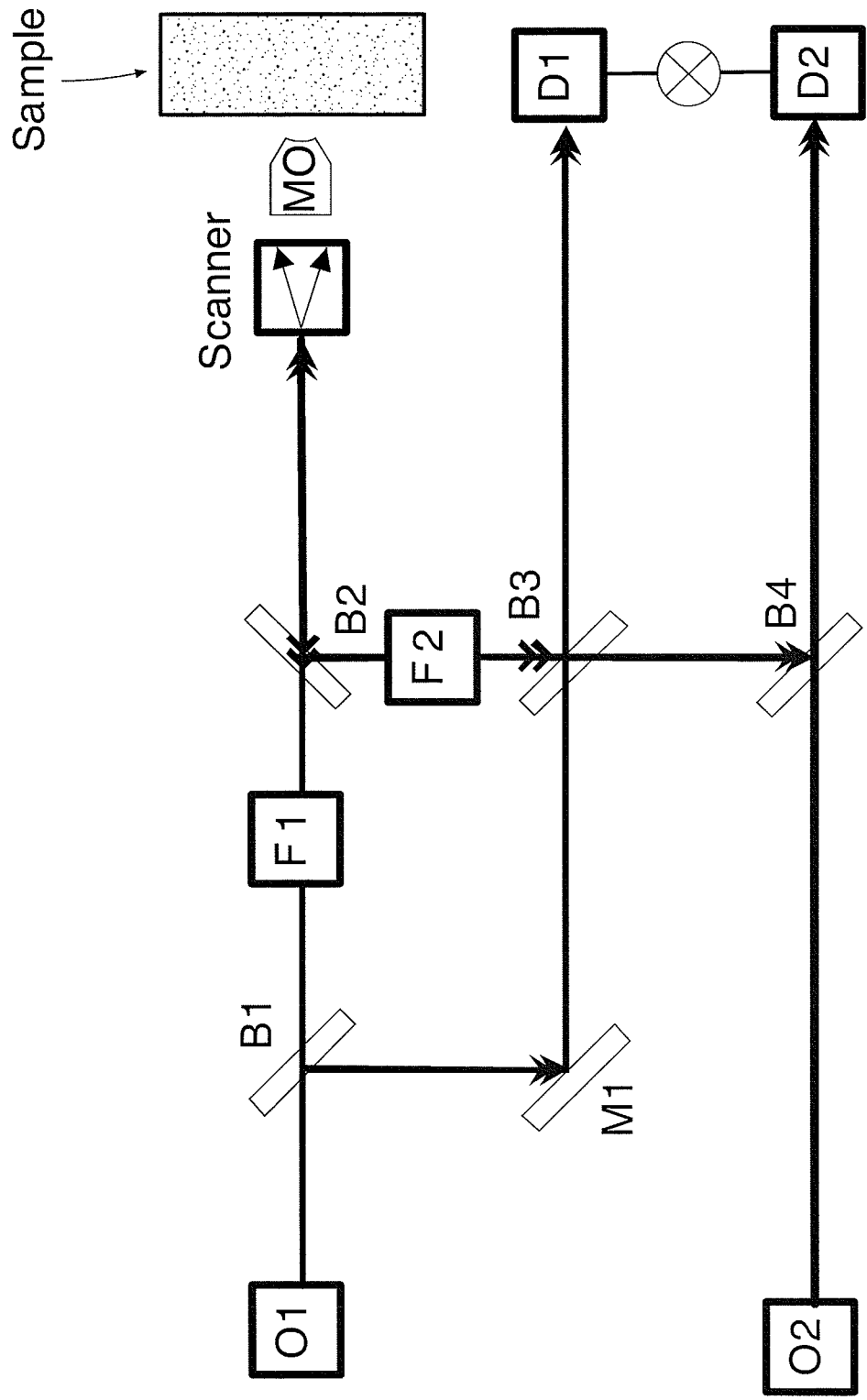
FIG. 8 is a schematic diagram of an arrangement used for obtaining spatially resolved emission spectra from a sample.

By way of example, a CDSL configured for emission FTS is shown in FIG. 8. In this example oscillators O1 and O2 generate femtosecond pulses which can further be amplified and spectrally broadened as discussed above, (not shown). As discussed above the oscillators operate at slightly different repetition rates and the carrier envelope offset frequency of both oscillators can further be controlled. The outputs of the oscillators are preferably compressed to a pulse width of less than about 1 ps. The output of oscillator O1 is split via beamsplitter B1 into two propagation paths. Pulses propagating in the upper propagation path are then directed through a narrow bandpass filter F1 to reduce the pulse bandwidth. Ideally the bandpass filter temporally broadens the pulses to a width of about 1-100 ps. The broadened pulses can further be amplified in another amplifier (not shown). In this example the broadened pulses are then directed through an optical scanner and focused via a microscope objective MO onto a sample, which induces spectral emission in the sample. For example, various samples will have a Raman response and emit a weak Raman spectrum. The Raman response can further be enhanced using surface enhancement techniques, known as surface enhanced Raman scattering, SERS or resonant Raman scattering, RRS, or any enhancement techniques, which are known in the art. The emission spectrum is then collected with the microscope objective and directed via beamsplitters B2, B3 and B4 onto detectors D1 and D2. Notch or high-pass filter F2 filters the pump pulses impinging onto the sample and is configured to transmit the spectral emission or Raman emission from the sample. The emission signal and the pulses from oscillators O1 and O2 are further combined via beam splitters B3 and B4 respectively and detected via detectors D1 and D2. In various embodiments spectral overlap between the emission spectra and the oscillator spectra is provided.

In effect, the short oscillator pulses sample the long lasting spectral emission emitted from the sample as a function of time. The output of detectors D1 and D2 corresponds to the optical interference signal between the sample emission and the output from oscillators O1 and O2 respectively. The non-DC part of the output of detectors D1 and D2 is proportional to a convolution of the respective pulse envelope with the sample emission $E_{em}(t)$ apart from a phase factor. The non-DC part of the output of detectors D1 and D2 is then electronically multiplied and further considering the pulses are very much shorter than the sample emission, a signal $E_{em}(t)$ $E_{em}(t-\tau)$ apart from a phase factor is produced, where $E_{em}(t)$ is the emission signal as a function of time and $\tau$ is the time delay between the two pulses emitted from oscillators O1 and O2. The time delay $\tau$ advances by a small amount between each sampling point, where a sampling event is for example triggered with oscillator O2 and the detector output is recorded at this sampling event with a rate corresponding to the repetition rate of oscillator O2. Knowledge of the difference in repetition rates between the two oscillators or a recording of the difference in the repetition rates between both oscillators then allows obtaining the precise value of $\tau$ for each sampling point. The average value of $E_{em}(t)E_{em}(t-\tau)$ is further equivalent to a summation over all time and thus we can write $$\Gamma(\tau)=\Sigma E_{em}(t)E_{em}(t-\tau)$$

$\Gamma(\tau)$ is thus equivalent to the autocorrelation function of $E_{em}(t)$ and the emission spectrum is hence obtained from a Fourier transform of $\Gamma(\tau)$. Because the product $E_{em}(t)E_{em}(t-\tau)$ depends on the carrier envelope phase of the sampling pulses, the carrier envelope offset frequency of the two oscillator pulses is stabilized. Alternatively, an appropriate phase correction term can be obtained via recording of $\Delta f_{ceo}$. Equally fluctuations in the difference $\delta$ between the two repetition rates of the two oscillators can be monitored to obtain precise values of $\tau$ as a function of time. $\Delta f_{ceo}$ and $\delta$ can be obtained using two cw lasers as discussed with respect to FIG. 1, which is not further explained here. In this example an arrangement for the detection of emission spectra in reflection is shown. However, a similar arrangement could also be used in transmission which is not separately shown.

Figure 9:
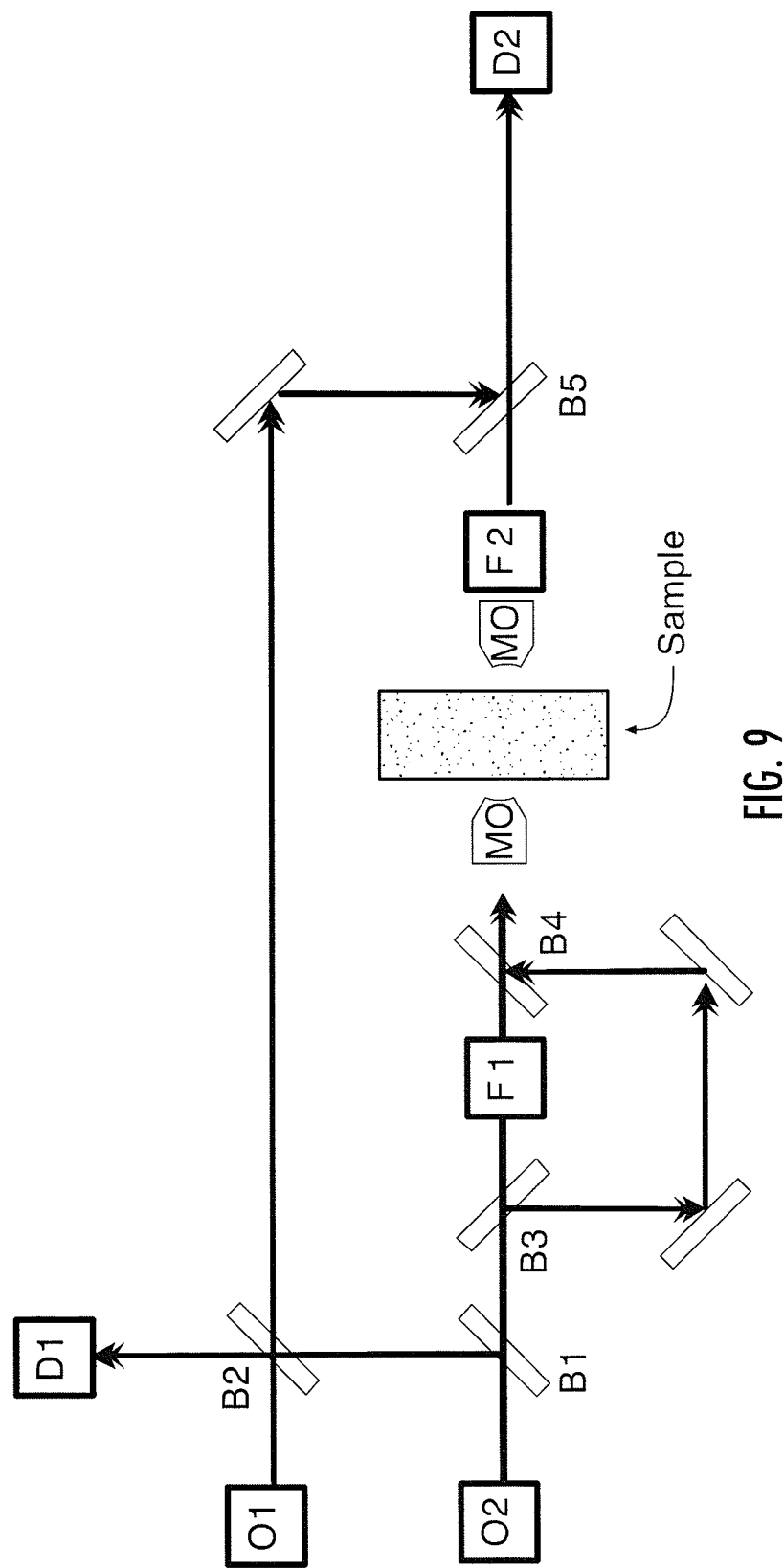
FIG. 9 is a schematic diagram of an arrangement for obtaining spatially resolved stimulated Raman emission spectra from a sample.

As yet another example, a CDSL configured for the measurement of stimulated emission spectra is shown in FIG. 9. Here oscillators O1 and O2 generate broad bandwidth pulses which can further be amplified and spectrally broadened (not shown). As discussed above, the oscillators are configured to operate at slightly different repetition rates and the carrier envelope offset frequency of both oscillators can further be controlled. The output of oscillators O1 and O2 is directed via beam splitters B1 and B2 onto detector D1 to obtain a reference spectrum. In the following we refer to the unfiltered pulses from oscillator O2 as test pulses. A fraction of the test pulse output of oscillator O2 is further passed through a narrow bandpass filter F1 to generate pump pulses. The pump pulses can further be amplified, which is not separately shown. The pump pulses from O2 and the test pulses from O2 are further combined with beamsplitter 4 and directed onto the test sample via a microscope objective, where temporal overlap on the test sample is ensured. A notch filter, F2, then filters out the narrow pump pulses collected by another microscope objective so that broad bandwidth test pulses are transmitted to detector D2, where they are also combined with the output from oscillator O1 via beamsplitter B5. For strong pump pulses, stimulated Raman scattering emission leads to an amplification (or attenuation) of certain spectral bands inside the test pulses. By subtracting the spectra detected with detectors D1 and D2, an accurate measurement of the stimulated Raman emission spectrum can be readily obtained. Spatially resolved information is generated via changing the position of the test sample between the two microscope objectives. In FIG. 9 an arrangement for transmission measurement is shown. A similar arrangement can also be used for reflection measurements with modifications of the optical system. In some embodiments both reflection and transmission measurements may be obtained. Both oscillators can further be pumped by the same pump laser for noise reduction and improved signal/noise ratios can be obtained via the implementation of dual balanced detection schemes.

A CDSL for the measurement of coherent anti-Stokes Raman scattering microscopy (CARS) is shown in FIG. 10. Oscillators O1 and O2 are conditioned to produce a broad spectral output with a spectral width corresponding to the width of the Raman spectra of the sample. In a specific implementation, oscillator O2 is used to generate both picosecond Raman pulses as well as red-shifted signal pulses. For example pump and signal pulses can be obtained via spectral filtering (using filters F1 and F2) from broad bandwidth pulses. Both pump and signal pulses are then transmitted through the sample leading to the generation of a blue-shifted anti-Stokes output. The signal and pump are subsequently suppressed by a short pass filter, F4, which transmits the anti-Stokes output. The output of oscillator O1 is then preferably chosen to overlap with the anti-Stokes spectrum generated in the sample using, for example, filter F3. The anti-Stokes output from the sample is then combined via beamsplitter B3 with the output of oscillator O1 and sampled with detectors D1 and D2, where dual balanced detection can also be implemented. This scheme is effectively equivalent to heterodyne detection of the anti-Stokes CARS output with oscillator O1 acting as the local oscillator and can produce very good sensitivity. Moreover, a high degree of vibrational selectivity can be obtained using relatively narrow signal and/or local oscillator pulses. Using optical scanners and appropriate imaging devices, the construction of a CARS microscope is further possible.

Figure 11:
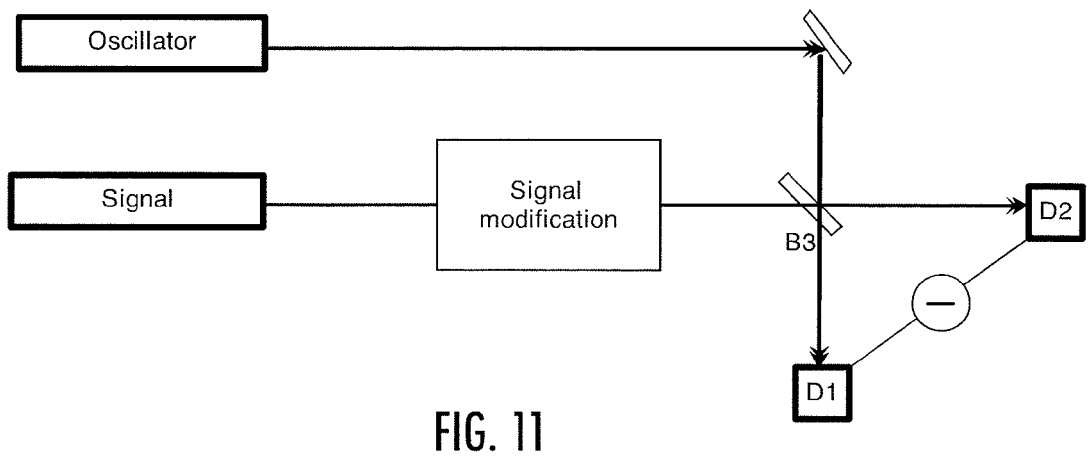
FIG. 11 is schematic diagram of a CDSL used in linear optical sampling.

The detection scheme shown in FIG. 10 is effectively an example of a generic sampling or coherent detection method, as shown in FIG. 11. Here the oscillator and the signal comprise two mode locked lasers operating at slightly different repetition rates, which can in turn be phase locked to external cw reference lasers for improved carrier phase stability. In this scheme the signal is modified coherently in the signal modification stage and the modified signal is then sampled with the oscillator pulses. An appropriate Fourier transform of the sampled detector outputs from detectors D1 and D2 then yields the product of the spectrum of oscillator O1 times the modified signal spectrum. If the oscillator pulses and signal pulses prior to signal modification are known with reasonable accuracy, the inverse of the Fourier transform can then yield the impulse response of the signal modification unit.

Figure 12:
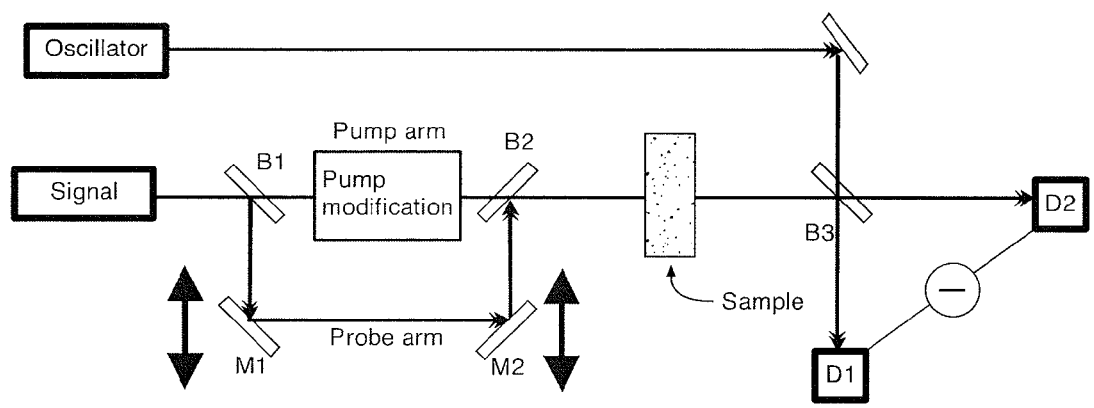
FIG. 12 is a schematic diagram of a CDSL in a pump probe configuration.

An application of the generic sampling method of FIG. 11 is shown in FIG. 12 for pump probe measurements. As discussed above, local oscillator pulses and signal pulses are derived from two mode locked oscillators operating at slightly different repetition rates, which are in turn locked to—or referenced by—cw lasers for repetition rate and carrier envelope offset frequency control, or that incorporate other means for carrier envelope offset frequency control. Additional spectral broadening, amplification and compression of the oscillator pulses may further be incorporated as set forth above. The signal pulses are further used to generate high power pump pulses propagating in the pump arm and a fraction of the signal pulses is split off via beam splitter B1 to generate probe pulses propagating in a probe arm. The probe and pump pulses are recombined with beam splitter B2. The time delay between the probe and pump pulses can be adjusted freely by translation of mirrors M1 and M2. The pulses propagating in the pump arm can further be modified via a pump modification unit; this modification can, for example, comprise frequency doubling, shifting, polarization rotation, optical filtering, optical phase and amplitude modulations and pulse chirping. Alternatively, the pulses propagating in the probe arm can also be modified. The pump and probe pulses are further focused into a sample, where the strong pump pulses lead to changes in the pulse propagation characteristics of the probe pulses. For example, the pump pulses can induce Raman oscillations in the sample, which generate time dependent phase modulations $\Phi(\tau)$ in the probe pulses propagating through the sample, provided the probe pulses are adjusted to arrive after the pump pulses. The time dependent phase modulations $\Phi(\tau)$ and the corresponding phase modulation spectrum can be analyzed by sampling the probe pulses with the local oscillator pulses using detectors D1 and D2, which results in a measurement of the electric field of the probe pulses. The absolute value of the phase modulations is then obtained by comparing the field of the probe pulses with the pump pulses on and off. From the measured phase modulation $\Phi(\tau)$ induced by strong pump pulses, the Raman spectrum $R(\Omega)$ of the sample can be calculated from a Fourier transform of $F[\Phi(\tau)]$ as described in Schlup et al., 'Sensitive and selective detection of low-frequency vibrational modes through a phase-shifting Fourier-Transform Spectroscopy', IEEE J. Quantum Electronics, vol. 45, No. 7, pp. 777-782 (2009). Note that in contrast to conventional Raman spectral measurements as described by Schlup, no variation of the time delay between the pump and probe pulses are required, i.e. the timing between the pump and probe pulses can be fixed. The probe pulses should further be sufficiently long in order to allow recording of the phase fluctuations over a certain time period.

Although we discussed the impact of phase modulations, in various embodiments absorption modulations induced by pump pulses on probe pulses can also be measured. Moreover, the time dependence of the probe phase modulations $\Phi(\tau)$ as a function of probe spectral frequency can also be measured. Such a measurement is provided by inserting a high finesse etalon into the probe arm in FIG. 12, which is not separately shown. The high finesse etalon, allows transmission of a certain number of selected probe spectral frequencies (etalon teeth). The analysis of the phase modulations at each of these etalon teeth thus enables one to measure the phase modulations both as a function of time and probe spectral frequency $\Phi(\tau,\omega)$. This is an example of a two-dimensional spectroscopic measurement without moving parts. Such two-dimensional spectroscopic measurements are very useful for the detailed characterization of molecules as also discussed by Schlup et al. For example knowledge of $\Phi(\tau,\omega)$ allows for the calculation of the time resolved Raman spectrum $R(\Omega, t)$ via a two-dimensional Fourier transform as also discussed by Schlup et al.

Other forms of two-dimensional spectroscopy are also possible. For example two dimensional absorption spectroscopy as discussed by P. Hamm et al., in 'The two-dimensional IR nonlinear spectroscopy of a cyclic penta-peptide in relation to its three-dimensional structure', Prov. Nat. Acad. Sci., 96, 2036 (1999) is also possible with pump probe measurements as discussed with respect to FIG. 9, FIG. 10 and FIG. 12.

For example the arrangement as shown in FIG. 12 can be used for two dimensional absorption spectroscopy via inclusion of a tunable optical filter in the pump modification unit. The induced absorption spectrum of a probe pulse can then be measured as a function of pump pulse frequency as required for two-dimensional absorption spectroscopy. An important requirement is further that spectral overlap exists between the oscillator and probe pulses in the whole 'probed' spectral absorption range. Such a two dimensional spectroscopic measurement is referred to as double resonance experiment in the state of the art.

Figure 12A:
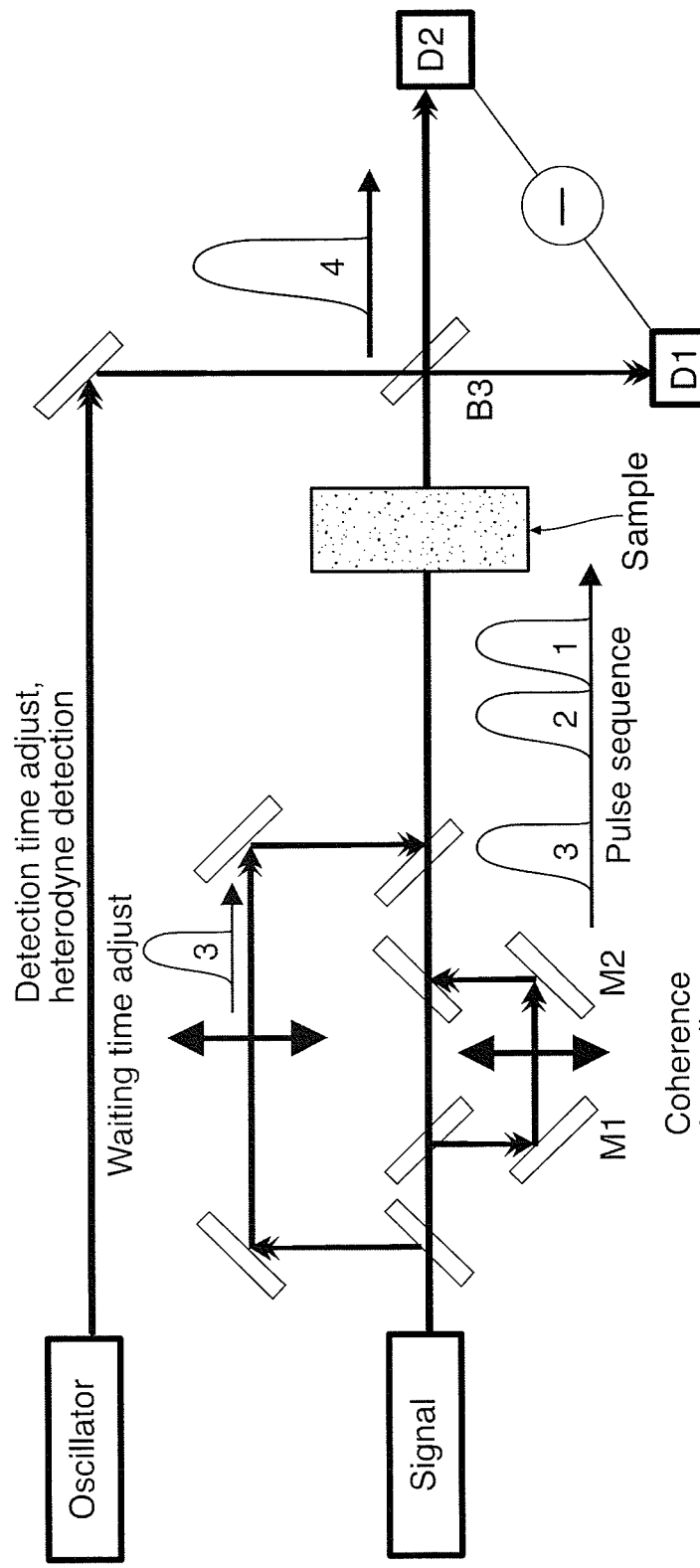
FIG. 12A is a schematic diagram illustrating the use of a CDSL in a two dimensional spectroscopy measurement.

Although we discussed probe pulse modification by only one pump pulse in a collinear arrangement, in principle any number of pump pulses can be used and a collinear arrangement between probe and oscillator pulses is not required in order to observe probe modifications with a local oscillator reference pulse in a CDSL arrangement. In particular a CDSL can also be implemented for general two dimensional spectroscopy. A possible configuration for two-dimensional Fourier transform spectroscopy is shown in FIG. 12A. Here again signal and oscillator sources operating at slightly different repetition rates as discussed with respect to FIG. 12 are used. The pulses from the signal source are split into a three pulse sequence (which is not necessarily collinear, i.e. a boxcar geometric configuration, as well known in the state of the art can be implemented) with an arrangement of two optical delay lines. Such three pulse sequences for two-dimensional spectroscopy were for example discussed in R. M. Hochstrasser et al., 'Two-dimensional spectroscopy at infrared and optical frequencies', in Proceedings of the National Academy of Sciences, vol. 104, pp. 1490 (2007). Here the first optical delay allows for an adjustable time separation $\tau$ between the first two pulses, the so-called coherence time adjustment $\tau$ in Hochstrasser. The second optical delay line allows for an adjustment of the time separation of the third pulse with respect to the first two pulses, the so-called waiting time adjustment T in Hochstrasser. These three pulses can then generate a photon echo signal pulse which is optically sampled as a function of time t (the so-called detection time in Hochstrasser) with the oscillator pulses, and detected with detectors D1 and D2. The resulting time domain interferogram can then be Fourier transformed along variables t and $\tau$ in order to yield two-dimensional absorption spectra. Instead of a single read out pulse 3, a sequence of read out pulses can also be implemented. Also the first two pulses can be modulated to increase the sensitivity of the measurement. In addition the transmission of pulse three can be directly measured with the first two pulses being on and off.

Such two-dimensional absorption spectra are highly useful for the analysis of complex molecular structures as for example discussed by Hochstrasser. Because of the great improvement in acquisition speeds possible for two-dimensional spectroscopy with the arrangement shown in FIG. 12A compared to conventional two-dimensional spectroscopy as discussed by Hochstrasser, the pump probe arrangement as discussed with respect to the examples of FIG. 12 and FIG. 12A is further adaptable to optical imaging applications and microscopy, by implementing an appropriate focusing and optical scanning arrangement in front of the sample and behind the sample. Further modifications of the actual pulses as well as their spatial and temporal arrangement and sequencing as well as the implementation of larger number of pulse sequences are also possible, allowing for general multi-dimensional spectroscopic measurements.

Figure 13:
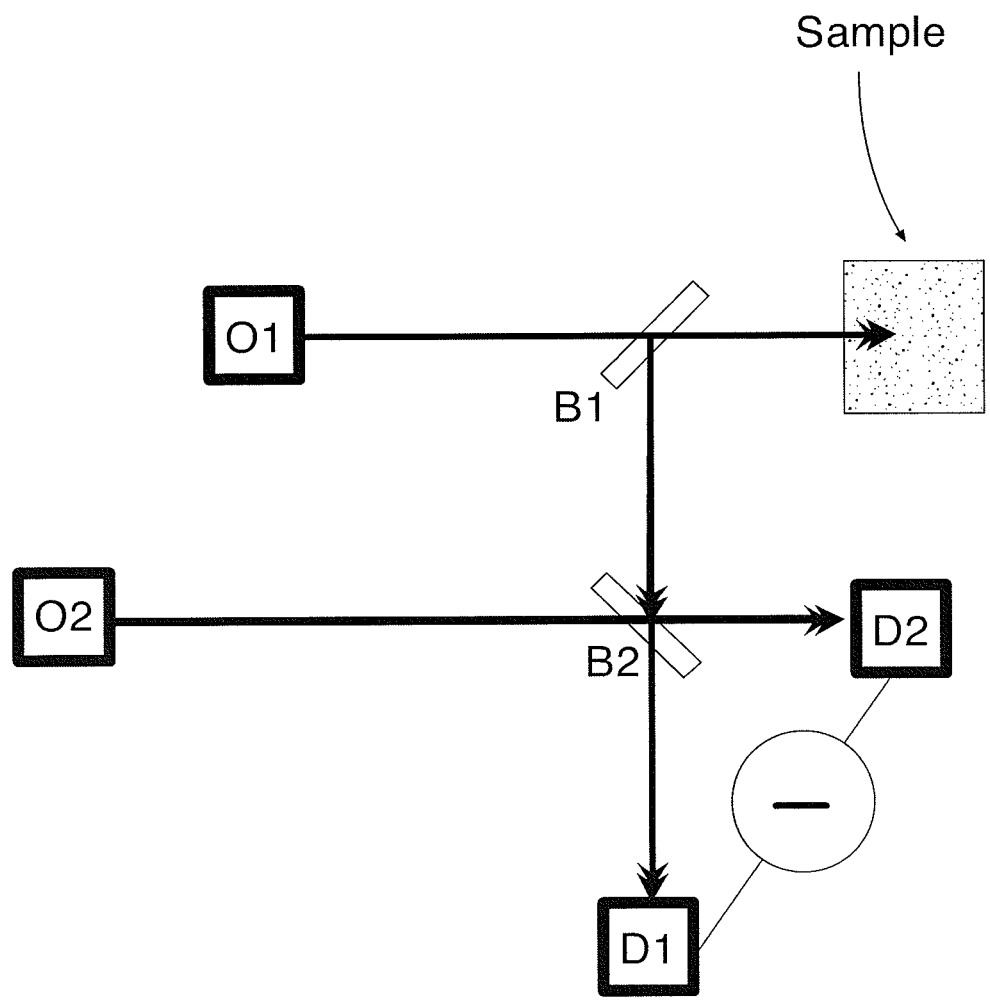
FIG. 13 is a schematic diagram illustrating the use of a CDSL in optical coherence tomography.

A CDSL as implemented for FTS operated in reflection or in optical coherence tomography is shown in FIG. 13. The oscillators can be connected to additional cw lasers as described with respect to FIG. 1. Additional frequency broadening stages can also be implemented to broaden the spectral output of the oscillators. The output of oscillator O1 is directed to the sample and the light reflected from the sample is directed to beam splitter B2 via beam splitter B1. The light reflected from the sample is then combined with the output from oscillator O2 via beam splitter B2. The combined light is then detected with detectors D1 and D2. Because the interference signal impinging onto the detectors is out of phase at least in a small bandwidth, an improvement in sensitivity can be achieved by the implementation of a dual balanced detection scheme, where the output of detectors D1 and D2 is subtracted. In order to implement a dual balanced detection scheme across a large bandwidth, in at least one embodiment an accurate balance of the dispersion along the two propagation paths of the two oscillators is implemented. When operated as a FTS in reflection, both the absorption and phase response of a sample can be obtained.

When used for optical coherence tomography, the detected signal is preferably filtered at the fundamental interferometric beat frequency, i.e. the equivalent Doppler shift frequency that results in reflection from a mirror moving at a uniform velocity. For a difference in repetition rates between the two oscillators of δ, the equivalent Doppler frequency $f_D$ is given by $f_D=(\delta/f_{rep})v_0$, where $v_0$ is the mean optical frequency of the output signal from the oscillators. For OCT applications it is not required to stabilize the carrier envelope offset frequency and therefore phase locking of the difference in repetition rates between the two oscillators is sufficient. CW lasers may be utilized in embodiments when ultra-high resolution is desirable. A similar arrangement may also be used in optical ranging applications.

Figure 14:
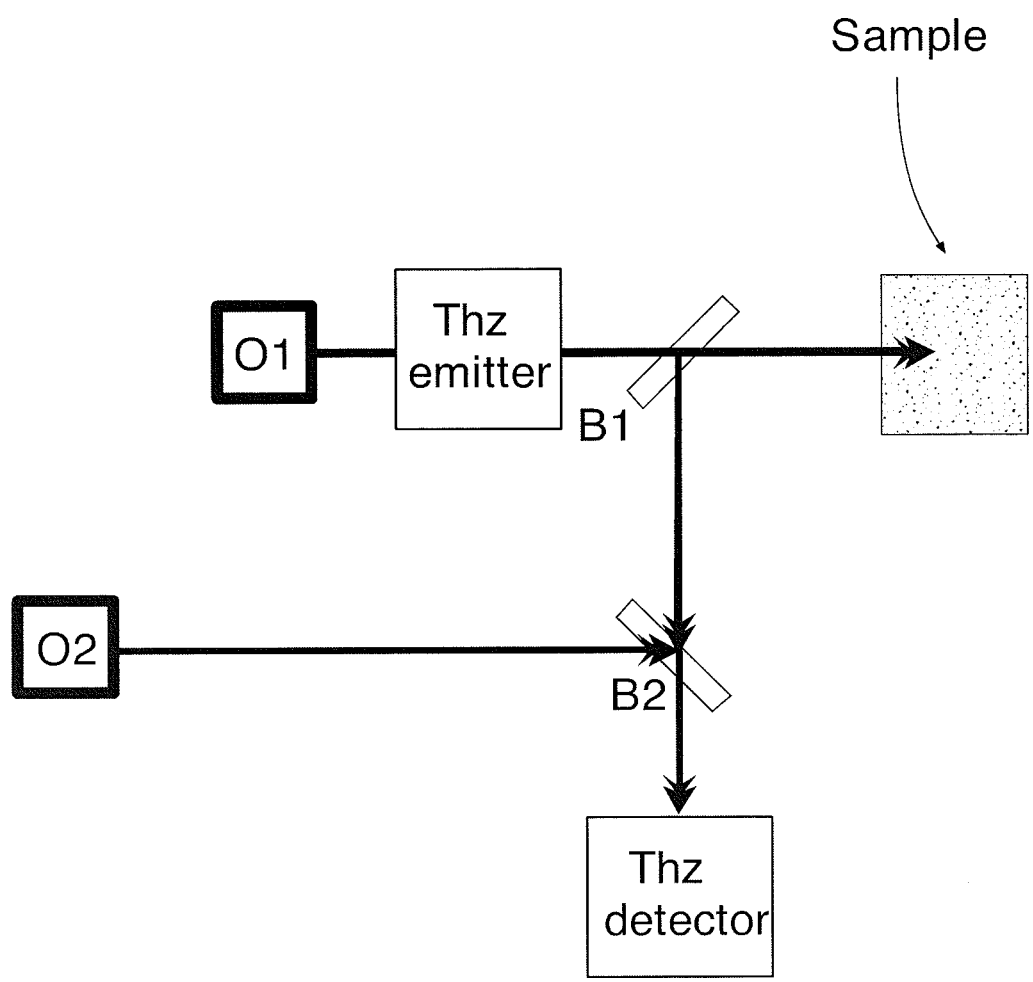
FIG. 14 is a schematic diagram illustrating a CDSL in THz ranging.

As another example, a CDSL for THz ranging is shown in FIG. 14. The arrangement is similar to FIG. 13, however an additional THz emitter is inserted after oscillator O1. The THz signal reflected from the sample is then directed via beamsplitters B1 and B2 onto the THz detector, where a pump probe detection scheme is implemented in order to achieve an optimum signal/noise ratio. Photoconductive emitters or optical rectification in electro-optic crystals as well known in the state of the art can be implemented for THz emission and detection. Also, as for OCT applications, a stabilization of the difference in repetition rates between the two oscillators is sufficient for THz ranging.

When using the arrangement as shown in FIG. 14 as a THz spectrometer operated in reflection, a photo-conductive antenna can be used as a THz detector to monitor the RF beat signal generated from the reflected THz spectrum. The THz reflection spectrum and the THz phase response can then be inferred from an RF analysis of the RF beat signal, as discussed in '435. Also, for THz applications a control of the carrier envelope offset frequencies is not required, because the THz generation process automatically nulls out the carrier envelope offset frequency shift.

Figure 15:
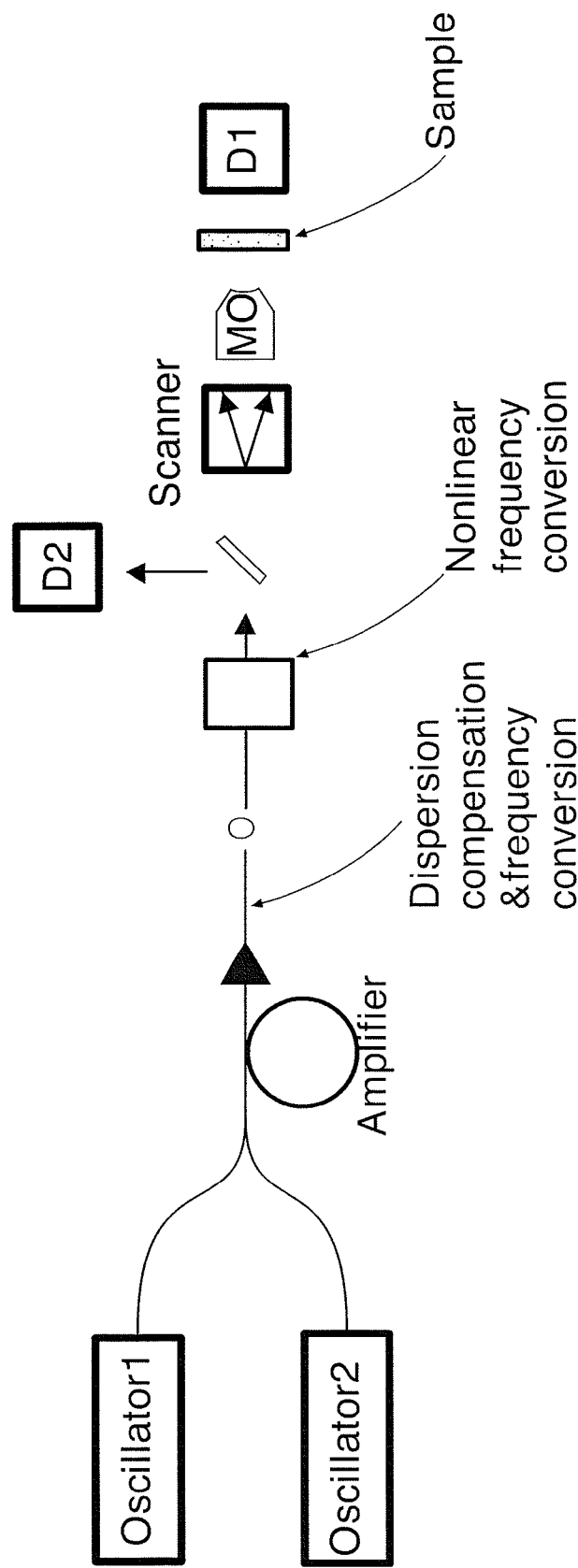
FIG. 15 is a schematic diagram illustrating a CDSL in THz spectroscopy and spectroscopic imaging.

The system shown in FIG. 1, can further be used in THz spectroscopy, micro-spectroscopy and optical imaging, for example as illustrated in FIG. 15. Here the two oscillators can further be connected to two cw lasers for a control of the difference in repetition rates and carrier envelope offset frequencies between the two lasers. The two oscillators are combined and amplified and additional frequency conversion sections based on supercontinuum generation in highly non-linear fibers or difference frequency generation as discussed in '435 can be implemented. The frequency converted signal is transmitted via an optical scanner and subsequently focused onto an optical sample. The transmitted signal is then detected via detector D1 or a focal plane array. Detector D2 is used to obtain a reference spectrum. The spectrally and spatially resolved sample transmission is then obtained via calculating the Fourier transform of the signal from detector D1 as a function of spatial position. The use of a focal plane array detector has the advantage that the spectrum can be measured simultaneously at many points, thus minimizing the time is takes to obtain an image.

By using a detector to measure the light reflected from the sample, spectrally resolved reflection data can also be obtained. Such a scheme is not separately shown.

Figure 16:
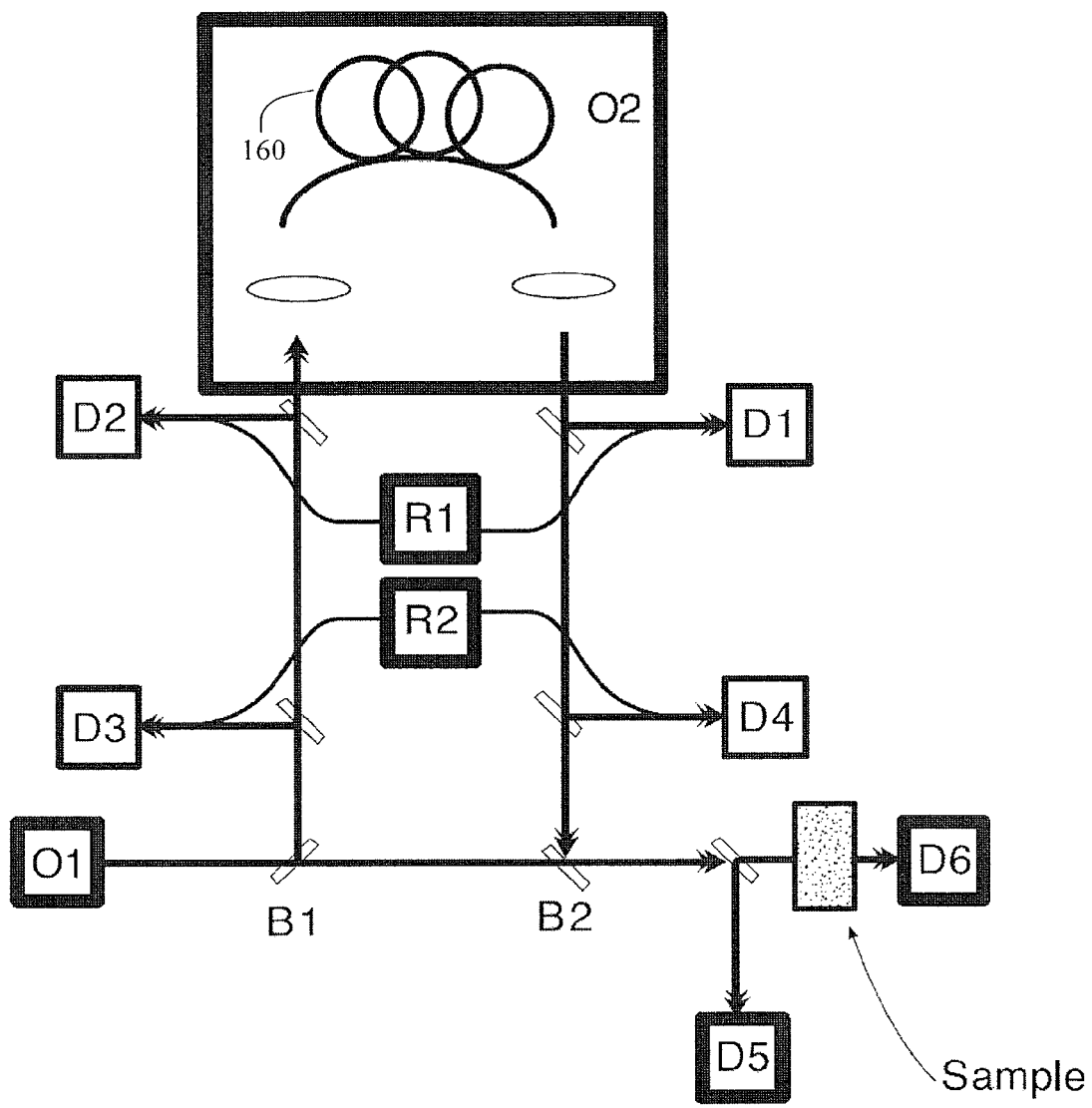
FIG. 16 is a schematic diagram illustrating an effective CDSL constructed with only one laser.

Various applications of CDSLs will generally be cost sensitive and therefore the use of two frequency comb lasers can be a barrier with respect to potential product introductions. However, one can use the coherence of the generated frequency combs to generate an interferogram between a pulse and a delayed replica with a time varying delay to eliminate one comb laser while still allowing for the recording of an interferogram between two pulses. Such an implementation is shown in FIG. 16. In this example only one comb laser O1 is used, where the cavity length of said oscillator is modulated at a high frequency. Beam splitter B1 then deflects some of the pulse into a long optical delay line. After propagation through the optical delay line, optically delayed pulses emerge; we refer to these pulses as delayed pulses. The optical delay line is conveniently a long length of fiber 160, with a length in the range from 10 m-several tens of km, or in the range from 100 m-10 km; however other optical delay lines can also be implemented, such as for example a Herriott cell. In various embodiments the length of optical fiber may be in the range from about 5 m to about 100 m, or other similar ranges. The time delayed pulses interfere at beamsplitter B2 with oscillator pulses arriving from O1 without optical delay, we refer to these pulses as direct pulses. Moreover, due to the rapid modulation of the oscillator repetition rate, the time delay between the direct and delayed pulses is time dependent, leading to a continuous scanning of the pulse separation at beamsplitter B2.

Essentially the delay line creates an effective second oscillator O2. All the previously discussed applications of CDSLs are thus applicable when using only one comb laser with a time delayed replica, i.e. such an effective second oscillator. However, any other applications where a scanning delay line is required are also possible; such other applications were for example discussed in WO 2009/000079 and U.S. Pat. No. 5,778,016. For example here detectors D5 and D6 are implemented for the measurement of the optical absorption of a sample, similar to what was already discussed with respect to FIG. 2.

The example CDSLs corresponding to FIG. 5-FIG. 15 may also be configured with one frequency comb laser with its time delayed replica for the construction of an effective CDSL or more generally a coherent scanning laser system (CSL). Amplification stages and spectral broadening stages can also be implemented to broaden the optical spectrum of the implemented oscillator upstream of beamsplitter B1 or downstream of beamsplitter B2 or anywhere else external to oscillator O1.

In the implementation shown in FIG. 16 a single-pass optical delay line is shown, equally a double-pass optical delay line can be used in conjunction with a Faraday rotator after the first pass in order to minimize polarization fluctuations in the optical delay line. In this case beamsplitter B1 can be used also to interferometrically combine the direct and delayed pulses. Such a configuration is not separately shown. Also, an actual absorbing medium can be inserted into the optical delay line in order to increase the sensitivity of an absorption measurement. For example a gaseous medium can be introduced into a Herriott cell for ultra-sensitive detection of trace gases.

For small cavity length modulations, the achievable maximum scan range of this scanning delay line is proportional to the oscillator repetition rate. It is thus preferable to implement oscillators operating at a repetition rate of 100 MHz or even more preferably at 500 MHz or higher. High oscillator repetition rates also generally allow for higher scan frequencies.

One limitation is the possible large absorption of silica fibers, particularly for wavelengths>1800 nm. Lower transmission losses can for example be obtained using silica photonic crystal fibers or photonic crystal fibers made from fluoride or chalcogenide fibers or bulk optic delay lines such as a Herriott cell, a White cell, or other suitable optical delay arrangement.

Another limitation arises from the dispersion of the optical delay line. However, a pulse compressor can be implemented at the end of the optical delay line for dispersion compensation. Alternatively, low dispersion fibers can also be implemented. Equally, dispersion in the optical delay line can be minimized when implementing a bulk optic delay line such as a Herriott cell, a White cell, or other suitable optical delay arrangement.

Another limitation arises from environmental variations of the delay line length, such variations can for example be eliminated by using active length stabilization as well known in the state of the art and for example described in K. Holman et al., 'Precise frequency transfer through a fiber network by use of 1.5-µm mode-locked sources', Opt. Lett., vol. 29, pp. 1554-1556 (2004) and J. Kim et al., Long-term femtosecond timing link stabilization using a single-crystal balanced cross-correlator', Optics Letters, 32, pp. 1044-1046 (2007). Generally, delay line length variations lead to slow spectral shifts between individual recorded Fourier transform spectra. Thus these spectral shifts can be accounted for by calibration with simultaneous recording of an optical reference such as an optical filter.

Another limitation is timing jitter of the oscillator pulses, which produces slow, random timing fluctuations between the direct and delayed pulses. Therefore, low timing jitter oscillator pulses are beneficial to implement.

However, random fluctuations in the interferogram recorded between the direct and delayed pulses can further be suppressed by using optical referencing techniques, as already discussed with respect to FIG. 1. As discussed above, two reference lasers R1 and R2 can be used, which are made to interfere with the outputs of the direct and delayed pulses via detectors D1-D4, to detect the difference between the repetition rates and carrier envelope offset frequencies of the direct and delayed pulses respectively. A recording of the fluctuations of the repetition rate and carrier envelope offset frequency can then be used to generate a corrected interferogram. A Fourier transform of the corrected interferogram then produces the actual RF spectrum, which can then be used to calculate the optical spectrum.

Similarly, since the approximate length of the optical delay line is known, information from detectors D2 and D3 can be used to calculate the differences in carrier envelope offset frequencies and pulse repetition rates at the second beam splitter, since to first order the optical delay line does not affect the carrier envelope offset frequency or the pulse repetition rate. Also the carrier envelope offset frequency can be measured upstream of the optical delay line in order to predict the carrier envelope offset frequency at the output of the optical delay line.

In order to simplify the interpretation of the measured interferogram, optical SSB mixers can also be implemented in place of detectors D1-D4, with two pairs of balanced detectors (for in-phase and quadrature detection) replacing each of the detectors D1-D4 as already discussed with respect to FIG. 1.

Alternatively, with a length stabilized optical delay line, the difference between the repetition rate and carrier envelope offset frequencies between the direct and delayed pulses can be separately measured without any referencing in order to obtain appropriate correction and calibration factors for the measured interferograms. As yet another alternative, only the difference in carrier envelope offset frequencies (or repetition rates) can be recorded while the difference in repetition rates (or carrier envelope offset frequencies) between the pulses can be inferred from another measurement.

Figure 16A:
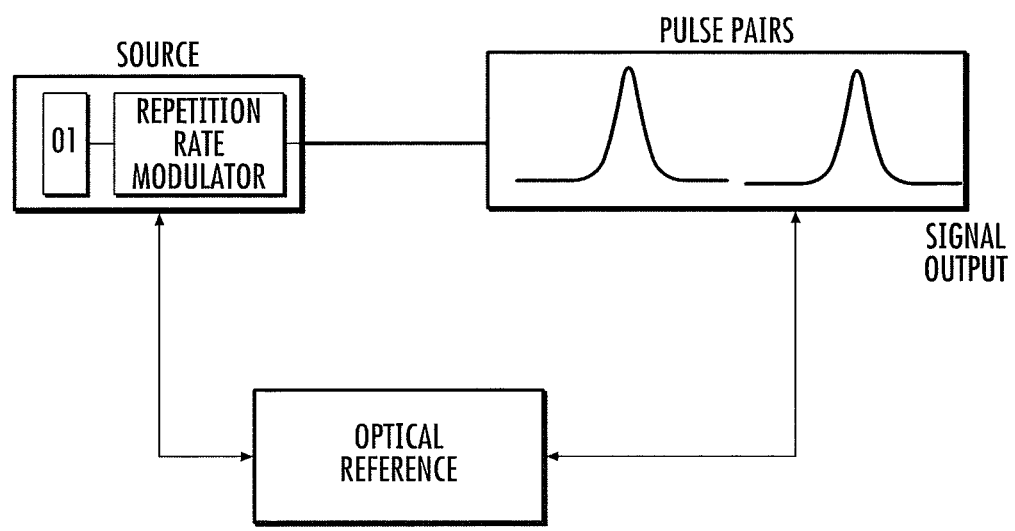
FIG. 16a is a schematic diagram illustrating the generic design of a CSL including an optical reference.

An example configuration of a generic coherent scanning laser system including repetition rate modulation is shown in FIG. 16a. In this example a source is configured for repetition rate modulation. The modulation frequency is preferably higher than 1 Hz, it can be higher than 10 Hz, and even higher than 1 kHz, depending on the application. In some applications, modulation frequencies as low as 10 mHz (millihertz) and even lower can be implemented also. At such low modulation frequencies optical referencing, as discussed with respect to FIG. 16, can be conveniently used to measure and correct for random repetition rate and carrier envelope offset frequency variations. Such coherent scanning delay lines can be used in Fourier transform spectroscopy and other applications. Oscillator repetition rates can be in the range from 5 MHz-10 GHz, and in some embodiments several tens of MHz or higher. The oscillator is part of an optical source, which is further configured to generate pulse pairs. These pulse pairs can, for example, be generated by using an optical delay line inside the source (not shown) with differential propagation lengths. Alternatively, a second oscillator can be added to the source, as already discussed with respect to FIG. 1. The repetition rate of the second oscillator can be approximately constant. At least one optical reference is then configured to measure the pulse pair delay (the time span between the two pulses comprising the pulse pair), and in some embodiments may also be used to measure the difference in the carrier envelope phase between the two pulses. For example in FIG. 16, such an optical reference can comprise one or two cw reference lasers, although any other form of optical reference can also be implemented. The interferogram generated by the pulse pairs is further detected by at least one detector (not shown), sampled and used to calculate an optical spectrum as in conventional Fourier transform spectroscopy. Information from the interaction of the optical reference with either/or both the repetition rate modulator and the pulse pair is further used for an analysis of the interferogram. In some configurations, the optical reference can be used only for calibration purposes and the analysis of the interferogram can proceed without continued use of the optical reference.

Figure 17A:
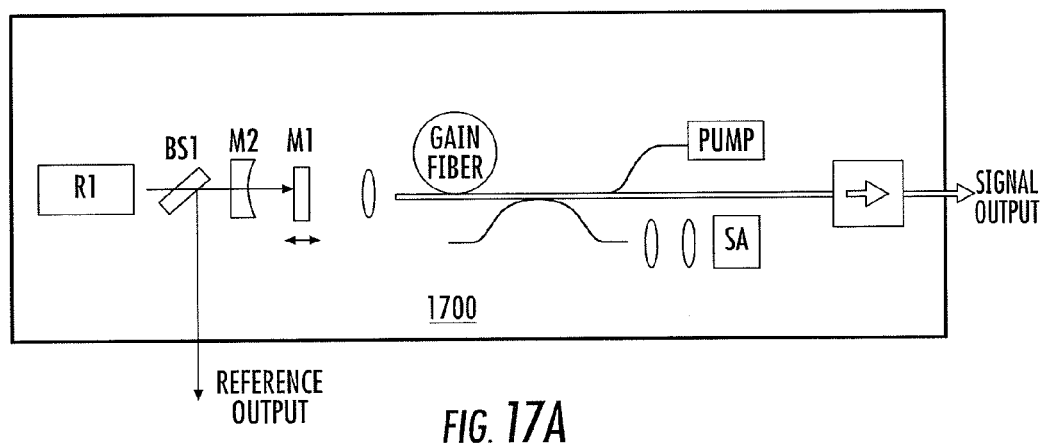
FIG. 17A is a diagram schematically illustrating a mode locked oscillator design suitable for use in a CSL incorporating optical referencing with an external laser.

FIG. 17A schematically illustrates an oscillator design 1700 for a coherent scanning laser system according to one embodiment. The oscillator is based on a Fabry-Perot cavity and comprises a gain fiber, doped for example with Er, Yb, Tm, Ho or Bi, and pumped by a pump source. The oscillator includes a saturable absorber mirror (SA) incorporated at one end of the cavity to initiate mode-locking, and a reflective mirror (M1) at the second end of the cavity. Dispersion compensation elements such as bulk grating pairs can also be inserted into the cavity, for example in front of the saturable absorber. Modification of the light propagation through such grating pairs can further be used for rapid control of the carrier envelope offset frequency of such oscillators. The pump light and the oscillator (signal) output are obtained via the incorporation of appropriate fiber couplers, as well known in the state of the art. The spatial position of mirror M1 and the repetition rate of the cavity can be modulated by mounting M1 for example onto a piezo-electric transducer, or by using a reflective M(O)EMS [micro-(opto)-electromechanical system] element. However, any other suitable arrangement for repetition rate modulation can also be used. For example an acousto-optic or electro-optic modulator can also be incorporated into the cavity. Also, the reference laser can be directed towards mirror M1 from the intra-cavity side using appropriate dichroic beam splitters, where different wavelengths for the oscillating signal and the reference laser are chosen.

The oscillator system of this example further includes a measurement system for measuring the spatial position of M1. For example, M1 can be combined with a second stationary mirror M2 to construct a Fabry-Perot reference cavity. When observing the reflection of a single frequency laser R1 from the reference cavity the spatial position of mirror M1 can be accurately measured, as well known in the state of the art. Alternatively, a reference Michelson interferometer can be constructed by removing M2 and incorporating another stationary mirror to observe an interference pattern at the reference output. Such a reference system is not separately shown. Such reference systems for measuring the location of mirrors are known from standard Fourier transform spectroscopy and are not further discussed here.

Figure 18:
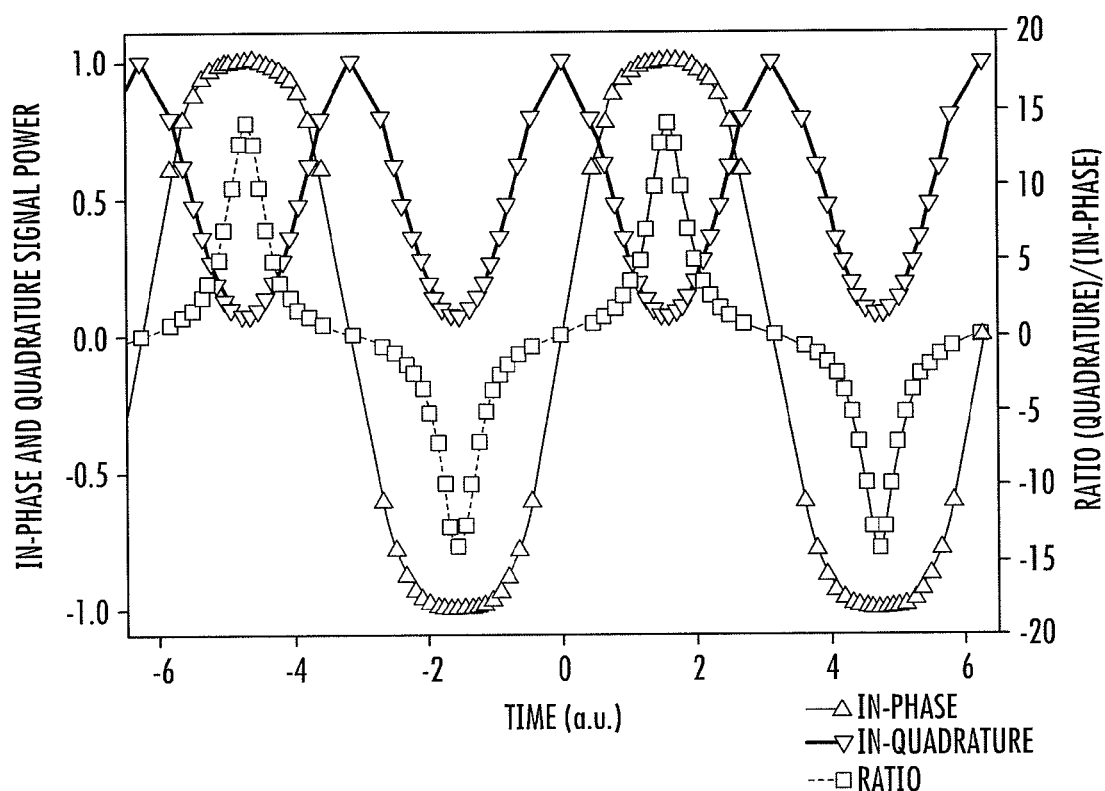
FIG. 18 is a diagram illustrating in-phase (triangles up) and quadrature-phase (triangles down) reference signals as well as their ratio (square) obtainable from a reference interferometer configured to probe the mirror position of a repetition rate modulated mode locked oscillator.

A reference output from a reference Michelson interferometer as a function of time assuming a sinusoidal modulation of mirror M1 is shown in FIG. 18. Here the DC part of the signal is subtracted, which can be accomplished using dual balanced detection as well known in the state of the art. In addition to the shown exemplary in-phase signal, a quadrature signal, a signal phase shifted by 90°, can also be simultaneously measured by the incorporation of an appropriate phase plate in one arm of the Michelson interferometer. An exemplary quadrature signal is also shown in FIG. 18. Such detection schemes are well known in the state of the art and are for example described in FIG. 10.4 of 'Building Electro-Optical Systems' by P. C. D. Hobbs, John Wiley&Sons (2000) and are not further described here.

Figure 17B:
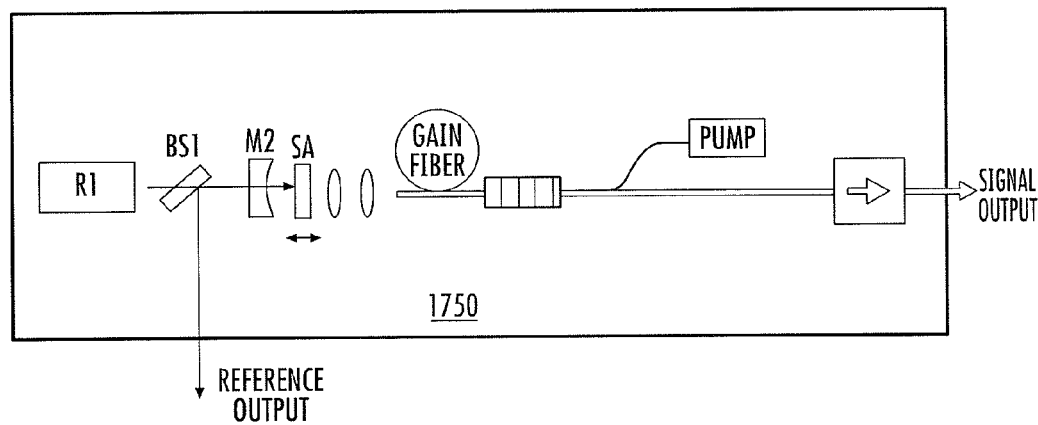
FIG. 17B is a diagram schematically illustrating an alternative mode locked oscillator design suitable for use in a CSL incorporating optical referencing with an external laser.

In FIG. 17B is an alternative configuration for an oscillator design 1750 for a coherent CSL according to another embodiment. Here a Fabry-Perot cavity constructed using a fiber Bragg grating as one cavity mirror and a saturable absorber mirror as the second cavity mirror is shown. Such oscillator designs were for example described in U.S. Pat. No. 7,190,705 to Fermann et al. and are not further discussed here. In this example the spatial position of the saturable absorber mirror can be modulated and the position of the saturable absorber mirror can be measured using similar schemes as discussed with respect to FIG. 17A. Other arrangements for cavity length modulation as discussed with respect to FIG. 17A can also be implemented. Other oscillator designs can also be used. In addition, frequency broadening, pulse compression and dispersion compensation stages can be implemented after the oscillator output as for example discussed with respect to FIGS. 1 and 16 and in '435. Such a frequency broadening stage can for example also comprise a synchronously pumped optical parametric oscillator (OPO). When using a CSL, the OPO cavity length can be modulated synchronously to the repetition rate of the (seed) oscillator. As discussed with respect to FIG. 7, such an OPO can also include a gas cell for sensitive gas measurements.

Figure 19:
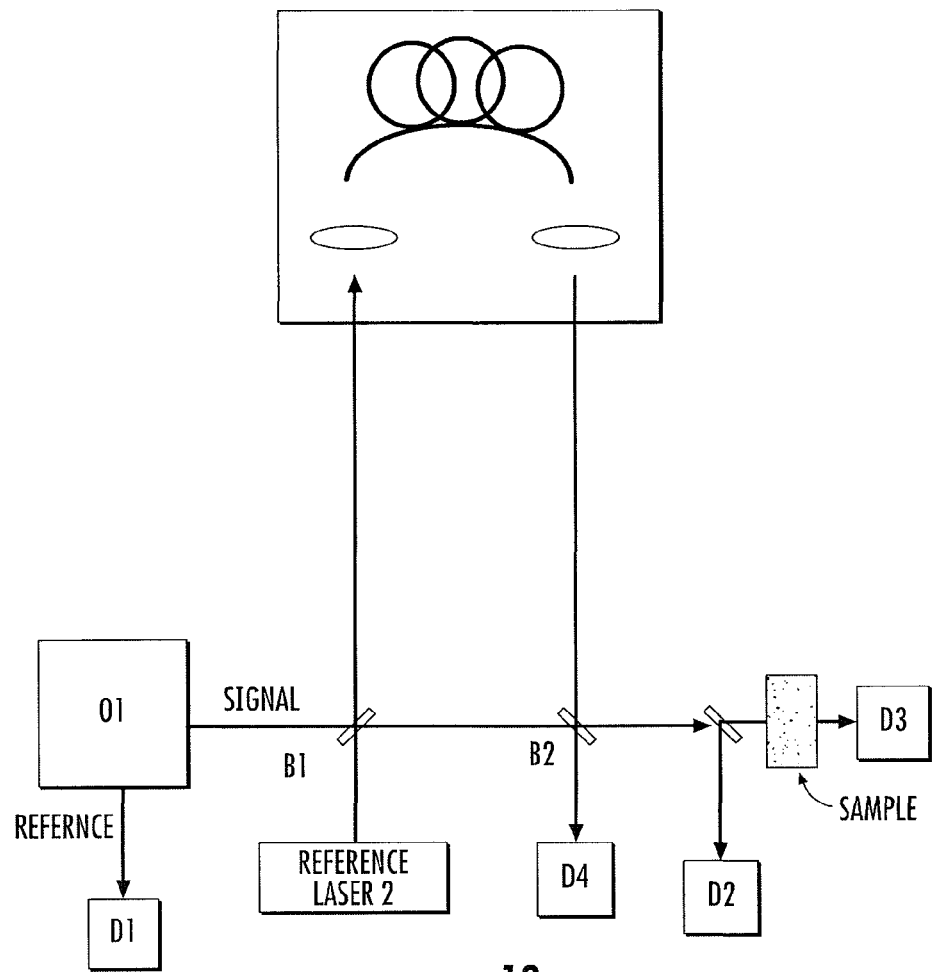
FIG. 19 is a schematic representation of a FTS based on a CSL including optical referencing.

FIG. 19 shows another exemplary configuration of a FTS based on oscillator designs as discussed with respect to FIGS. 17A and 17B. Other oscillator designs can also be used. In addition frequency broadening, via an OPO, pulse compression and dispersion compensation stages can be implemented after the oscillator output as discussed with respect to FIGS. 1 and 16. An FTS probes a physical property of the sample using spectral information in the emission envelope of the CSL. Here an optical delay line producing a time delay $T_d$ is incorporated, which produces two time delayed pulses at beam splitter B2.

For a sinusoidal mirror modulation at a frequency $f_M = 1/T_M$ $$x(t) = \frac{\Delta x}{2} \sin\left(\frac{2\pi t}{T_M}\right),$$

and further assuming $T_M = 2T_d$, where $T_d$ is the propagation time through the optical delay line, we obtain a spatial pulse delay at beam splitter B2 as a function of time which is given approximately by $$x_{tot}(t) = \frac{2\Delta x}{\pi} \frac{T_D}{T_L} \cos\left[\frac{\pi t}{T_D}\right],$$

where $T_L$ is the round-trip time of the oscillator. Hence any movement of the cavity mirror is amplified by a factor of $(2/\pi)T_D/T_L$. In this case the mirror modulation and the generated time delay between the two pulses are 90° out of phase. Here it was assumed that for x(t)=0, the pulses overlap perfectly in time and phase at beam-splitter B2.

As well known in traditional Fourier transform spectroscopy, in order to obtain spectral information from an interferogram, uniform sampling of the interferogram is preferable. Uniform sampling means that the time delay between the two interfering signals increases by a constant factor between two sample points. In conventional Fourier transform spectroscopy this is sometimes referred to as sampling at equidistant optical path length differences. In embodiments of CSLs utilizing sinusoidal mirror modulation the criteria does not apply.

However, in a CSL configuration utilizing sinusoidal, or other similar functions, a uniform time delay between the two pulses at beam splitter B2 can be obtained by the implementation of a non-uniform sampling grid to compensate for the modulation. Such a non-uniform sampling grid can, for example, be generated from the reference interferogram obtained at the reference output of oscillators of FIGS. 17A and 17B. For sinusoidal mirror position variations, the reference interferogram produces an output cos(x(t)+φ), where x(t) is time dependent and φ is a phase offset determined by the location of the stationary mirror in the reference interferometer. By measuring the in-phase and quadrature-phase outputs, tan(x(t)+φ) can be calculated and x(t)+φ estimated; moreover for simplicity we further assume that the stationary mirror is adjusted such that φ=0; alternatively φ can be recorded and compensated. An exemplary function tan(x(t)+φ) obtained from exemplary in-phase and quadrature signals is also shown in FIG. 18. The pulse delay at beam splitter B2 can then be obtained, which allows for the calculation of an appropriate sampling grid with the requirement of uniform increments of pulse delay between sampling points. Any other suitable method for obtaining a uniform sampling grid can also be implemented. Some examples of methods for equidistant optical path length sampling were for example described in S. A. Roy et al., 'Hybrid sampling approach for imaging Fourier-transform spectrometry', Applied Optics, vol. 46, pp. 8482-8487 (2007).

For the case of $T_M=2T_d$, when the mirror position is near zero, the preferred sampling points are widely spaced, whereas when the mirror position is at the end of the modulation range, narrow spacing of the sampling points is required. Optimum sampling points as a function of time for the exemplary in-phase and quadrature signals and their ratio are represented by the symbols in FIG. 18.

In some implementations, for example when using rapidly modulated mirrors, MEMS or MOEMS element, or when using electro-optic cavity length modulation, the mirror positional variations achieved with a certain applied modulation signal can also be calibrated once to produce a sampling grid which can then be repeatedly used for accurate sampling of interferograms generated between two pulses. Therefore continuous monitoring of the repetition rate and carrier envelope variations of the pulses is not required. In some embodiments such variations can be measured once (or at certain time intervals) and used for the interpretation of many subsequently acquired interferograms. This greatly reduces required signal processing times. Also, the accuracy of the obtained mirror positional variations can be checked and calibrated via the use of samples with known absorption lines or transmission or reflection properties.

A particularly simple method for obtaining a uniform sampling grid is to filter the source spectrum with a narrow bandpass optical filter. Such filtering may be carried out after propagation through the optical delay line and recombination at an optical beam splitter, for example as illustrated in FIG. 16. The phase of the optical beat frequency measured through the narrow bandpass optical filter is directly proportional to the optical path length differences between the two interfering pulses. The optical beat frequency can thus be electronically sampled and a digital sampling device can be directly triggered whenever the sinusoidal waveform generated by the optical beat frequency passes through zero. Such schemes for obtaining a uniform sampling grid are also well known from conventional Fourier transform spectroscopy. Moreover, the narrow bandpass optical filter can then also serve for absolute frequency calibration of the recorded interferograms. Additional drifts in the time delay between the pulses can also occur due to temperature and acoustically induced delay modifications. In principle the length of the optical delay line can be stabilized with well known techniques as discussed with respect to FIG. 16 and also in K. Holman, D. Hudson, J. Ye and D. J. Jones., Opt. Lett., vol. 30, pp. 1225-1227 (2005). Fiber length stabilization as discussed by Holman et al., involves a comparison of the pulse train before and after transmission though the optical delay line using two detectors. Appropriate mixing of the detector signals allows measurement of phase fluctuations between the detectors; the detected phase noise is then fed back to fiber length modulators for active fiber length stabilization. Alternatively, a second reference laser (reference laser 2) as shown in FIG. 19 can be coupled into the imbalanced Mach-Zehnder interferometer via B1 and path length variations can be recorded and compensated via observing an interference signal of the second reference laser at beam-splitter B2 on detector D4. Any other form of a length stabilizer for recording of the path length variations of the optical delay line can also be implemented. To first order, modulation of the cavity end mirror position does not affect the carrier envelope offset frequency of the laser, which simplifies the implementation of such cavity length modulation schemes in coherent scanning delay lines.

In addition to the use of reference lasers as explained here for the generation of an optimum sampling grid, an f-2f interferometer can further be incorporated to measure and correct for possible carrier-envelope offset frequency fluctuations during mirror modulation. Moreover, various techniques and feedback systems for controlling carrier-envelope offset frequency fluctuations are disclosed in '859.

Also, as explained with respect to FIG. 1, FIG. 16 and '435, additionally the beat of the mode locked laser with two reference lasers can be implemented to measure and compensate for carrier envelope offset frequency and time delay fluctuations after beamsplitter B2. These reference lasers can be configured to interfere with the laser pulses either before or after the optical delay line or both and can also be configured to interfere with the laser pulses after beamsplitter B2. In addition the interferogram obtained at beamsplitter B2 can be filtered with two narrow band filters such as fiber gratings in order to measure and compensate for carrier envelope offset frequency and time delay fluctuations. Optical reference filters can also be introduced before or after the optical delay line or both. Optical referencing with optical filters was discussed in Giacarri et al., 'Referencing of the beating spectra of frequency combs' (International Patent Application, Publication WO 2009/000079) and is not further described here.

Figure 20:
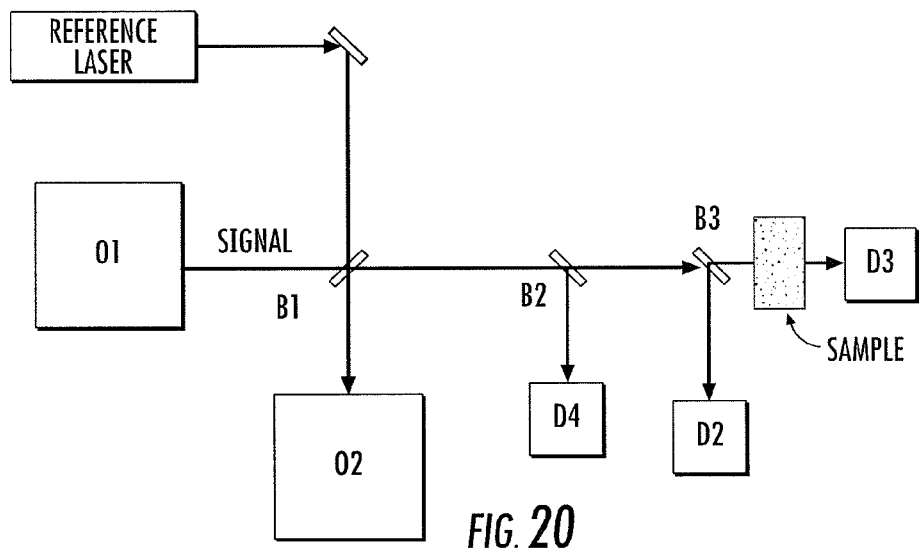
FIG. 20 is a schematic representation of a CDSL including an optical reference configured for FTS.

In addition to using a single laser CSL a dual laser coherent scanning delay line (CDSL) can also be implemented for precision FTS, as shown in FIG. 20. Such CDSLs were also discussed with respect to FIG. 1. In order to optimize the performance of such CDSLs, it is often desirable to modulate or dither the repetition rate of one laser versus the other, as for example discussed in U.S. Pat. Nos. 5,778,016 and 6,393,856 to G. Sucha et al. For sinusoidal cavity length modulation, the same considerations for optimum sampling point distribution as for a CSL also apply.

Optical referencing as discussed with respect to FIG. 1 can then be implemented to track the repetition rate and carrier envelope offset frequency modulations of the two mode locked lasers. Alternatively, external reference lasers can be implemented as discussed with respect to FIG. 16. A CDSL including repetition rate dithering and optical referencing is shown in FIG. 20. Here O1 is constructed with a modulated cavity mirror, whereas O2 is constructed with a fixed cavity mirror. For fast modulation rates, random fluctuations of the laser repetition rate and carrier envelope offset frequency can be neglected, which means the variations in relative pulse delay at beam splitter B3 can be inferred from a measurement of the mirror position. The modulation of the laser repetition rates and fluctuations of the carrier envelope offset frequency can further be tracked and compensated for with the implementation of cw reference lasers and/or narrow bandpass filters as discussed with respect to FIG. 19 and with respect to FIG. 1.

When implementing repetition rate dithering it is beneficial to make sure that the time delay between the pulses dithers around the same reference point. The time intervals between pulse crossing events will be held approximately constant.

Figure 19A:
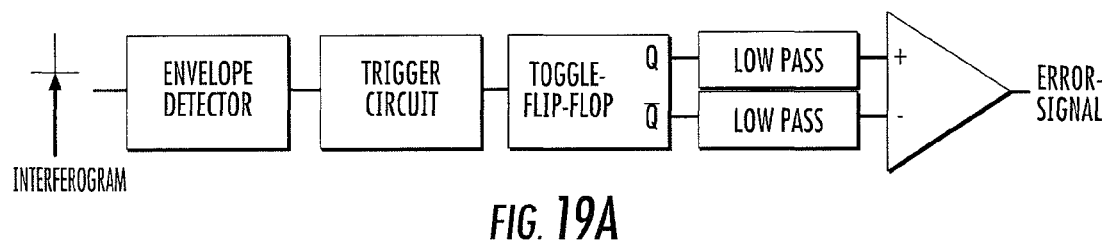
FIG. 19A is a schematic representation of an electronic scheme for centering the zero-delay point during repetition rate dithering.

FIG. 19A shows a preferred embodiment of a feedback circuit which is used for centering the zero-delay point during repetition rate dithering, the individual signals are schematically shown in FIG. 19B. The delay between O1 and O2 during repetition rate dithering is shown as a function of time in FIG. 19B, plot A. In the depicted example the scan is not symmetric to the zero-delay point, which is indicated by the dashed horizontal line. At all zero-delay points an interferogram is detected (FIG. 19B, plot B) which is further processed in an envelope detector (FIG. 19B, plot C). A trigger circuit detects all positive edge-crossings of the envelope at a set trigger level (FIG. 19B, plot C). Those trigger events change the state of a flip flop (FIG. 10B, plot D). The output Q as well the inverted output $\overline{Q}$ of the flip-flop is low-pass filtered and compared, generating an error signal. This error-signal can be used to change the duty-cycle of the dithering, which advances one oscillator, for example e.g. O1, with respect to the other (O2) and therefore centers the dither-range with respect to zero delay. When the dither-range is centered the error signal is zero. There is a sign ambiguity in the feedback signal which can be resolved by changing the sign if the magnitude of the error signal does not decrease after closing the loop. In various embodiments other techniques for the stabilization of the time intervals between pulse crossing events can also be implemented. Some techniques for the stabilization of these time intervals were discussed, for example, in U.S. Pat. No. 6,396,856.

When implementing frequency broadening stages in various embodiments of CSLs and CDSLs, nonlinear interactions between the two interfering pulses are to be considered. One way to avoid nonlinear interactions was already discussed in '435, where frequency broadening of two time-delayed pulses was described, which are subsequently overlapped in time with an imbalanced Mach-Zehnder interferometer, such a scheme is not separately shown here. The same principle is also applicable to CSL and CDSLs that incorporate repetition rate modulation. Alternatively, the two pulses can be time delayed and propagated along two different polarization axes in the frequency broadening stage and later recombined by the introduction of a polarization dependent group delay. Any other methods for the introduction and compensation of a group delay between the two interfering pulses can be implemented.

Referring again to FIG. 19, and when implementing a CSL, nonlinear frequency broadening stages can be conveniently introduced before the pulses are split at beamsplitter B1. Thus nonlinear interactions are avoided between the interfering pulses. In various embodiments it is advantageous to use a low-dispersion optical delay line such as a Herriott cell as discussed above, for example with respect to FIG. 16, to generate time varying optical path delays. When implementing difference frequency mixing in the nonlinear frequency broadening stages, the carrier-envelope offset frequency can be set to zero, greatly simplifying the interpretation of the measured interferograms.

CSLs and CDSLs can be used in many different applications, comprising pump probe spectroscopy, optical coherence tomography (OCT), LIDAR and optical sampling and any other application requiring two pulses with a varying time delay as for example described in G. Sucha et al. U.S. Pat. No. 5,778,016.

Figure 21:
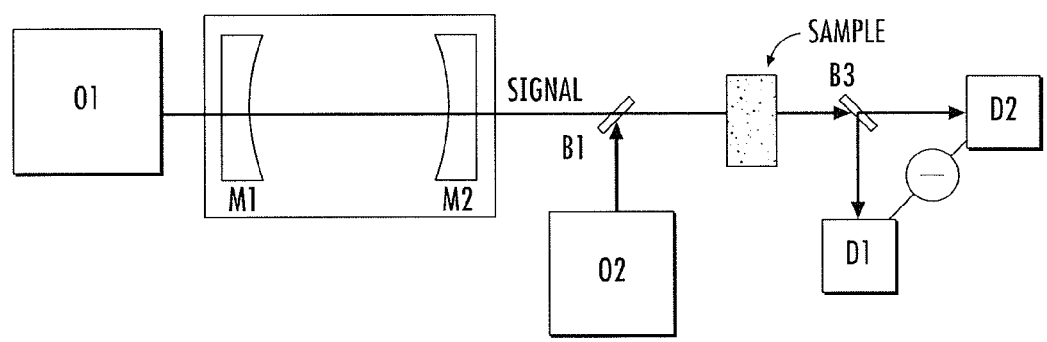
FIG. 21 is a schematic representation of a CDSL incorporating repetition rate multiplication.

As an alternative to modulations of the laser repetition rate, the signal acquisition rate can also be increased by the implementation of repetition rate multiplication via the use of enhancement cavities. An example of an enhancement cavity was discussed with respect to FIG. 7. An exemplary system design including repetition rate multiplication is shown in FIG. 21. Repetition rate multiplication using enhancement cavities was for example discussed by T. Sizer in 'Increase in laser repetition rate by spectral selection', IEEE J. Quantum Electronics, vol. 25, pp. 97-103 (1989) and the application of such cavities to FTS was also discussed herein with respect to FIG. 7, where appropriate methods for stabilizing the carrier envelope offset frequencies and repetition rates of both oscillators were also discussed. In FIG. 21, the round trip time of the enhancement cavity $T_c$, bordered by mirrors M1 and M2, is selected to be a fraction of the round-trip time $T_{O1}$ of oscillator O1, where $T_{O1}=N \times T_c$. As discussed with respect to FIG. 7 and also U.S. patent application Ser. No. 11/546,998, appropriate phase control and repetition rate control can be implemented with oscillator O1 to optimally match its phase and repetition rate to the enhancement cavity.

Here a Fabry-Perot enhancement cavity is shown but any other cavity design may also be implemented. Also frequency broadening and pulse compression stages may be implemented downstream of the oscillators. The cavity effectively increases the repetition rate of oscillator O1, resulting in a pulse repetition rate of $1/T_c$. Hence, the possible signal acquisition rate of interferograms detected with balanced detectors D1 and D2 is increased by a factor of $T_{O1}/T_c$ compared to the case without an enhancement cavity. Though here repetition rate multiplication for only one oscillator is shown, in principle repetition rate multiplication for both oscillators may be implemented using, for example, two enhancement cavities.

Figure 22:
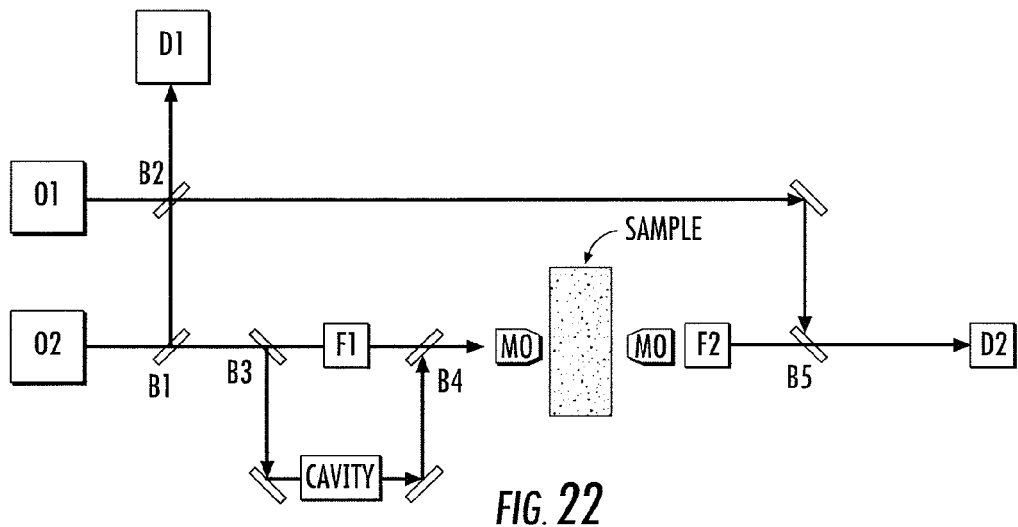
FIG. 22 is a schematic representation of a CDSL for pump probe experiments and imaging incorporating repetition rate multiplication.

A CDSL configured for measurement of stimulated emission spectra was discussed with respect to FIG. 12. An alternative configuration of a CDSL incorporating repetition rate multiplication is shown in FIG. 22. Here oscillators O1 and O2 generate broad bandwidth pulses, which may span a significant portion of an octave. The broad bandwidth pulses can further be amplified and spectrally broadened (not shown). The oscillators are configured to operate at slightly different repetition rates and the carrier envelope offset frequency of both oscillators can further be controlled. In this example the output of oscillators O1 and O2 is directed via beam splitters B1 and B2 onto detector D1 to obtain a reference spectrum. In the following we refer to the unfiltered pulses from oscillator O2 as test pulses. A fraction of the test pulse output of oscillator O2 is further passed through a narrow bandpass filter F1 to generate pump pulses. The pump pulses can further be amplified, which is not separately shown. The repetition rate of the test pulses from O2 is then multiplied by the shown cavity, where conveniently a multiplication factor of two is sufficient. Repetition rate multiplication can also occur before frequency broadening. The pump pulses from O2 and the test pulses from O2 are further combined with beamsplitter 4 and directed onto the test sample via a microscope objective, where temporal overlap on the test sample is ensured. A notch filter, F2, then filters out the narrow pump pulses collected by another microscope objective so that broad bandwidth test pulses are transmitted to detector D2, where they are also combined with the output from oscillator O1 via beamsplitter B5. For strong pump pulses, stimulated Raman scattering emission leads to an amplification (or attenuation) of certain spectral bands inside the test pulses. Spatially resolved information is generated via changing the position of the test sample between the two microscope objectives.

In FIG. 22 an arrangement for transmission measurements is shown. A similar arrangement can also be used for reflection measurements with modifications of the optical system. In some embodiments both reflection and transmission measurements may be obtained. Both oscillators can further be pumped by the same pump laser for noise reduction and improved signal/noise ratios can be obtained via the implementation of dual balanced detection schemes.

The use of the enhancement cavity effectively doubles the possible signal acquisition rate, since only every other test pulse gets perturbed by the pump pulses. By subtracting the test pulse spectra detected with pump pulses on and off, an accurate measurement of the stimulated Raman emission spectrum can be readily obtained.

Figure 23:
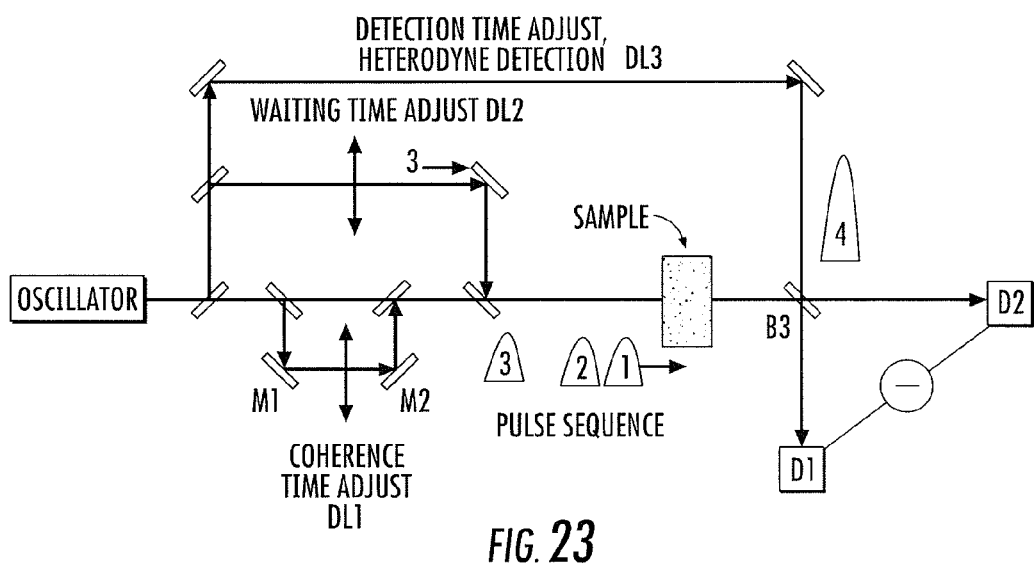
FIG. 23 is a schematic representation of a CSL for two-dimensional spectroscopy applications.

Although we discussed probe pulse modification by only one pump pulse in a collinear arrangement with respect to FIG. 22, in principle any number of pump pulses can be used and a collinear arrangement between probe and oscillator pulses is not required in order to observe probe modifications with a local oscillator reference pulse in a CDSL or a CSL arrangement. In particular, a CSL can also be implemented for general two dimensional spectroscopy. A possible configuration for two-dimensional Fourier transform spectroscopy based on a CSL is shown in FIG. 23. Here an oscillator as described with respect to FIG. 17A or 17B, or any other mode locked oscillator with a modulated repetition rate, can be implemented.

The pulses from the oscillator or generally the signal source are split into a three pulse sequence (which is not necessarily collinear, i.e. a boxcar geometric configuration, as well known in the state of the art can be implemented) with an arrangement of two optical delay lines DL1 and DL2. In order to fix the delay between these pulses, the pulses are generated from one oscillator pulse. Such three pulse sequences for two-dimensional spectroscopy were for discussed with respect to FIG. 12A. Here the first optical delay allows for an adjustable time separation $\tau$ between the first two pulses, the so-called coherence time adjustment $\tau$ in Hochstrasser. The second optical delay line allows for an adjustment of the time separation of the third pulse with respect to the first two pulses, the so-called waiting time adjustment T in Hochstrasser. These three pulses can then generate a photon echo signal pulse which is optically sampled as a function of time t (the so-called detection time in Hochstrasser) with the oscillator pulses delayed by delay line DL3, and detected with detectors D1 and D2.

Delay line DL3 is configured to generate a pulse 4 which is configured to interfere with pulses 1-3 after a time corresponding to at least several oscillator round-trip times to produce a time-varying pulse delay. In principle any of other delay lines can also be configured in such a fashion, which allows for the generation of time dependent pulse delays between pulses 1-3 without any moving parts.

The resulting time domain interferogram produced with the delay lines can be Fourier transformed along variables t and $\tau$ in order to yield two-dimensional absorption spectra. Instead of a single read out pulse 3, a sequence of read out pulses can also be implemented. Also the first two pulses can be modulated to increase the sensitivity of the measurement. In addition the transmission of pulse three can be directly measured with the first two pulses being on and off.

Such two-dimensional absorption spectra are highly useful for the analysis of complex molecular structures as for example discussed by Hochstrasser. Because of the great improvement in acquisition speeds possible for two-dimensional spectroscopy with the arrangement shown in FIG. 23 compared to conventional two-dimensional spectroscopy as discussed by Hochstrasser, the pump probe arrangement as discussed with respect to the examples of FIG. 23 is further adaptable to optical imaging applications and microscopy, by implementing appropriate focusing and optical scanning arrangements in front of the sample and behind the sample. Further modifications of the actual pulses as well as their spatial and temporal arrangement and sequencing as well as the implementation of larger number of pulse sequences are also possible, allowing for general multi-dimensional spectroscopic measurements.

Figure 24:
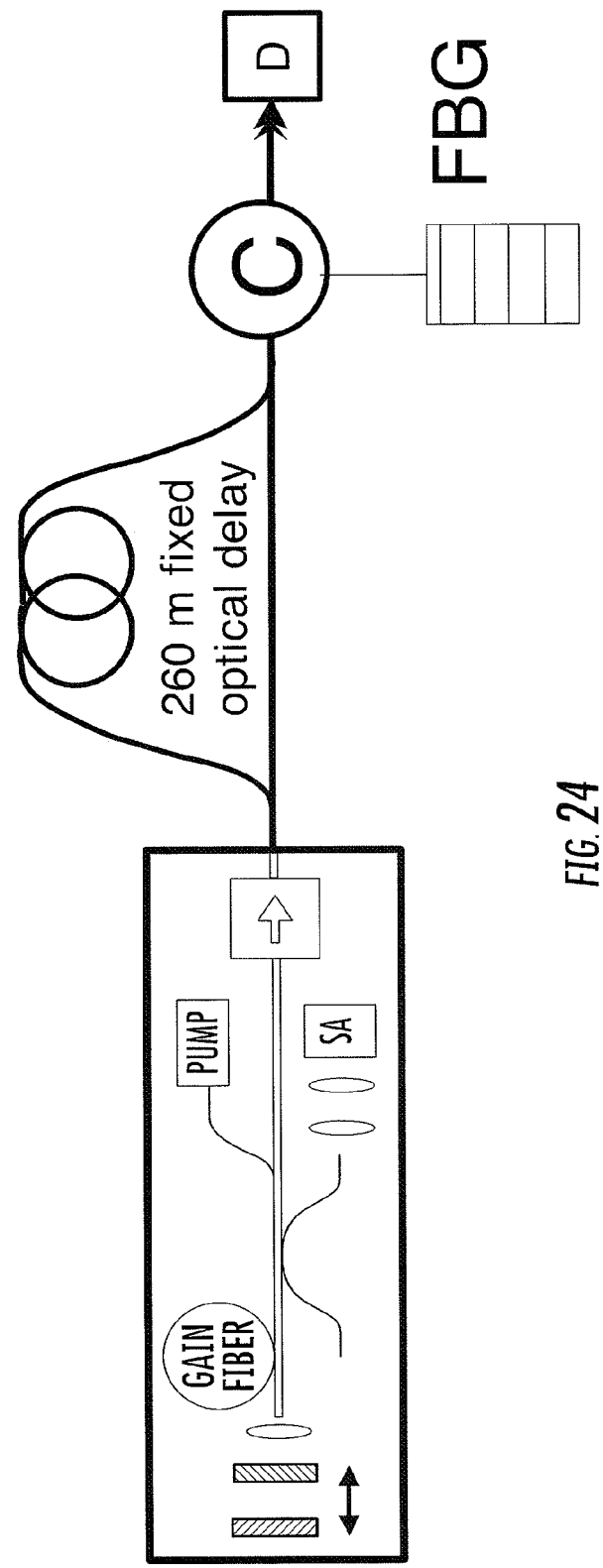
FIG. 24 is a schematic diagram illustrating an alternative embodiment of an effective CSL constructed with only one laser including optical referencing.

By way of example, a CSL, including optical referencing, was constructed by the inventors. A design example is shown in FIG. 24. Here the comb laser was constructed as shown in FIG. 17A, with some exceptions as discussed below. First, a separate reference laser R1 was not used and rather a fiber Bragg grating (FBG) was used for optical referencing, and disposed downstream from the comb laser. The mirror pair M1-M2 of FIG. 17A was also replaced by a single intra-cavity moving mirror, shown in FIG. 24. at the limits of the travel range (depicted by the arrow). Also, a highly Yb-doped fiber was used as the gain fiber with a length of 6 cm, and pumped with a 980 nm laser diode. In addition, dispersion compensation elements (not shown) were inserted in front of the SA inside the oscillator corresponding to FIG. 17A. In this example the dispersion compensating element comprised two bulk transmission gratings with groove density of 600 l/mm. The arrangement of the gain fiber, pump, isolator, and delivery optics was otherwise as schematically illustrated in FIG. 17A.

The fiber Bragg grating is shown as FBG in FIG. 24 and is connected to the circulator C. The output from the fixed delay line is coupled into the circulator, and then reflected out of the FBG and detected with detector D. The laser produced approximately 100 fs pulses with a spectral bandwidth of 20 nm when operating the laser near the zero dispersion point with an output power of 10 mW at a repetition rate of 60 MHz. The center wavelength was 1030 nm. The intra-cavity moving mirror was mounted on a piezo-electric transducer (PZT) having an absolute travel range of around 10 μm, although only 1.25 μm travel range was used here at a modulation frequency of 1 kHz. The moving mirror is schematically illustrated in FIG. 24 with the two rectangles and an arrow below. The shown enclosure of the two rectangles contains all the components from FIG. 17A with the exceptions as discussed above. The cavity length modulations were increased 8 fold to a total cavity length modulation of ±5 μm by optical folding, using moving mirror M1 as well as two stationary mirrors (not shown). The optical delay line had a length of approximately 260 m and thus the path length modulation increased the possible pulse separations by approximately a factor of 50 compared to the cavity length modulations. Thus the maximum achievable pulse delay at the fiber Bragg grating was around 0.25 mm. The dispersion in the optical delay line was further compensated with a fiber Bragg grating, though dispersion compensation of the optical delay line is not absolutely required.

Figure 25:
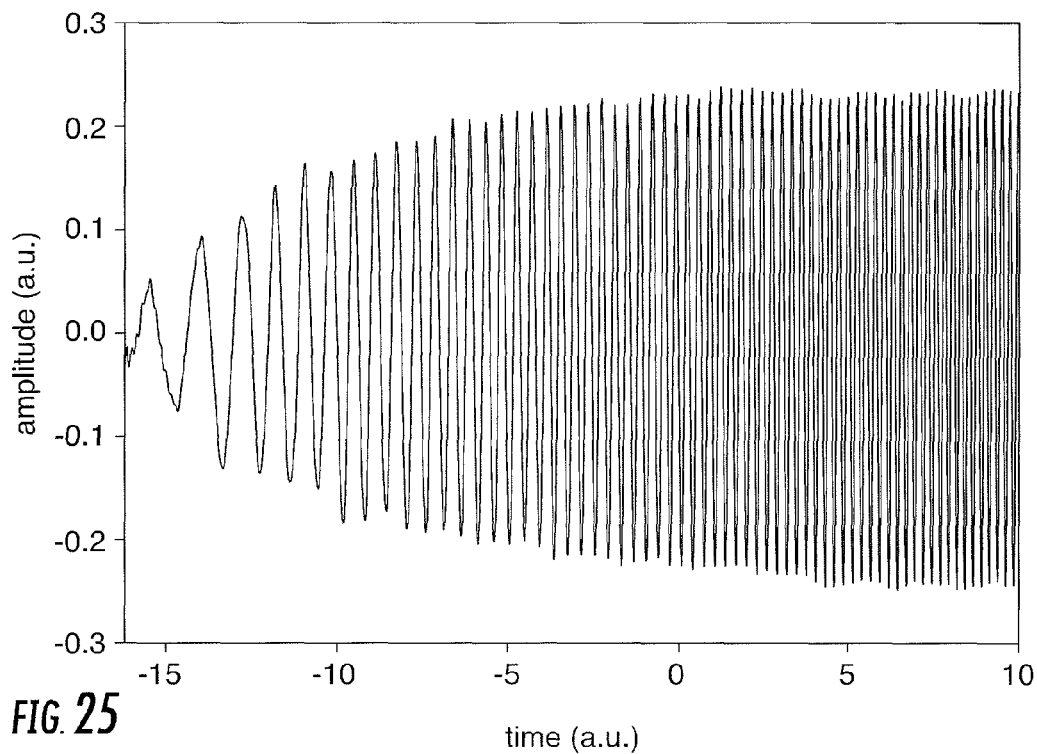
FIG. 25 is a plot illustrating a measurement of an interferogram recorded with a CSL.

The interferogram recorded via detector D via an optical sampling device is shown in FIG. 25. The start of the interferogram coincides with the turning point of the PZT. The amplitude of the interferogram is lower at the beginning due to the presence of a low pass RF filter. Any amplitude modulation that can occur from tilt movement away from a linear axis during PZT oscillation needs to be minimized. Such amplitude modulations can induce relaxation oscillations in the oscillator and lead to large variations of the carrier-envelope offset frequency. For the recording of an actual interferogram the zero-point crossings of the shown reference interferogram can be used to trigger an actual sampling device. Frequency doubling of the reference pulses can further be implemented to increase the accuracy of the sampling points.

Figure 26:
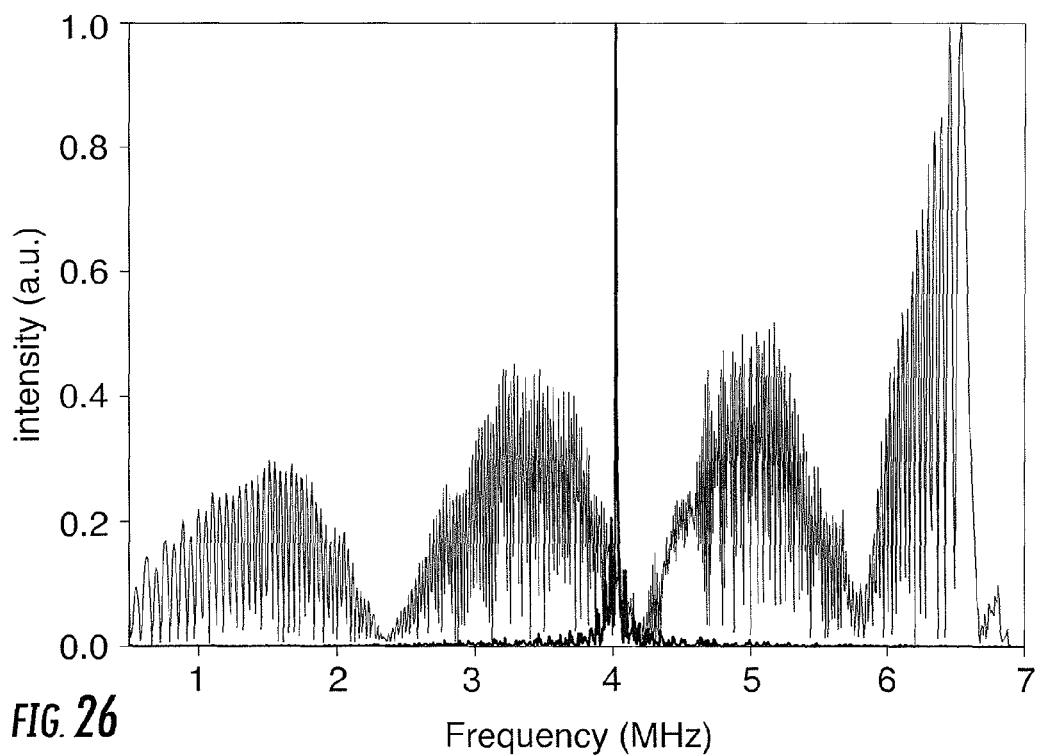
FIG. 26 is a plot illustrating measurement of a frequency spectrum of an interferogram recorded with a CSL (thin line) and of a corrected frequency spectrum (thick line) accounting for fluctuations in intra-cavity mirror velocity.

The Fourier transform obtained from the interferogram is shown in FIG. 26. Here the broad spectrum corresponds to the Fourier transform of the uncorrected interferogram, whereas the narrow spectrum corresponds to the Fourier transform of the interferogram corrected for equidistant optical path length differences between sampling points. The bandwidth of the Fourier transform correction corresponds to $1/500^{th}$ of the central frequency (4 MHz), as expected from the recording of 500 fringes at 1 μm. In optical frequency the resolution thus corresponds to 20 cm$^{-1}$ or around 2 nm. It was further verified that a calibration of a mirror movement obtained with one interferogram could be used for the correction of other interferograms. This is due to the high frequency of oscillation of the PZT which leads to preferential sinusoidal excitation of mechanical vibrations in the PZT with only 2 or 3 higher harmonics of significantly lower amplitude which are highly reproducible from oscillation period to oscillation period. With state of the art PZT stages, cavity length modulations of up to 20 µm can be expected at oscillation frequencies up to a few kHz. With state of the art electro-mechanical voice coils, mirror movements up to 100 µm travel at kHz repetition rates are possible, whereas MEMS mirrors can achieve up to 1 mm travel range at 1 kHz. With mode locked oscillators operating at a few hundred MHz repetition rate and optical delay lengths of a few hundred meters, optical frequency resolutions<1 cm$^{-1}$ can be obtained. Optical frequency resolutions<0.1 cm$^{-1}$ and <0.01 cm$^{-1}$ can be obtained with optimally designed systems. At scan rates of 10-100 Hz travel ranges from moving mirrors up to 1 mm are suitable, with oscillators operating at several hundred MHz repetition rates, magnified scan ranges in the m range are suitable at these lower scan frequencies. Note that by recording an interferogram via the fiber Bragg grating FBG, length fluctuations of the delay line as well as timing jitter between the two interfering pulses are also recorded, since the zero crossing points of the interferogram correspond to points of equal optical path length differences between the two optical pulses. By using two interfering pulses from the same oscillator, the interfering pulses become strongly correlated and thus any carrier envelope fluctuations between these two pulses can also be greatly reduced. Thus high spectral resolution measurements with only one fiber Bragg grating used as an optical reference become possible. The resolution can further be enhanced by using an etalon in conjunction with the fiber Bragg grating or by also using one or two cw reference lasers for optical referencing as discussed earlier with respect to FIG. 16.

Thus the inventors have described CDSLs, effective CDSLs, CSLs, and some applications thereof, and various alternatives for implementation including highly integrated configurations.

At least one embodiment includes a coherent dual scanning laser system (CDSL). The system includes first and second passively mode locked oscillators, the oscillators configured to operate at slightly different repetition rates, such that a difference $\delta f_r$ in repetition rates is small compared to the values $f_{r1}$ and $f_{r2}$ of the repetition rates of the first and second oscillators. The first oscillator generates multiple frequency lines separated by $f_{r1}$ within a first optical emission envelope and the second oscillator generates multiple frequency lines separated by $f_{r2}$ within a second optical emission envelope. The system also includes first and second cw reference lasers operating at respective cw reference frequencies $f_x$ and $f_y$, each of first and second cw reference lasers optically connected with each of the first and second oscillators, and producing outputs located within the emission envelope of each of the oscillators. The first cw reference laser has a frequency line separated by $f_{b1}$ from a frequency line of the first oscillator, and separated by $f_{b2}$ from a frequency line of the second oscillator. The second cw reference laser has a frequency line separated by $f_{b3}$ from a frequency line of the first oscillator and separated by $f_{b4}$ from a frequency line of the second oscillator. The cw reference lasers and the oscillators are arranged to generate RF beat frequencies corresponding to $\Delta f_2 = f_{b1} - f_{b2}$ and $\Delta f_1 = f_{b3} - f_{b4}$. The RF beat frequencies are locked to external RF reference signals via phase locked loops, for example.

In various embodiments a CDSL may include a non-linear frequency conversion section optically connected to each oscillator, and the section may include a non-linear optical element generating a broadband spectrum having a bandwidth substantially greater than an oscillator spectrum.

In various embodiments a nonlinear frequency conversion section may include an optical parametric oscillator.

In various embodiments an optical parametric oscillator may include a gas cell for trace gas detection.

In various embodiments the frequency conversion section includes an output section that receives and combines multiple input frequencies and generates a spectral output at a difference frequency thereof.

In various embodiments a CDSL is arranged as part of a FTS, wherein the FTS is utilized to probe a physical property of a test sample with spectral components within an oscillator emission envelope.

In various embodiments the CDSL is arranged with measurement or imaging equipment for one or more of optical imaging, microscopy, spectroscopy, micro-spectroscopy, THz imaging, emission spectroscopy, Raman spectroscopy, stimulated Raman spectroscopy, Raman spectroscopy imaging, and multidimensional spectroscopy.

In various embodiments measurement or imaging equipment comprises an element for optical scanning.

In various embodiments a CDSL includes a phase-locked loop to control the repetition rate of one of the oscillators.

In various embodiments a CDSL includes a phase locked loop and an f-2f interferometer to control a value of a carrier envelope offset frequency of one of the first and second oscillators.

In various embodiments a mode locked oscillator includes a mode locked solid-state, fiber or diode laser oscillator.

In various embodiments a mode locked oscillator includes a Nd, Yb, Tm, Er or Bi fiber oscillator.

In various embodiments at least one fiber amplifier amplifies one or more oscillator outputs.

In various embodiments a nonlinear frequency conversion section includes a difference frequency generator.

In various embodiments a non-linear frequency section includes a supercontinuum generator disposed downstream of at least one oscillator.

In various embodiments a means for monitoring the absolute value of a carrier envelope offset frequency of at least one of the two oscillators is provided, and the means may include detection and signal processing equipment, for example.

In various embodiments a means for monitoring at least the repetition rate of one or both of the oscillators is included, and the means may include a detector and signal processing equipment, for example.

In various embodiments beat frequencies, $\Delta f_{b1}$ and $\Delta f_{b2}$ are used to generate a frequency grid in the RF domain that has a one to one correspondence to a frequency grid in the optical domain.

In various embodiments two reference cavities are provided for frequency control of the cw lasers.

Various embodiments include an enhancement cavity matched in round-trip time to the repetition rate of one of the oscillators to improve the detection sensitivity of trace gases inserted into the cavity.

At least one embodiment includes a system having a CDSL; a material emitting THz radiation in response to an output of the CDSL; and a detector responsive to the THz radiation.

In various embodiments a CDSL generates trains of short optical pulses, and a system includes: a beam combiner for spatially combining trains of short optical pulses to propagate along a common optical path downstream of the beam combiner; a non-linear optical element for spectrally broadening at least one train of short optical pulses propagating along the common optical path; and a dual arm interferometer configured with different arm lengths so as to detect interference between pulse trains when the pulses are not temporally overlapping in time prior to entering the interferometer.

In various embodiments an arm length difference corresponds to approximately one-third of the cavity round trip time of first and second oscillators.

In various embodiments a CDSL includes: a beamsplitter for combining outputs of first and second oscillators; at least one detector for detecting the beat signal generated by combined oscillator outputs; and a signal processor receiving and processing the beat-signal, the beat signal representative of an absorption, emission or phase spectrum of a sample inserted into at least one of the optical paths of either oscillator output, upstream of the beam splitter.

In various embodiments a CDSL includes: a beamsplitter for combining the outputs of the oscillators; at least one detector detecting the beat signal generated by the combined oscillator outputs; a signal processor receiving and processing the beat-signal, the beat signal representative of an absorption, phase or emission spectrum of a sample inserted into optical paths of the combined oscillator outputs, downstream of the beam splitter.

In various embodiments a detector is arranged to record a beat spectrum for a time period which exceeds the inverse of the difference in repetition rates between the first and second oscillators.

In various embodiments a second detector is included for recording a reference spectrum.

In various embodiments a CDSL includes a second detector for recording the absorption or emission spectrum or phase response of a sample, the detection sensitivity being further enhanced via recording the difference in detection currents between the two detectors.

In various embodiments a CDSL includes: an optical amplifier having polarization axes, the amplifier disposed downstream from the first and second oscillators. The CDSL also includes a nonlinear frequency conversion section having polarization axes corresponding with the axes of the amplifier, the section optically connected to an output of the amplifier and generating amplified and frequency converted outputs. The oscillators are arranged to propagate respective oscillator outputs along different polarization axes of the amplifier, and along corresponding polarization axes of the nonlinear frequency conversion section. A polarization beam splitter splits the amplified and frequency converted outputs along the two polarization axes. A beam splitter for interferometrically combining the amplified and frequency converted outputs along the two polarization axes is included, and the beam splitter for interferometrically combining is disposed downstream from the sample. Detectors detect the beat signal between the two oscillators along the two outputs of the beam splitter for interferometrically combining. A signal processor records the difference in detection currents between the two detectors.

Various embodiments include a dual balanced detection arrangement for recording one or more of absorption, emission and phase response of a sample in one or more of transmission and reflection.

In various embodiments two oscillators are pumped with a common pump laser.

In various embodiments a CDSL is configured to generate a strong pump and a weak probe beam from a first oscillator with an adjustable time delay between the pump and probe pulses, where a second oscillator is configured to produce a signal beam, the pump and probe beam coupled into a sample, and wherein a second oscillator is used to detect a change induced in a propagation characteristic of the probe beam, the change being induced by the pump beam.

In various embodiments propagation characteristics include phase or absorption changes.

In various embodiments propagation characteristics include time dependent phase or absorption changes.

In various embodiments a CDSL is arranged with a measurement or imaging system configured for optical imaging of the sample or microscopy in the sample.

At least one embodiment includes a system having: first and second passively mode locked oscillators, the oscillators configured to operate at slightly different repetition rates, such that a difference $\delta f_r$ in repetition rates is small compared to the values $f_{r1}$ and $f_{r2}$ of the repetition rates of the first and second oscillators. The first oscillator generates multiple frequency lines separated by $f_{r1}$ within a first optical emission envelope. The second oscillator generating multiple frequency lines being separated by $f_{r2}$ within a second optical emission envelope. The system may be configured for emission measurements using Fourier transform spectroscopy techniques In various embodiments the system is configured to probe one or both of spontaneous and stimulated Raman emission spectra in one or both of reflection or transmission.

In various embodiments the system is configured to probe a spectral output of a device emitting electro-magnetic radiation.

In various embodiments the system is configured for spontaneous Raman microscopy.

In various embodiments the system is configured for stimulated Raman microscopy.

In various embodiments the system configured for stimulated coherent anti-Stokes Raman microscopy.

In various embodiments emission may be resonantly enhanced.

In various embodiments Raman emission may be enhanced with surface enhanced Raman scattering or resonant Raman scattering.

At least one embodiment includes a system having: first and second passively mode locked oscillators, the oscillators configured to operate at slightly different repetition rates, such that a difference $\delta f_r$ in repetition rates is small compared to the values $f_{r1}$ and $f_{r2}$ of the repetition rates of the first and second oscillators. The first oscillator generates multiple frequency lines separated by $f_{r1}$ within a first optical emission envelope. The second oscillator generates multiple frequency lines separated by $f_{r2}$ within a second optical emission envelope. The system includes a test sample. The system is configured such that second oscillator emission is coupled into the test sample, the test sample coherently modifying the emission resulting from the second oscillator emerging from the test sample. The first oscillator is configured as a local oscillator which samples the emission emerging from the test sample.

Various embodiments include a means for spectral broadening and filtering of the oscillator outputs, and the means may include a highly non-linear fiber and/or an optical filter, for example.

At least one embodiment includes a system having: first and second passively mode locked oscillators, the oscillators configured to operate at slightly different repetition rates, such that a difference $\delta f_r$ in repetition rates is small compared to the values $f_{r1}$ and $f_{r2}$ of the repetition rates of the first and second oscillators. The first oscillator generates multiple frequency lines separated by $f_{r1}$ within a first optical emission envelope. The second oscillator generates multiple frequency lines separated by $f_{r2}$ within a second optical emission envelope. The output of one of the oscillators is coupled into a test sample. The test sample modifies the emission resulting from an oscillator output emerging from the test sample. The system may be configured for testing one of more of spectral, spectral phase, temporal and temporal phase characteristics of the modified emission.

In various embodiments the system includes a means for spectral broadening and filtering of the oscillator outputs.

In various embodiments a system may be configured: to generate a strong pump and a weak probe beam from the first oscillator with an adjustable time delay between the pump and probe pulses, where the second oscillator is configured to produce a signal beam, with the pump and probe beam coupled into an optical sample, and wherein the second oscillator generates an output representative of a change induced on a propagation characteristics of the probe beam by the pump beam.

At least one embodiment includes a method for obtaining Raman spectra from an optical sample. The method includes: measuring the phase perturbations of a probe pulse induced by a pump pulse during propagation through the sample, wherein the pump and probe pulse are generated by a first mode locked signal laser, and the phase measurement is derived from a signal generated by a second mode locked laser operating as a local oscillator, wherein the first and second lasers are configured to operate at slightly different repetition rates.

At least one embodiment includes a method for obtaining emission spectra from an optical sample. The method includes measuring the sample emission induced by a pump pulse during propagation through the sample, the pump pulse being generated with a first mode locked signal laser. The emission measurement is derived by a multiplication of a first and a second interference signal. The first interference signal is derived from optically interfering the pump pulse with the sample emission. The second interference signal is derived from optically interfering the sample emission with a signal generated by a second mode locked laser operating as a local oscillator laser. The first and second lasers are configured to operate at slightly different repetition rates.

At least one embodiment includes a system. The system includes first and second passively mode locked oscillators, the oscillators configured to operate at slightly different repetition rates, such that a difference $\delta f_r$ in repetition rates is small compared to the values $f_{r1}$ and $f_{r2}$ of the repetition rates of the first and second oscillators. The first oscillator generates multiple frequency lines separated by $f_{r1}$ within a first optical emission envelope. The second oscillator generates multiple frequency lines being separated by $f_{r2}$ within a second optical emission envelope. The system may be configured for two dimensional emission/absorption spectral measurements.

In various embodiments two dimensional Fourier transform spectroscopy techniques are implemented for the extraction of two-dimensional emission/absorption spectral information.

In various embodiments a system may be configured for multi-dimensional spectroscopy.

In various embodiments a ratio of a repetition rate of an oscillator to the difference in repetition rates of first and second oscillators may be in the range from about $10^6$ to about $10^9$.

In various embodiments first and second oscillators may have substantially similar emission envelopes.

In various embodiments a CDSL may include a digital and/or analog phase locked loop.

In various embodiments imaging equipment may include a focal plane array detector.

At least one embodiment includes a coherent scanning laser system for generating pulse pairs with a time varying time delay. The system includes an optical source to generate an output, including optical pulses at a repetition rate, wherein a repetition rate of the optical source is modulated. The source includes: at least one mode locked oscillator upstream of the output, and a first beam splitter configured to beam split the output into two optical paths having different propagation lengths. The pulses propagating along the two optical paths are recombined at a second beam splitter.

In various embodiments one optical path may include an optical delay line which includes a length of optical fiber. The length may be in the range from about 10 meters to several tens of km. In some embodiments the length may be in the range from about 100 m to 10 km, about 5 m to 100 m, or other similar ranges.

In various embodiments the first and second beamsplitters are identical.

In various embodiments a coherent scanning laser system is configured for Fourier transform spectroscopy.

At least one embodiment includes coherent scanning laser system for generating pulse pairs with a time varying time delay. The system includes an optical source having at least one mode locked oscillator. The source generates optical pulses at a time-varying repetition rate. A repetition rate modulator is configured to modulate the repetition rate at a modulation rate. The source generates an output that includes the pulse pairs, The system includes an optical reference having at least one optical element configured for generating a reference signal for measurement of at least the time delay between the two pulses of the pulse pair as a function of time.

In various embodiments the rate of change of the time delay between the pulse pairs may be identical to the modulation rate and/or a function of the modulation rate.

In various embodiments the source includes a first beam divider downstream of the mode locked oscillator, the beam divider configured to propagate the output of the mode locked oscillator along two optical paths having different propagation lengths; and a beam combiner configured to recombine the pulses propagating along the two optical paths.

A beam divider and/or beam combiner may include a bulk optical component, for example a bulk optic beam splitter. In some embodiments fiber couplers and/or any suitable integrated optical device may be utilized, alone or in combination with bulk optical elements.

In various embodiments a beam divider and beam combiner are constructed from identical components.

In various embodiments a beam divider and/or beam combiner may include a fiber coupler, a bulk optical beam splitter, or a combination thereof.

In various embodiment a source includes a second mode locked oscillator operating at a second repetition rate. A first pulse from the pulse pair is generated with the first source. A second pulse from the pulse pair is generated with the second source.

The second repetition rate of the second oscillator may be approximately constant.

In various embodiments at least one optical element is configured to provide for a measurement of a difference in carrier envelope phase between the two pulses of the pulse pair.

In various embodiments a repetition rate modulator modulates a cavity length of an oscillator.

A repetition rate modulator may include one of a cavity mirror mounted on a piezo-electric transducer, a MEMS, MOEMS mirror, acousto-optic or an intra-cavity electro-optic modulator.

An optical reference may include an interferometer to measure a location of an intra-cavity element of the mode locked oscillator.

An intra-cavity element may include a cavity mirror of the mode locked oscillator.

An optical reference may include at least one narrow band-pass spectral filter to filter the pulse pairs.

An optical reference may include at least one cw reference laser configured to record beat signals between the pulse pairs and the at least one reference laser.

In various embodiments a stabilizer is included for active stabilization of the differential propagation length.

A reference laser may be configured to measure a differential propagation length.

In various embodiments a spectral broadening stage may be disposed down-stream of the source or the mode locked oscillator.

In various embodiments a spectral broadening stage may include an optical parametric oscillator.

In various embodiments an optical parametric oscillator may include a gas cell for trace gas detection.

A spectral broadening stage may be included in the source and/or disposed downstream from the source.

In various embodiments optical components for dispersion compensation may be included, and may be configured for equalization of the dispersion along the different propagation paths.

In various embodiment detectors are provided to detect an interferogram between the pulse pairs. Various embodiments may include a means for generating sampling points at equidistant optical path length differences between the pulses comprising the pulse pair.

A means for generating sampling points may include a digital and/or analog signal processor, and may be programmable.

In various embodiments a coherent scanning laser system may be configured as a portion of a system for Fourier transform spectroscopy.

In various embodiments a modulation rate of a repetition rate modulator may be greater than about 1 Hz.

In various embodiments a modulation rate of a repetition rate modulator may be greater than about 10 Hz. In various embodiments a modulation rate of a repetition rate modulator may be greater than about 1 kHz.

Various embodiments may include a means for stabilizing the average of the first repetition rate to be equal to the second repetition rate, characterized in that the time interval between pulse crossing events between the pulses from the two oscillators is approximately constant as a function of time.

In various embodiments a means for generating sampling points at equidistant optical path length differences includes detecting a reference interferogram and using the zero-crossing points of the reference interferogram for sampling of a second interferogram.

In various embodiments a coherent scanning laser system may be configured as a portion of a system for two-dimensional Fourier transform spectroscopy.

At least one embodiment includes A coherent dual scanning laser system (CDSL). The system may include first and second passively mode locked oscillators configured to operate at slightly different repetition rates, such that a difference $\Delta f_r$ in repetition rates is small compared to the values $f_{r1}$ and $f_{r2}$ of the repetition rates of the first and second oscillators. The system includes at least one enhancement cavity for multiplying the repetition rate of at least one oscillator by an integer factor; a means for locking the repetition rate and phase of the at least one oscillator to the at least one enhancement cavity. The system further includes a means for detection an interferogram between the two oscillators after repetition rate multiplication of the one oscillator.

Various embodiments include a non-linear frequency conversion section optically connected to each oscillator, the section comprising a non-linear optical element generating a frequency converted spectrum with a spectral coverage exceeding the spectral coverage of the oscillators.

In various embodiments an optical reference generates a calibration signal, and the system further includes a signal processor receiving the calibration signal and calibrating the time-varying pulse delays as a function of time for more than one modulation cycle of the repetition rate modulator.

In various embodiments a CDSL is configured for pump probe measurements.

Various embodiments include an element for amplification of the pulses along at least a portion of the two propagation paths, for example at least one fiber amplifier.

Optical propagation paths may include one or both of a bulk optical component and a length of optical fiber.

At least one embodiment includes a coherent scanning laser system for generating pulse pairs with a time varying time delay. The system includes an optical source generating an output. The output includes optical pulses at a repetition rate. The repetition rate is modulated. The source includes at least one mode locked oscillator upstream of the output of said source and a first beam splitter. The beam splitter splitting the output into two optical paths, having different propagation lengths, and the pulses propagating along the two optical paths are recombined at a second beam splitter.

In various embodiments the first and second beam splitters are identical.

In various embodiments the system is configured for Fourier transform spectroscopy.

At least one embodiment includes a coherent dual scanning laser system (CDSL). The system includes first and second passively mode locked oscillators, the oscillators configured to operate at slightly different repetition rates, $f_{r1}$ and $f_{r2}$, respectively, such that a difference in repetition rates $\delta f_r = f_{r1} - f_{r2}$, is small compared to the values $f_{r1}$ and $f_{r2}$ of the repetition rates of the first and second oscillators. The first oscillator generates multiple frequency lines separated by $f_{r1}$ within a first optical emission envelope. The second oscillator generates multiple frequency lines separated by $f_{r2}$ within a second optical emission envelope. The first and second mode locked oscillators further configured to operate with two carrier envelope offset frequencies, $f_{ceo1}$ and $f_{ceo2}$ respectively, with a difference in the carrier envelope offset frequencies of $\Delta f_{ceo} = f_{ceo1} - f_{ceo2}$, where $\Delta f_{ceo}$ is not necessarily different from zero. The system further includes at least one cw reference laser operating at a respective cw reference frequency $f_x$, the cw reference laser being optically connected with each of the first and second oscillators, and having an output located within the emission envelope of each of the oscillators. The cw reference laser has a frequency separated by $f_{b1}$ from a frequency line of the first oscillator and separated by $f_{b2}$ from a frequency line of the second oscillator. The system further includes: a means for generating at least one RF signal proportional to any of $\Delta f_2 = f_{b1} - f_{b2}$, $f_{b1}$, $f_{b2}$, $\delta f_r$, $f_{r1}$, $f_{r2}$, $\Delta f_{ceo}$, $f_{ceo1}$, $f_{ceo2}$, wherein the RF signal is stabilized to an external RF reference signal; a means for detecting the residual phase difference between the RF signal and the RF reference signal; and a means, comprising a signal processor, for applying the detected phase difference to obtain corrections to the value of any of $\Delta f_2$, $f_{b1}$, $f_{b2}$, $\delta f_r$, $f_{r1}$, $f_{r2}$, $\Delta f_{ceo}$, $f_{ceo1}$, $f_{ceo2}$.

In various embodiments of coherent dual scanning laser system (CDSL), the RF signal is stabilized to said external RF reference via phase locked loops or a frequency locking scheme.

In various embodiments the signal processor may be operatively connected to process any information signal derived from $\Delta f_2$, $f_{b1}$, $f_{b2}$, $\delta f_r$, $f_{r1}$, $f_{r2}$, $\Delta f_{ceo}$, $f_{ceo1}$, $f_{ceo2}$ and the reference and may provide correction(s) via a phase locked loop. At least one embodiment includes a coherent dual scanning laser system (CDSL). The system includes first and second passively mode locked oscillators. The oscillators are configured to operate at slightly different repetition rates, such that a difference $\delta f_r$ in repetition rates is small compared to values $f_{r1}$ and $f_{r2}$ of the repetition rates of the first and second oscillators. The first oscillator generates multiple frequency lines separated by $f_{r1}$ within a first optical emission envelope and the second oscillator generates multiple frequency lines separated by $f_{r2}$ within a second optical emission envelope. The system also includes: means for detecting beat frequencies $\Delta f_2$ and $\Delta f_1$, the beat frequencies corresponding to the difference between two next neighbor comb lines from the two oscillators at two different locations within the optical emission envelope. The means for detecting the beat frequencies utilizes optical combining of the output of the two mode locked oscillators and passing the combined output through two separate narrow bandpass optical filters. The beat frequencies are locked to external RF reference signals via phase locked loops.

In various embodiments the coherent scanning laser system is configured as a portion of a system for Fourier transform spectroscopy with a spectral resolution<1 cm$^{-1}$.

In various embodiments the coherent scanning laser system is configured as a portion of a system for Fourier transform spectroscopy with a spectral resolution<0.1 cm$^{-1}$.

In various embodiments the coherent scanning laser system may include a dual balanced detection arrangement to limit amplitude noise in an interferogram.

Thus, while only certain embodiments have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the embodiments described therein.

What is claimed is:

1. A coherent scanning laser system for generating pulse pairs with a time varying time delay, said system comprising:
    an optical source, said source comprising: at least one mode locked oscillator, said source generating optical pulses at a time-varying repetition rate;
    a repetition rate modulator configured to modulate said repetition rate at a modulation rate, wherein said repetition rate modulator is configured to modulate a cavity length of said mode locked oscillator;
    an optical delay line arranged to receive optical pulses modulated at said modulation rate and to generate said pulse pairs, wherein a time delay between pulses of said pulse pair is dependent on said modulation rate; and
    an optical reference comprising at least one bandpass filter, said optical reference configured for generating a reference signal for measurement of at least the time delay between the two pulses of said pulse pair as a function of time.

2. A coherent scanning laser system according to claim 1, wherein each said pulse pair comprises a direct pulse and a time delayed replica of said direct pulse, and said system comprises:
    a first beam divider downstream of said mode locked oscillator, said beam divider configured to propagate the output of said mode locked oscillator along two separate optical paths having different propagation lengths, said delay line being inserted in one of said optical paths; and
    a beam combiner configured to recombine said pulses propagating along said two optical paths and to form said pulse pair having said direct pulse and said time delayed replica thereof.

3. A coherent scanning laser system according to claim 2, wherein said beam divider and/or beam combiner comprise a fiber coupler, a bulk optical beam splitter, or a combination thereof.

4. A coherent scanning laser system according to claim 1, further comprising at least one optical element configured to provide for a measurement of a difference in carrier envelope phase between the two pulses of said pulse pair.

5. A coherent scanning laser system according to claim 1, said modulation rate being greater than about 10 Hz.

6. A coherent scanning laser system according to claim 2, further comprising a stabilizer for active stabilization of said two optical paths having different propagation lengths.

7. A coherent scanning laser system according to claim 2, further comprising a path length stabilizer, including a reference laser, said path length stabilizer configured to measure said different propagation lengths.

8. A coherent scanning laser system according to claim 1, further comprising a spectral broadening stage downstream of said source or said mode locked oscillator.

9. A coherent scanning laser system according to claim 2, further comprising an element for equalization of the dispersion along said different propagation paths.

10. A coherent scanning laser system according to claim 1, further comprising detectors to detect an interferogram between said pulse pairs.

11. A coherent scanning laser system according to claim 1, further comprising means for generating sampling points at equidistant optical path length differences between the pulses comprising said pulse pair.

12. A coherent scanning laser system according to claim 1, said coherent scanning laser system configured as a portion of a system for Fourier transform spectroscopy.

13. A coherent scanning laser system according to claim 1, said modulation rate being greater than about 1 kHz.

14. A scanning laser system according to claim 11, said means for generating sampling points at equidistant optical path length differences further comprising detection of a reference interferogram and using the zero-crossing points of the reference interferogram for sampling of a second interferogram.

15. A coherent scanning laser system according to claim 2, further comprising an element for amplification of the pulses along at least a portion of said two propagation paths.

16. A coherent scanning laser system according to claim 2, wherein said optical paths comprise one or both of a bulk optical component or a length of optical fiber.

17. A coherent scanning laser system according to claim 1, said coherent scanning laser system configured as a portion of a system for Fourier transform spectroscopy with a spectral resolution<1 cm$^{-1}$.

18. A coherent scanning laser system according to claim 1, said coherent scanning laser system configured as a portion of a system for Fourier transform spectroscopy with a spectral resolution<0.1 cm$^{-1}$.

19. A coherent scanning laser system according to claim 8, said spectral broadening stage comprising an optical parametric oscillator.

20. A coherent scanning laser system according to claim 19, said optical parametric oscillator further comprising a gas cell for trace gas detection.

21. A coherent scanning laser system according to claim 10, further comprising a dual balanced detection arrangement to limit amplitude noise in said interferogram.

22. A coherent scanning laser system according to claim 10, further comprising a spectral broadening stage comprising an optical parametric oscillator.

23. A coherent scanning laser system according to claim 22, said optical parametric oscillator further comprising a gas cell for trace gas detection.

24. A coherent scanning laser system according to claim 2, wherein an output of said beam combiner is directed to a downstream sample for measurement of phase, absorption and/or emission spectra of said sample.

25. A coherent scanning laser system according to claim 1, wherein said optical bandpass filter comprises a grating disposed downstream from said optical source and said delay line.

26. A coherent scanning laser system according to claim 1, wherein said at least one bandpass filter comprises a fiber grating.

27. A coherent scanning laser system according to claim 1, wherein said pulse pair comprises an optical pulse and a time delayed replica of said optical pulse.

28. A coherent scanning laser system for generating pulse pairs with a time varying time delay, said system comprising:
   an optical source, said source comprising: at least one mode locked oscillator, said source generating optical pulses at a time-varying repetition rate;
   a repetition rate modulator configured to modulate said repetition rate at a modulation rate, wherein said repetition rate modulator is configured to modulate a cavity length of said mode locked oscillator;
   an optical delay line arranged to receive optical pulses modulated at said modulation rate and to generate said pulse pairs, wherein a time delay between pulses of said pulse pair is dependent on said modulation rate; and
   at least two optical references comprising at least two optical bandpass filters configured for generating reference signals for tracking the time delay and compensating for the carrier envelope offset frequency fluctuations between said pulse pairs as a function of time.

29. A coherent scanning laser system for generating pulse pairs with a time varying time delay according to claim 28, said two bandpass filters constructed from narrow bandpass fiber gratings.

30. A coherent scanning laser system according to claim 9, wherein said element for equalization of dispersion comprises a pulse compressor.

31. A coherent scanning laser system according to claim 9, wherein said element for equalization of dispersion comprises a low dispersion optical fiber.

32. A coherent scanning laser system according to claim 9, wherein said element for equalization of dispersion comprises a bulk optic delay line.

33. A coherent scanning laser system according to claim 15, wherein said element for amplification of pulses comprises at least one fiber amplifier.

34. A coherent scanning laser system according to claim 33, wherein said beam divider and/or beam combiner comprises a fiber coupler, a bulk optical beam splitter, or a combination thereof.

* * * * *